(12) United States Patent
Craig et al.

(10) Patent No.: US 6,670,144 B1
(45) Date of Patent: *Dec. 30, 2003

(54) COMPOSITIONS AND METHODS FOR MONITORING THE PHOSPHORYLATION OF NATURAL BINDING PARTNERS

(75) Inventors: Roger K. Craig, Cheshire (GB); John Colyer, West Yorkshire (GB)

(73) Assignee: Cyclacel, Ltd., Scotland (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/511,204

(22) Filed: Feb. 23, 2000

Related U.S. Application Data

(63) Continuation-in-part of application No. 09/258,981, filed on Feb. 26, 1999.

(51) Int. Cl.[7] .................. G01N 33/53; G01N 33/542; C12Q 1/42; C12N 9/00; C12N 9/96

(52) U.S. Cl. .................. 435/21; 435/7.8; 435/7.9; 435/7.91; 435/183; 435/188; 435/188.5; 435/194

(58) Field of Search .................. 424/94.3; 435/7.1, 435/7.8, 7.9, 21, 91.53, 188, 960, 964, 967; 436/537, 544, 546; 536/25, 32

(56) References Cited

U.S. PATENT DOCUMENTS

| | | | | |
|---|---|---|---|---|
| 5,283,173 A | * | 2/1994 | Fields et al. | 435/6 |
| 5,383,023 A | * | 1/1995 | Walleczek | 356/417 |
| 5,580,859 A | | 12/1996 | Felgner et al. | 514/44 |
| 5,637,463 A | * | 6/1997 | Dalton et al. | 435/6 |

FOREIGN PATENT DOCUMENTS

| | | | | |
|---|---|---|---|---|
| EP | WO 97/28261 | * | 8/1997 | C12N/15/12 |
| WO | WO92/00388 | | 1/1992 | |
| WO | WO 92/00388 | * | 1/1992 | C12Q/1/68 |
| WO | PCT/US95/14692 | | 11/1995 | |
| WO | WO 96/40116 | * | 12/1996 | A61K/31/40 |
| WO | WO97/28261 | | 8/1997 | |
| WO | WO98/06737 | | 2/1998 | |
| WO | WO 98/06737 | * | 2/1998 | C07H/21/04 |
| WO | WO 98/07835 | * | 2/1998 | C12N/9/00 |

OTHER PUBLICATIONS

Arnheiter, et al., *Nature*, 294:278–280 (1981).
Atherton, et al., *J. Chem. Soc. Perkin I.*, 1981(2):538–546.
Balázs, et al., *Gene*, 40:343–348 (1985).
Banerji, et al., *Cell*, 33:729 (1983).
Boersma and van Leeuwen, *J. Neurosci. Methods*, 51:317 (1994).
Boggs, *Int. J. Cell Cloning*, 8:80 (1990).
Bolivar, et al., *Gene*, 2:95–113 (1977).
Brown and Cooper, *Biochem. Biophys. Acta.*, 1287:121–149 (1996).
Carrier, et al., *J. Immunol.*, 148:1176–1181 (1992).
Chabalgoity, et al., *Infect. Immunol.*, 65:2402–2412 (1996).
Chang, et al., *J. Bacteriol.*, 134:1141–1156 (1978).
Clarke and Woodland, *Rhematol. Rehabil.*, 14:47–49 (1975).
Dymecki, et al., *J. Biol. Chem.*, 267:4815–4823 (1992).
Eigen and Rigler, *Proc. Natl. Acad. Sci. USA*, 91:5740–5747 (1994).
Elson and Madge, *Biopolymers*, 13:1–27 (1974).
Fox, et al., *Gene Therapy*, 3:173–178 (1996).
Garapin, et al., *Proc. Natl. Acad. Sci. USA*, 78:815–819 (1981).
Green, et al., *Cell*, 28:477–487 (1982).
Heim, et al., *Proc. Natl. Acad. Sci. USA*, 91:12501–12504 (1994).
Hengge, et al., *Nature Genet.*, 10:161–166 (1995).
Hickman, et al., *Human Gene Therapy*, 5:1477–1483 (1994).
Hubbard, et al., *J. Clin. Invest.*, 84:1349–1354 (1989).
Jackson, et al., *Proc. Natl. Acad. Sci. USA*, 69:2904–1909 (1972).
Jovin and Jovin, *Cell Structure and Function by Microspectrofluorometry*, Kohen and Hirschberg, eds., Academic Press (1989).
Kahn, et al., *Methods Enzymol.*, 68:268–280 (1979).
Kinjo and Rigler, *Nucleic Acids Res.*, 23:1795–1799 (1995).
Laemmli, *Nature*, 227:680–685 (1970).
Lakowicz, *Principles of Fluorescence Spectroscopy*, Plenum Press, NY (1983).
Laminet, et al., *J. Biol. Chem.*, 271:264–269 (1996).
Levine, et al., *Comp. Biochem. Physiol.*, 72B:77–85 (1982).
Lupher, et al., *J. Biol. Chem.*, 271:24063–24068 (1996).
Lupher, et al., *J. Biol. Chem.*, 272:33140–33144 (1997).
Maccarrone, et al., *Biochem. Biophys. Res. Comm.*
Mannion–Henderson, et al., *Exp. Hematol.*, 23:1628 (1995).
Mårtensson, et al., *Eur. J. Immunol.*, 17:1499 (1987).
Mátyus, *J. Photochem. Photobiol. B.: Biol.*, 12:323–337 (1992).
Merrifield, *J. Am. Chem. Soc.*, 85:2149–2154 (1963).
Meyer, et al., *Gene Therapy*, 2:450–460 (1995).
Minton, et al., *FEMS Microbiol. Rev.*, 17:354–364 (1995).
Okabe, et al., *Eur. J. Immunol.*, 22:37–43 (1992).
Olszewski, et al., *Nucleic Acids Res.*, 10765–10782 (1988).
Pan, et al., *Nature Med.*, 1:471–477 (1995)51.
Pawalek, et al., *Cancer Res.*, 57:4537–4544 (152.997).
Perez, et al., *Plant Mol. Biol.*, 13:365–373 (1989)53.
Peters, et al, *Biochemistry*, 16:5691–5697 (1977)54.
Prasher, et al., *Gene*, 111:229–233 (1992)55.

(List continued on next page.)

*Primary Examiner*—Lynette R. F. Smith
*Assistant Examiner*—Jana Hines
(74) *Attorney, Agent, or Firm*—Kathleen M. Williams; Palmer & Dodge LLP

(57) ABSTRACT

This invention relates to methods and compositions for monitoring the interaction of binding partners as a function of the addition or subtraction of a phosphate group to or from one of the binding partners by a protein kinase or phosphatase.

6 Claims, 15 Drawing Sheets-

OTHER PUBLICATIONS

Figure 1:
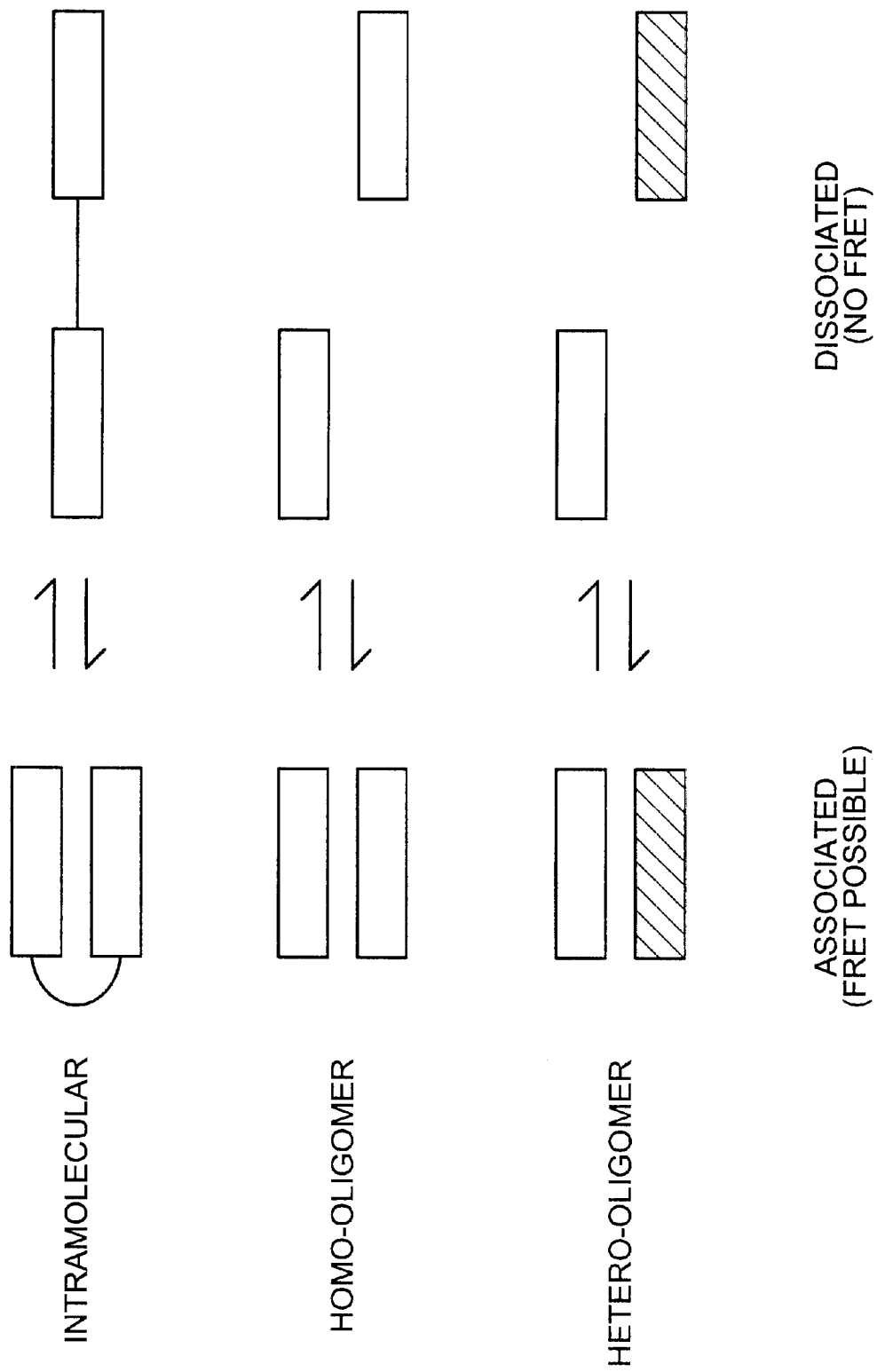

Riabowol, et al., *Cold Spring Harbor Sympo56.sia on Quantitative Biology*, 53:85–90 (1988).
Rigler, et al., *Fluorescence Spectroscopy: New 57.Methods and Applications*, Springer Verlag, 13–24 (1992).
Roussell, et al., *Mol. Gen. Genet.*, 211:202–209 (158.988).
Saalbach, et al., *Mol. Gen. Genet.*, 242:226–236 (199459).
Saltzmann, et al., *Cancer Biother. Radiopharm.*, 11:145–60.153 (1996).
Sambrook, et al., *Molecular Cloning: A Laboratory Manual61.*, 2nd ed., Cold Spring Harbor Laboratory Press, Cold Spring Harbor, NY (1989).
Schafer, et al., *J. Immunol.*, 149:53–59 (1992).
Schiffmann, et al., *Blood*, 86:1218 (1995).
Scott, *Microbial Reviews*, 48:1–23 (1984).
Sizemore, et al., *Science*, 270:299–302 (1995).
Songyang, et al., *Cell*, 72:767–778 (1993).
Spatola, in *Chemistry and Biochemistry of Amino Acids, Peptides and Proteins*, Weinstein, ed., Marcel Dekker, NY (1983).
Stoker, et al., *Gene*, 18:335–341 (1982).
Su, et al., *Microbiol. Pathol.*, 13:465–476 (1992).
Sullivan, *J. Invest. Dermatol.*, 103:85S–98S (1994).
Sikes, et al., *Human Gene Ther.*, 5:837–844 (1994).
Talmadge, et al., *Proc. Natl. Acad. Sci. USA*, 77:3369–3373 (1980).
Turpen, et al., *J. Virol. Methods*, 42:227–239 (1993).
Uhlin, et al., *Gene*, 22:255–265 (1983).
Usman, et al., *Curr. Opin. Struct. Biol.*, 6:527–533 (1996).
Vile, et al., *Cancer Res.*, 53:962–967 (1993).
Waksman, et al., *Cell*, 72:779–790 (1993).
Ward, et al., *Photochem. Photobiol.*, 35:803–808 (1982).
Williams, *Bone Marrow Transplant*, 5:141 (1990).
Wolff, et al., *Science*, 247:1465–1468 (1990).
Woo, et al., *Nature*, 394:700–704 (1998).
Xu, et al., *Nature*, 394:700–704 (1998).
Zhou, et al., *Nature Structural Biology*, 3:388–393 (1996).

* cited by examiner

EXCIMER CONFIGURATION OF PYRENE PAIRS

SEQUENCE LISTING

<160> NUMBER OF SEQ ID NOS: 20

<210> SEQ ID NO 1
<211> LENGTH: 12
<212> TYPE: PRT
<213> ORGANISM: Homo sapiens

<400> SEQUENCE: 1

Phe Leu Pro Val Pro Glu Tyr Ile Asn Gln Ser Val
 1               5                  10

<210> SEQ ID NO 2
<211> LENGTH: 12
<212> TYPE: PRT
<213> ORGANISM: Homo sapiens

<400> SEQUENCE: 2

Ala Val Gly Asn Pro Glu Tyr Leu Asn Thr Val Gln
 1               5                  10

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Tumor
      suppressor protein p53 phosphorylation site

<400> SEQUENCE: 3

Glu Pro Pro Leu Ser Gln Glu Ala Phe Ala Asp Leu Trp Lys Lys
 1               5                  10                  15

<210> SEQ ID NO 4
<211> LENGTH: 11
<212> TYPE: PRT
<213> ORGANISM: HAMSTER

<400> SEQUENCE: 4

Glu Pro Gln Tyr Glu Glu Ile Pro Ile Tyr Leu
 1               5                  10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Interleukin
      4 receptor binding domain

<400> SEQUENCE: 5

Leu Val Ile Ala Gly Asn Pro Ala Tyr Arg Ser
 1               5                  10

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: ZAP-70
      binding domain

<400> SEQUENCE: 6

Ile Asp Thr Leu Asn Ser Asp Gly Tyr Thr Pro Glu Pro Ala Arg Ile
 1               5                  10                  15

```
<210> SEQ ID NO 7
<211> LENGTH: 36
<212> TYPE: PRT
<213> ORGANISM: Artificial Sequence
<220> FEATURE:
<223> OTHER INFORMATION: Description of Artificial Sequence:
      Phosphorylated TCR-zeta chain

<400> SEQUENCE: 7
```

Arg Cys Lys Phe Ser Arg Ser Ala Glu Pro Pro Ala Tyr Gln Gln Gly
 1               5                  10                  15

Gln Asn Gln Leu Tyr Asn Glu Leu Asn Leu Gly Arg Arg Glu Glu Tyr
            20                  25                  30

Asp Val Leu Asp
        35

```
<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Forward PCR
      primer for SH2 domain of ZAP-70

<400> SEQUENCE: 8
gggatccata tgccagaccc cgcggcgcac ctg                               33

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Reverse PCR
      primer for SH2 domain of ZAP-70

<400> SEQUENCE: 9
ggaattcggg cactgctgtt ggggcaggcc tcc                               33

<210> SEQ ID NO 10
<211> LENGTH: 23
<212> TYPE: PRT
<213> ORGANISM: Artificial Sequence
<220> FEATURE:
<223> OTHER INFORMATION: Description of Artificial Sequence: Chk1
      substrate peptide sequence

<400> SEQUENCE: 10
```

Lys Lys Lys Val Ser Arg Ser Gly Leu Tyr Arg Ser Pro Ser Met Pro
 1               5                  10                  15

Glu Asn Leu Asn Arg Pro Arg
            20

```
<210> SEQ ID NO 11
<211> LENGTH: 31
<212> TYPE: PRT
<213> ORGANISM: Artificial Sequence
<220> FEATURE:
<223> OTHER INFORMATION: Description of Artificial Sequence: PKA peptide
      sequence

<400> SEQUENCE: 11
```

Glu Arg Glu Ile Lys Ala Leu Glu Arg Glu Ile Arg Arg Leu Arg Arg
 1               5                  10                  15

Ala Ser Gln Ala Leu Glu Arg Glu Ile Ala Gln Leu Glu Arg Glu
            20                  25                  30

<210> SEQ ID NO 12
<211> LENGTH: 32
<212> TYPE: PRT
<213> ORGANISM: Artificial Sequence
<220> FEATURE:
<223> OTHER INFORMATION: Description of Artificial Sequence: PKA peptide
      sequence

<400> SEQUENCE: 12

Leu Arg Gln Arg Ile Gln Cys Leu Arg Tyr Arg Ile Arg Arg Leu Arg
 1               5                  10                  15

Arg Ala Ser Gln Ala Leu Arg Gln Arg Ile Ala Gln Leu Lys Gln Arg
             20                  25                  30

<210> SEQ ID NO 13
<211> LENGTH: 36
<212> TYPE: PRT
<213> ORGANISM: Artificial Sequence
<220> FEATURE:
<223> OTHER INFORMATION: Description of Artificial Sequence:
      Phosphorylated TCR-zeta chain

<400> SEQUENCE: 13

Arg Cys Lys Phe Ser Arg Ser Ala Glu Pro Pro Ala Tyr Gln Gln Gly
 1               5                  10                  15

Gln Asn Gln Leu Tyr Asn Glu Leu Asn Leu Gly Arg Arg Glu Glu Tyr
             20                  25                  30

Asp Val Leu Asp
         35

<210> SEQ ID NO 14
<211> LENGTH: 36
<212> TYPE: PRT
<213> ORGANISM: Artificial Sequence
<220> FEATURE:
<223> OTHER INFORMATION: Description of Artificial Sequence:
      Un-phosphorylated TCR-zeta chain

<400> SEQUENCE: 14

Arg Cys Lys Phe Ser Arg Ser Ala Glu Pro Pro Ala Tyr Gln Gln Gly
 1               5                  10                  15

Gln Asn Gln Leu Tyr Asn Glu Leu Asn Leu Gly Arg Arg Glu Glu Tyr
             20                  25                  30

Asp Val Leu Asp
         35

<210> SEQ ID NO 15
<211> LENGTH: 40
<212> TYPE: PRT
<213> ORGANISM: Artificial Sequence
<220> FEATURE:
<223> OTHER INFORMATION: Description of Artificial Sequence: SHPS-1
      peptide sequence

<400> SEQUENCE: 15

Lys Gln Asp Thr Asn Asp Ile Thr Tyr Ala Asp Leu Asn Leu Pro Lys
 1               5                  10                  15

Gly Lys Lys Pro Ala Pro Gln Ala Ala Glu Pro Asn Asn His Thr Glu
             20                  25                  30

Tyr Ala Ser Ile Gln Thr Ser Cys
         35                  40

```
<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence: Forward PCR
      primer for SH2 domain of SHP-2

<400> SEQUENCE: 16
ggggatcctc tagaatgaca tcgcggagat ggtttcaccc                              40

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: Reverse PCR
      primer for SH2 domain of SHP-2

<400> SEQUENCE: 17
ggggaattct ttcagcagca tttatacgag tcg                                     33

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: v-SRC SH2
      domain

<400> SEQUENCE: 18

Glu Pro Gln Tyr Glu Glu Ile Pro Ile Tyr Leu
 1               5                  10

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence:
      Phosphotyrosine binding domain of IRS-1

<400> SEQUENCE: 19

Leu Val Ile Ala Gly Asn Pro Ala Tyr Arg Ser
 1               5                  10

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence:
      Phosphytyrosine binding domain of Cb1

<400> SEQUENCE: 20

Ile Asp Thr Leu Asn Ser Asp Gly Tyr
 1               5
```

COMPOSITIONS AND METHODS FOR MONITORING THE PHOSPHORYLATION OF NATURAL BINDING PARTNERS

This application is a continuation-in-part of application Ser. No. 09/258,981, filed Feb. 26, 1999.

FIELD OF THE INVENTION

The invention relates to monitoring of phosphorylation or dephosphorylation of a protein.

BACKGROUND OF THE INVENTION

The post-translational modification of proteins has been known for over 40 years and since then has become a ubiquitous feature of protein structure. The addition of biochemical groups to translated polypeptides has wide-ranging effects on protein stability, protein secondary/tertiary structure, enzyme activity and in more general terms on the regulated homeostasis of cells. Such additions include, but are not limited to, protein phosphorylation and dephosphorylation.

Phosphorylation is a well-studied example of a post-translational modification of proteins. There are many cases in which polypeptides form higher order tertiary structures with like polypeptides (homo-oligomers) or with unalike polypeptides (hetero-oligomers). In the simplest scenario, two identical polypeptides associate to form an active homodimer. An example of this type of association is the natural association of myosin II molecules in the assembly of myosin into filaments.

The dimerization of myosin II monomers is the initial step in seeding myosin filaments. The initial dimerization is regulated by phosphorylation, the effect of which is to induce a conformational change in myosin II secondary structure resulting in the folded 10S monomer subunit extending to a 6S molecule. This active molecule is able to dimerize and subsequently to form filaments. The involvement of phosphorylation of myosin II in this priming event is somewhat controversial. Although in higher eukaryotes the conformational change is dependant on phosphorylation, in Ancanthoamoeba, a lower eukaryote, the post-translational addition of phosphate is not required to effect the initial dimerization step. It is of note that the dimerization domains in myosin II of higher eukaryotes contain the sites for phosphorylation and it is probable that phosphorylation in this region is responsible for enabling myosin II to dimerize and subsequently form filaments. In Dictyostelium this situation is reversed in that the phosphorylation sites are outside the dimerization domain and phosphorylation at these sites is required to effect the disassembly of myosin filaments. In contrast to both these examples, Acanthoamoeba myosin II is phosphorylated in the dimerization domain but this modification is not necessary to enable myosin II monomers to dimerize in this species.

By far the most frequent example of post-translational modification is the addition of phosphate to polypeptides by specific enzymes known as protein kinases. These enzymes have been identified as important regulators of the state of phosphorylation of target proteins and have been implicated as major players in regulating cellular physiology. For example, the cell-division-cycle of the eukaryotic cell is primarily regulated by the state of phosphorylation of specific proteins, the functional state of which is determined by whether or not the protein is phosphorylated. This is determined by the relative activity of protein kinases which add phosphate and protein phosphatases which remove the phosphate moiety from these proteins. Clearly dysfunction of either the kinases or phosphatases may lead to a diseased state. This is best exemplified by the uncontrolled cellular division shown by tumor cells. The regulatory pathway is composed of a large number of genes that interact in vivo to regulate the phosphorylation cascade that ultimately determines if a cell is to divide or arrest cell division.

Currently there are several approaches to analysing the state of modification of target proteins in vivo:

1. In vivo incorporation of labeled (for example, radiolabeled) phosphate, which is added to target proteins. According to one common procedure, intracellular ATP pools are labeled with $^{32}PO_4$, which is subsequently incorporated into protein. Analysis of modified proteins is typically performed by electrophoresis and autoradiography, with specificity enhanced by immunoprecipitation of proteins of interest prior to electrophoresis.
2. Back-labeling. The incorporation of a labeled phosphate (e.g., $^{32}P$) into a protein in vitro to estimate the state of modification in vivo.
3. The use of cell-membrane-permeable protein kinase inhibitors (e.g., Wortmannin, staurosporine) to block phosphorylation of target proteins.
4. Western blotting, of either 1- or 2-dimensional gels bearing test protein samples, in which phosphorylation is detected using antibodies specific for phosphorylated forms of target proteins.
5. The exploitation of eukaryotic microbial systems to identify mutations in protein kinases and/or protein phosphatases.

These strategies have certain limitations. Monitoring states of phosphorylation by pulse or steady-state labeling is merely a descriptive strategy to show which proteins are phosphorylated when samples are separated by gel electrophoresis and visualized by autoradiography. This is unsatisfactory, due to the inability to identify many of the proteins that are phosphorylated. A degree of specificity is afforded to this technique if it is combined with immuno-precipitation; however, this is of course limited by the availability of antibodies to target proteins. Moreover, only highly-expressed proteins are readily detectable using this technique, which may fail to identify many low-abundance proteins, which are potentially important regulators of cellular functions.

The use of kinase inhibitors to block activity is also problematic. For example, very few kinase inhibitors have adequate specificity to allow for the unequivocal correlation of a given kinase with a specific kinase reaction. Indeed, many inhibitors have a broad inhibitory range. For example, staurosporine is a potent inhibitor of phospholipid/$Ca^{+2}$ dependant kinases. Wortmannin is some what more specific, being limited to the phosphatidylinositol-3 kinase family. This is clearly unsatisfactory because more than one biochemical pathway may be affected during treatment making the assignment of the effects almost impossible.

Monoclonal antibodies directed against phosphorylated epitopes, except in specific cases, exhibit a limitation of specificity comparable to that observed when in vivo labeling is undertaken. Immunological methods can only detect phosphorylated proteins globally (e.g., an anti-phosphotyrosine antibody will detect all tyrosine-phosphorylated proteins) and can only describe a steady state, rather provide a real-time assessment of protein:protein interactions. Such assays also require considerable manpower for processing.

Finally, yeast (*Saccharomyces cervisiae* and *Schizosaccharomyces pombe*) has been exploited as a model organism for the identification of gene function using recessive mutations. It is through research on the effects of these mutations that the functional specificities of many protein kinases have been elucidated. However, these molecular genetic techniques are not easily transferable to higher eukaryotes, which are diploid and therefore not as genetically tractable as these lower eukaryotes.

Recent research into the sites of protein phosphorylation has revealed a number of sequence specific motifs which, when phosphorylated or dephosphorylated, promote interaction with selected target proteins to either induce or inhibit activity of either the phosphorylated polypeptide or the target polypeptide.

For example, and not by way of limitation, many proteins involved in intracellular signal transduction have been shown to contain a domain comprising a sequence of approximately 100 amino acids; this sequence is termed the Src homology two (SH2) domain. SH2 domains bind target polypeptides that contain phosphorylated tyrosine. This binding is dependent on the primary amino acid sequence around the phosphotyrosine in the target protein and several peptide sequences which, when phosphorylated, bind to an SH2 domain have been identified (see e.g., Songyang et al., 1993, Cell, 72: 767–778). Non-limiting examples of such sequences include FLPVPEYINQSV, SEQ ID NO: 1, a sequence found in human ECF receptor, and AVGNPEYLNTVQ, SEQ ID NO:2, a sequence found in human EGF receptor, both of which are autophosphorylated growth factor receptors which stimulate the biochemical signaling pathways that control gene expression, cytoskeletal architecture and cell metabolism. Both of these sequences interact with SH2 domains found in the Sen-5 adapter protein.

The tumor suppressor protein p53, becomes activated by a transcription factor in response to DNA damage. A DNA-dependent protein kinase (DNA-PK) that is activated in response to breaks in DNA is thought to be regulator of p53 activity (Woo et al., 1998, Nature, 394: 700–704). The data described by Woo et al. indicate that the phosphorylation of p53 by DNA-PK serves a dual purpose insofar as phosphorylation promotes the binding of p53 to DNA and also prevents p53 inactivation by MDM2. A p53-derived peptide sequence EPPLSQEAFADLWKK, SEQ ID NO:3 is identified as the site of phosphorylation in p53 that (when phosphorylated) prevents the interaction of p53 with MIDM2.

An example of heterodimer association is described in patent application number WO92/00388. It describes an adenosine 3:5 cyclic monophosphate (cAMP) dependent protein kinase which is a four-subunit enzyme being composed of two catalytic polypeptides (C) and two regulatory polypeptides (R). In nature the polypeptides associate in a stoichiometry of $R_2C_2$. In the absence of cAMP the R and C subunits associate and the enzyme complex is inactive. In the presence of cAMP the R subunit functions as a ligand for cAMP resulting in dissociation of the complex and the release of active protein kinase. The invention described in WO92/00388 exploits this association by adding fluorochromes to the R and C subunits.

The polypeptides are labeled (or 'tagged') with fluorophores having different excitation/emission wavelengths. The excitation and emission of one such fluorophore effects a second excitation/emission event in the second fluorophore. By monitoring the fluorescence emission of each fluorophore, which reflects the presence or absence of fluorescence energy transfer between the two, it is possible to derive the concentration of cAMP as a function of the level of association between the R and C. Therefore, the natural affinity of the C subunit for the R subunit has been exploited to monitor the concentration of a specific metabolite, namely cAMP.

The prior art teaches that intact, fluorophore-labeled proteins can function as reporter molecules for monitoring the formation of multi-subunit complexes from protein monomers; however, in each case, the technique relies on the natural ability of the protein monomers to associate.

Tsien et al. (WO97/28261) teach that fluorescent proteins having the proper emission and excitation spectra that are brought into physically close proximity with one another can exhibit fluorescence resonance energy transfer ("FRET"). The invention of WO97/28261 takes advantage of that discovery to provide tandem fluorescent protein constructs in which two fluorescent protein labels capable of exhibiting FRET are coupled through a linker to form a tandem construct. In the assays of Tsien et al., protease activity is monitored using FRET to determine the distance between fluorophores controlled by a peptide linker and subsequent hydrolysis thereof. Other applications rely on a change in the intrinsic fluorescence of the protein as in the kinase assays of WO98/06737.

The present invention instead encompasses monitoring of the association of polypeptides, as described herein, which are labeled with fluorescent (protein and chemical) or other labels. FRET, a non-limiting example of a detection method of use in the invention, indicates the proximity of two labeled polypeptide binding partners, which labeled partners associate either in the presence or absence of post-translational addition/removal of a phosphate group to/from a natural binding domain present in at least one of the partners, but not into the fluorophore, reflecting the phosphorylation state of one or both of the binding partners and, consequently, the level of activity of a protein kinase or phosphatase.

There is a need in the art for efficient means of monitoring and/or modulating post-translational protein phosphorylation and/or dephosphorylation. Further, there is a need to develop a technique whereby the addition/removal of a phosphate group can be monitored continuously during real time to provide a dynamic assay system that also has the ability to resolve spatial information.

SUMMARY OF THE INVENTION

The invention provides natural binding domains, sequences and polypeptides, as well as kits comprising these molecules and assays of enzymatic function in which they are employed as reporter molecules. As used herein in reference to a polypeptide component of assays of the invention, the term "natural" refers both to the existence of such an amino acid sequence, whether contiguous or non-contiguous, in nature as well as to the phosphorylation-dependent binding of that component to a second polypeptide or binding partner, and does not relate to attributes of such a polypeptide other than such binding.

One aspect of the invention is an isolated natural binding domain and a binding partner therefor, wherein the isolated natural binding domain includes a site for post-translational phosphorylation and binds the binding partner in a manner dependent upon phosphorylation or dephosphorylation of the site.

The invention also provides a method for monitoring activity of an enzyme comprising performing a detection step to detect binding of an isolated natural binding domain and a binding partner therefor as a result of contacting one or both of the isolated natural binding domain and the binding partner with the enzyme, wherein the isolated natural binding domain includes a site for post-translational phosphorylation and binds the binding partner in a manner dependent upon phosphorylation of the site and wherein detection of binding of the isolated natural binding domain and the binding partner as a result of the contacting is indicative of enzyme activity.

An enzyme to be assayed according to the invention is a protein kinase or a phosphatase.

The invention additionally encompasses a method for monitoring activity of an enzyme comprising performing a detection step to detect dissociation of an isolated natural binding domain from a binding partner therefor as a result of contacting one or both of the isolated natural binding domain and the binding partner with the enzyme, wherein the isolated natural binding domain includes a site for post-translational phosphorylation and binds the binding partner in a manner dependent upon phosphorylation of the site and wherein detection of dissociation of the isolated natural binding domain from the binding partner as a result of the contacting is indicative of enzyme activity.

As used herein, the term "binding domain" in a three-dimensional sense refers to the amino acid residues of a first polypeptide required for phosphorylation-dependent binding between the first polypeptide and its binding partner. The amino acids of a "binding domain" may be either contiguous or non-contiguous and may form a binding pocket for phosphorylation-dependent binding. A domain must include at least 1 amino acid, but may include 2 or more amino acids, preferably at least 4 amino acids, which are contiguous or non-contiguous, but are necessary for phosphorylation-dependent binding to the binding partner. A binding domain will not include a natural full-length polypeptide, but will include a subset of the amino acids of a full-length polypeptide, wherein the subset may include a number of amino acids as high as one fewer than the length of a given natural full-length polypeptide.

A binding domain which is of use in the invention is a "natural binding domain" (i.e., a binding domain that exhibits phosphorylation-dependent binding to a binding partner in nature). A natural binding domain of use in the invention may be isolated or may be present in the context of a larger polypeptide molecule (i.e., one which comprises amino acids other than those of the natural binding domain), which molecule may be either naturally-occurring or recombinant and, in the case of the latter, may comprise either natural or non-natural amino acid sequences outside the binding domain.

As used herein with regard to phosphorylation or dephosphorylation of a polypeptide, the term "site" refers to an amino acid or amino acid sequence of a natural binding domain or a binding partner which is recognized by (i.e., a signal for) a kinase or phosphatase for the purpose of phosphorylation or dephosphorylation (i.e., addition or removal of a phosphate moiety) of the polypeptide or a portion thereof. A "site" additionally refers to the single amino acid which is phosphorylated or dephosphorylated. It is contemplated that a site comprises a small number of amino acids, as few as one but typically from 2 to 10, less often up to 30 amino acids, and further that a site comprises fewer than the total number of amino acids present in the polypeptide.

In an enzymatic assay of the invention, a "site", for post-translational phosphorylation or dephosphorylation may be present on either or both of the isolated natural binding domain or the binding partner therefor. If such sites are present on both the isolated natural binding domain and its binding partner, binding between the natural binding domain and the binding partner, or between two natural binding domains, may be dependent upon the phosphorylation or dephosphorylation state of either one or both sites. If a single polypeptide chain comprises the natural binding domain and the binding partner (or two natural binding domains), the state of phosphorylation or dephosphorylation of one or both sites will determine whether binding occurs.

A site suitable for addition or removal of a phosphate moiety is present within an isolated natural binding domain or binding partner thereof of the invention at a position such that formation of a complex between the isolated natural binding domain and its binding partner is dependent upon the presence or absence of the phosphate moiety; and preferably does not overlap with an amino acid which is part of a fluorescent tag or other detectable label (including, but not limited to, a radioactive label) or quencher.

Similarly, the amino acid that includes a phosphate moiety may be positioned anywhere within the isolated natural binding domain such that binding of the isolated natural binding domain and its binding partner is dependent upon the presence or absence of the phosphate moiety.

As used herein, "phosphorylation" and "dephosphorylation" refer to the addition or removal of a phosphate moiety to/from a polypeptide, respectively. As used herein, the term "post-translational modification" refers to the addition or removal of a phosphate moiety and does not refer to other post-translational events which do not involve addition or removal of a phosphate moiety, and thus does not include simple cleavage of the reporter molecule polypeptide backbone by hydrolysis of a peptide bond.

As used herein, the term "moiety" refers to a post-translationally added or removed phosphate ($PO_4$) group; the terms "moiety" and "group" are used interchangeably.

As used herein, the term "binding partner" refers to a polypeptide or fragment thereof (a peptide) that binds to a binding domain, sequence or polypeptide, as defined herein, in a manner which is dependent upon the state of phosphorylation of a site for phosphorylation or dephosphorylation which is, at a minimum, present upon the binding domain, sequence or polypeptide; the binding partner itself may, optionally, comprise such a site and binding between the binding domain, fragment or polypeptide with its corresponding binding partner may, optionally, depend upon modification of that site. A binding partner does not necessarily have to contain a site for phosphorylation or dephosphorylation if such an site is not required to be present on it for modification-dependent association between it and a binding domain, sequence or polypeptide. Binding partners of use in the invention are those which are found in nature and exhibit natural phosphorylation-dependent binding to a natural binding domain, sequence or polypeptide of the invention as defined herein. In one embodiment of the invention, a binding partner is shorter (i.e., by at least one N-terminal or C-terminal amino acid) than the natural full-length polypeptide.

As used herein, the term "associates" or "binds" refers to a natural binding domain as described herein and its binding partner, having a binding constant sufficiently strong to allow detection of binding by FRET or other detection means, which are in physical contact with each other and have a dissociation constant (Kd) of about 10 $\mu$M or lower. The contact region may include all or parts of the two molecules. Therefore, the terms "substantially dissociated" and "dissociated" or "substantially unbound" or "unbound"

refer to the absence or loss of contact between such regions, such that the binding constant is reduced by an amount which produces a discernable change in a signal compared to the bound state, including a total absence or loss of contact, such that the proteins are completely separated, as well as a partial absence or loss of contact, so that the body of the proteins are no longer in close proximity to each other but may still be tethered together or otherwise loosely attached, and thus have a dissociation constant greater than 10 $\mu$M (Kd). In many cases, the Kd will be in the mM range. The terms "complex", "dimer", "multimer" and "oligomer" as used herein, refer to the natural binding domain and its binding partner in the associated or bound state. More than one molecule of each of the two or more proteins may be present in a complex, dimer, multimer or oligomer according to the methods of the invention.

As used herein in reference to a natural binding domain or other polypeptide, the term "isolated" refers to a molecule or population of molecules that is substantially pure (i.e., free of contaminating molecules of unlike amino acid sequence).

As used herein in reference to the purity of a molecule or population thereof, the term "substantially" refers to that which is at least 50%, preferably 60–75%, more Jo preferably from 80–95% and, most preferably, from 98–100% pure.

"Naturally-occurring" as used herein, as applied to a polypeptide or polynucleotide, refers to the fact that the polypeptide or polynucleotide can be found in nature. One such example is a polypeptide or polynucleotide sequence that is present in an organism (including a virus) that can be isolated form a source in nature.

The term "synthetic", as used herein, is defined as any amino- or nucleic acid sequence which is produced via chemical synthesis.

In an assay of the invention, post-translational phosphorylation is reversible, such that repeating cycles of addition and removal of a phosphate moiety may be observed, although such cycles may not occur in a living cell found in nature.

An advantage of assays of the invention is that they may, if desired, be performed in "real time". As used herein in reference to monitoring, measurements or observations in assays of the invention, the term "real time" refers to that which is performed contemporaneously with the monitored, measured or observed events and which yields a result of the monitoring, measurement or observation to one who performs it simultaneously, or effectively so, with the occurrence of a monitored, measured or observed event. Thus, a "real time" assay or measurement contains not only the measured and quantitated result, such as fluorescence, but expresses this in real time, that is, in hours, minutes, seconds, milliseconds, nanoseconds, picoseconds, etc. Shorter times exceed the instrumentation capability; further, resolution is also limited by the folding and binding kinetics of polypeptides.

As used herein, the term "binding sequence" refers to that portion of a polypeptide comprising at least 1, preferably at least 2, more preferably at least 4, and up to 8, 10, 100 or even 1000 contiguous (i.e., covalently linked by peptide bonds) amino acid residues, that are sufficient for phosphorylation-dependent binding to a binding partner. A binding sequence will not include a natural full-length polypeptide, but will include a subset of the amino acids of a full-length polypeptide, wherein the subset may include a number of amino acids as high as one fewer than the length of a given natural full-length polypeptide.

As used herein in reference to those binding sequences that are of use in the invention, the term "natural binding sequence" refers to a binding sequence, as defined above, which consists of an amino acid sequence which is found in nature and which is naturally dependent upon the phosphorylation state of a site for post-translational phosphorylation found within it for binding to a binding partner. A "natural binding sequence" may be present either in isolation or in the context of a larger polypeptide molecule, which molecule may be naturally-occurring or recombinant. If present, amino acids outside of the binding sequence may be either natural, i.e., from the same polypeptide sequence from which the fragment is derived, or non-natural, i.e., from another (different) polypeptide or from a sequence that is not derived from any known polypeptide. In assays of the invention, a binding sequence and its binding partner may exist either on two different polypeptide chains or on a single polypeptide chain.

As used herein, the term "binding polypeptide" refers to a molecule comprising multiple binding sequences, as defined above. A binding polypeptide of use in the invention is a "natural binding polypeptide", in which the component binding sequences are natural binding sequences, as defined above (e.g., wherein the binding sequences are derived from a single, naturally-occurring polypeptide molecule), and are both necessary and, in combination, sufficient to permit phosphorylation state-dependent binding of the binding polypeptide to its binding partner, wherein the sequences of the binding polypeptide are either contiguous or are non-contiguous. As used herein in reference to the component binding sequences of a binding polypeptide, the term "non-contiguous" refers to binding sequences which are linked by intervening naturally-occurring, as defined herein, or non-natural amino acid sequences or other chemical or biological linker molecules such are known in the art. The amino acids of a polypeptide that do not significantly contribute to the natural phosphorylation-state-dependent binding of that polypeptide to its binding partner may be those amino acids which are naturally present and link the binding sequences in a binding polypeptide or they may be derived from a different natural polypeptide or may be wholly unknown in nature. In assays of the invention, a binding polypeptide and its binding partner (which may, itself, be a binding domain, sequence or polypeptide, as defined herein) may exist on two different polypeptide chains or on a single polypeptide chain. According to the invention, a natural binding polypeptide, like a polypeptide as defined above, is not a full-length natural polypeptide chain, but instead comprises a subset that encompasses up to one fewer than the total number of amino acids in a natural polypeptide chain.

As used herein, the terms "polypeptide" and "peptide" refer to a polymer in which the monomers are amino acids and are joined together through peptide or disulfide bonds. The terms subunit and domain also may refer to polypeptides and peptides having biological function. A peptide useful in the invention will at least have a binding capability, i.e, with respect to binding as- or to a binding partner, and also may have another biological function that is a biological function of a protein or domain from which the peptide sequence is derived. "Polypeptide" refers to a naturally-occurring amino acid chain comprising a subset of the amino acids of a full-length protein, wherein the subset comprises at least one fewer amino acid than does the full-length protein, or a "fragment thereof" or "peptide", such as a selected region of the polypeptide that is of interest in a binding assay and for which a binding partner is known or determinable. "Fragment thereof" thus refers to an amino acid sequence that is a portion of a full-length polypeptide, between about 8 and about 1000 amino acids in length, preferably about 8 to about 300, more preferably about 8 to about 200 amino acids, and even more preferably about 10 to about 50 or 100 amino acids in length. "Peptide" refers to a short amino acid sequence that is 10–40 amino acids long, preferably 10–35 amino acids. Additionally, unnatural amino acids, for example, β-alanine, phenyl glycine and homoarginine may be included. Commonly-encountered amino acids which are not gene-encoded may also be used in the present invention. All of the amino acids used in the present invention may be either the D- or L- optical isomer. The L-isomers are preferred. In addition, other peptidomimetics are also useful, e.g. in linker sequences of polypeptides of the present invention (see Spatola, 1983, in *Chemistry and Biochemistry of Amino Acids, Peptides and Proteins*, Weinstein, ed., Marcel Dekker, New York, p. 267).

As used herein, the terms "protein", "subunit" and "domain" refer to a linear sequence of amino acids which exhibits biological function. This linear sequence does not include full-length amino acid sequences (e.g. those encoded by a full-length gene or polynucleotide), but does include a portion or fragment thereof, provided the biological function is maintained by that portion or fragment. The terms "subunit" and "domain" also may refer to polypeptides and peptides having biological function. A peptide useful in the invention will at least have a binding capability, i.e, with respect to binding as or to a binding partner, and also may have another biological function that is a biological function of a protein or domain from which the peptide sequence is derived. "Polynucleotide" refers to a polymeric form of nucleotides of at least 10 bases in length and up to 1,000 bases or even more, either ribonucleotides or deoxyribonucleotides or a modified form of either type of nucleotide. The term includes single and double stranded forms of DNA.

Preferably, with regard to the natural binding domain and/or binding partner therefor, phosphorylation or dephosphorylation is performed by an enzyme which is a kinase or a phosphatase, respectively.

It is preferred that phosphorylation of the site prevents binding of the isolated natural binding domain to the binding partner.

As used herein, the term "prevents" refers to a reduction of at least 10%, preferably 20–40%, more preferably 50–75% and, most preferably, 80–100% of binding of the isolated natural binding domain to the binding partner therefor.

Preferably, phosphorylation of the site promotes binding of the isolated natural binding domain to the binding partner.

As used herein with regard to protein:protein binding, the term "promotes" refers to that which causes an increase in binding of the natural binding domain and its binding partner of at least two-fold, preferably 10- to 20-fold, highly preferably 50- to 100-fold, more preferably from 200- to 1000-fold, and, most preferably, from 200 to 10,000-fold.

It is preferred that dephosphorylation of the site prevents binding of the isolated natural binding domain to the binding partner.

It is additionally preferred that dephosphorylation of the site promotes binding of the isolated natural binding domain to the binding partner.

In a preferred embodiment, at least one of the isolated natural binding domain and the binding partner comprises a detectable label.

Preferably, the detectable label emits light.

More preferably, the light is fluorescent.

It is preferred that one of the isolated natural binding domain and the binding partner therefor comprises a quencher for the detectable label. Labels of use in the invention include, but are not limited to, a radioactive label, a fluorescent label and a quencher for either.

A "fluorescent label", "fluorescent tag" or "fluorescent group" refers to either a fluorophore or a fluorescent protein or fluorescent fragment thereof. "Fluorescent protein" refers to any protein which fluoresces when excited with appropriate electromagnetic radiation. This includes a protein whose amino acid sequence is either natural or engineered. A "fluorescent protein" is a full-length fluorescent protein or fluorescent fragment thereof. By the same token, the term "linker" refers to that which is coupled to both the donor and acceptor protein molecules, such as an amino acid sequence joining two natural binding domains or a disulfide bond between two polypeptides.

It is contemplated that with regard to fluorescent labels employed in FRET, the reporter labels are chosen such that the emission wavelength spectrum of one (the "donor") is within the excitation wavelength spectrum of the other (the "acceptor"). With regard to a fluorescent label and a quencher employed in a single-label detection procedure in an assay of the invention, it is additionally contemplated that the fluorophore and quencher are chosen such that the emission wavelength spectrum of the fluorophore is within the absorption spectrum of the quencher, such that when the fluorophore and the quencher with which it is employed are brought into close proximity by binding of the natural binding domain, sequence or polypeptide upon which one is present with the binding partner comprising the other, detection of the fluorescent signal emitted by the fluorophore is reduced by at least 10%, preferably 20–50%, more preferably 70–90% and, most preferably, by 95–100%. A typical quencher reduces detection of a fluorescent signal by approximately 80%.

Another aspect of the invention is a kit comprising an isolated natural binding domain and a binding partner therefor, wherein the isolated natural binding domain includes a site for post-translational phosphorylation and binds the binding partner in a manner dependent upon phosphorylation of the site, and packaging material therefor.

It is preferred that the kit further comprises a buffer which permits phosphorylation-dependent binding of the isolated natural binding domain and the binding partner.

As used herein, the term "buffer" refers to a medium which permits activity of the protein kinase or phosphatase used in an assay of the invention, and is typically a low-ionic-strength buffer or other biocompatible solution (e.g., water, containing one or more of physiological salt, such as simple saline, and/or a weak buffer, such as Tris or phosphate, or others as described hereinbelow), a cell culture medium, of which many are known in the art, or a whole or fractionated cell lysate. Such a buffer permits phosphorylation-dependent binding of a natural binding domain of the invention and a binding partner therefor and, preferably, inhibits degradation and maintains biological activity of the reaction components. Inhibitors of degradation, such as protease inhibitors (e.g., pepstatin, leupeptin, etc.) and nuclease inhibitors (e.g., DEPC) are well known in the art. Lastly, an appropriate buffer may comprise a stabilizing substance such as glycerol, sucrose or polyethylene glycol.

As used herein, the term "physiological buffer" refers to a liquid medium that mimics the salt balance and pH of the cytoplasm of a cell or of the extracellular milieu, such that post-translational protein modification reactions and protein:protein binding are permitted to occur in the buffer as they would in vivo.

Preferably, the buffer permits phosphorylation or dephosphorylation of the site by a kinase or a phosphatase, respectively.

In a preferred embodiment, the kit further comprises one or both of a kinase and a phosphatase.

It is preferred that the kit further comprises a substrate for the phosphatase or kinase, the substrate being MgATP.

It is contemplated that at least a part of a substrate of an enzyme of use in an assay of the invention is transferred to a phosphorylation site on an isolated polypeptide of the invention. As used herein, the term "at least a part of a substrate" refers to a portion (e.g., a moiety or a group, as defined above) which comprises less than the whole of the substrate for the enzyme, the transfer of which portion to a phosphorylation site on an isolated polypeptide, both as defined above, is catalyzed by the enzyme.

It is additionally preferred that the kit further comprises a cofactor for one or both of the kinase or phosphatase. Cofactors of use in the invention include, but are not limited to, cAMP, phosphotidylserine, diolein, $Mn^{2+}$ and $Mg^{2+}$.

Preferably, at least one of the isolated natural binding domain and the binding partnercomprises a detectable label.

It is preferred that the detectable label emits light, and more preferred that the light is fluorescent.

An enzyme (e.g., a protein kinase or phosphatase) of use in the invention may be natural or recombinant or, alternatively, may be chemically synthesized. If either natural or recombinant, it may be substantially pure (i.e., present in a population of molecules in which it is at least 50% homogeneous), partially purified (i.e., represented by at least 1% of the molecules present in a fraction of a cellular lysate) or may be present in a crude biological sample.

As used herein, the term "sample" refers to a collection of inorganic, organic or biochemical molecules which is either found in nature (e.g., in a biological- or other specimen) or in an artificially-constructed grouping, such as agents which might be found and/or mixed in a laboratory. Such a sample may be either heterogeneous or homogeneous.

As used herein, the interchangeable terms "biological specimen" and "biological sample" refer to a whole organism or a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). "Biological sample" further refers to a homogenate, lysate or extract prepared from a whole organism or a subset of its tissues, cells or component parts, or a fraction or portion thereof. Lastly, "biological sample" refers to a medium, such as a nutrient broth or gel in which an organism has been propagated, which contains cellular components, such as proteins or nucleic acid molecules.

As used herein, the term "organism" refers to all cellular life-forms, such as prokaryotes and eukaryotes, as well as non-cellular, nucleic acid-containing entities, such as bacteriophage and viruses.

In a method as described above, it is preferred that at least one of the isolated natural binding domain and the binding partner is labeled with a detectable label.

Preferably, the label emits light and, more preferably, the light is fluorescent.

In another preferred embodiment, the detection step is to detect a change in signal emission by the detectable label.

It is preferred that the method further comprises exciting the detectable label and monitoring fluorescence emission.

It is additionally preferred that the method further comprises the step, prior to or after the detection step, of contacting the isolated natural binding domain and the binding partner with an agent which modulates the activity of the enzyme.

As used herein with regard to a biological or chemical agent, the term "modulate" refers to enhancing or inhibiting the activity of a protein kinase or phosphatase in an assay of the invention; such modulation may be direct (e.g. including, but not limited to, cleavage of- or competitive binding of another substance to the enzyme) or indirect (e.g. by blocking the initial production or, if required, activation of the kinase or phosphatase). "Modulation" refers to the capacity to either increase or decease a measurable functional property of biological activity or process (e.g., enzyme activity or receptor binding) by at least 10%, 15%, 20%, 25%, 50%, 100% or more; such increase or decrease may be contingent on the occurrence of a specific event, such as activation of a signal transduction pathway, and/or may be manifest only in particular cell types.

The term "modulator" refers to a chemical compound (naturally occurring or non-naturally occurring), such as a biological macromolecule (e.g., nucleic acid, protein, non-peptide, or organic molecule), or an extract made from biological materials such as bacteria, plants, fungi, or animal (particularly mammalian) cells or tissues, or even an inorganic element or molecule. Modulators are evaluated for potential activity as inhibitors or activators (directly or indirectly) of a biological process or processes (e.g., agonist, partial antagonist, partial agonist, antagonist, antineoplastic agents, cytotoxic agents, inhibitors of neoplastic transformation or cell proliferation, cell proliferation-promoting agents, and the like) by inclusion in screening assays described herein. The activities (or activity) of a modulator may be known, unknown or partially-known. Such modulators can be screened using the methods described herein.

The term "candidate modulator" refers to a compound to be tested by one or more screening method(s) of the invention as a putative modulator. Usually, various predetermined concentrations are used for screening such as 0.01 $\mu M$, 0.1 $\mu M$, 1.0 $\mu M$, and 10.0 $\mu M$, as described more fully hereinbelow. Test compound controls can include the measurement of a signal in the absence of the test compound or comparison to a compound known to modulate the target.

The invention additionally provides a method of screening for a candidate modulator of enzymatic activity of a kinase or a phosphatase, the method comprising contacting an isolated natural binding domain, a binding partner therefor and an enzyme with a candidate modulator of the kinase or phosphatase, wherein the natural binding domain includes a site for post-translational phosphorylation and binds the binding partner in a manner that is dependent upon phosphorylation or dephosphorylation of the site by the kinase or phosphatase and wherein at least one of the isolated natural binding domain and the binding partner comprises a detectable label, and monitoring the binding of the isolated natural binding domain to the binding partner, wherein binding or dissociation of the isolated natural binding domain and the binding partner as a result of the contacting is indicative of modulation of enzymatic activity by the candidate modulator of the kinase or phosphatase.

Preferably, the detectable label emits light.

More preferably, the light is fluorescent.

It is preferred that the monitoring comprises measuring a change in energy transfer between a detectable label present on the isolated natural binding domain and a detectable label present on the binding partner.

A final aspect of the invention is a method of screening for a candidate modulator of enzymatic activity of a kinase or a phosphatase, the method comprising contacting an assay system with a candidate modulator of enzymatic activity of a kinase or phosphatase, and monitoring binding of an isolated natural binding domain and a binding partner therefor in the assay system, wherein the isolated natural binding domain includes a site for post-translational phosphorylation and binds the binding partner in a manner that is dependent upon phosphorylation or dephosphorylation of the site by a kinase or phosphatase in the assay system, wherein at least one of the isolated natural binding domain and the binding partner comprises a detectable label, and wherein binding or dissociation of the isolated natural binding domain and the binding partner as a result of the contacting is indicative of modulation of enzymatic activity by the candidate modulator of a the kinase or phosphatase.

It is highly preferred that in any of the above methods, the method comprises real-time observation of association of an isolated natural binding domain and its binding partner.

Further features and advantages of the invention will become more fully apparent in the following description of the embodiments and drawings thereof, and from the claims.

BRIEF DESCRIPTIONS OF THE DRAWINGS

FIG. 1 diagrams double- and single-chain enzymatic assay formats of the invention.

Figure 2:
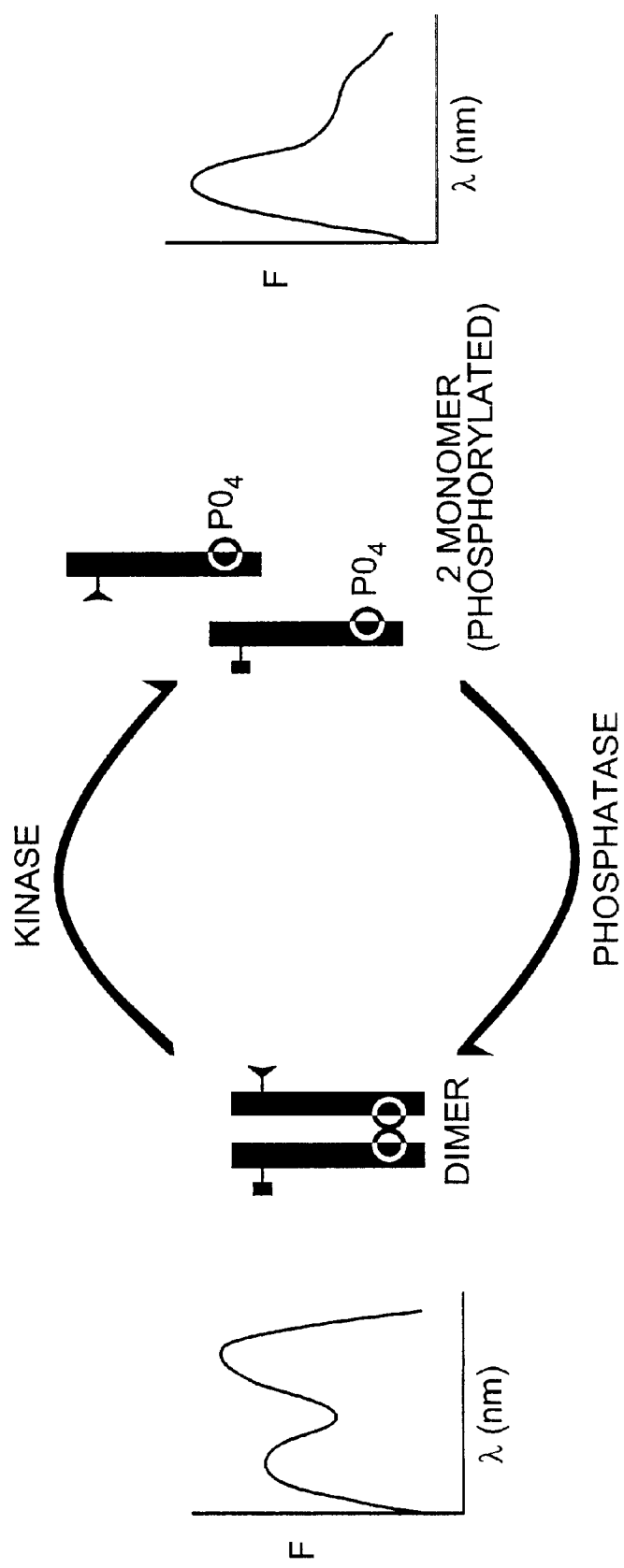

FIG. 2 presents a schematic overview of FRET in an assay of the invention.

Figure 3:
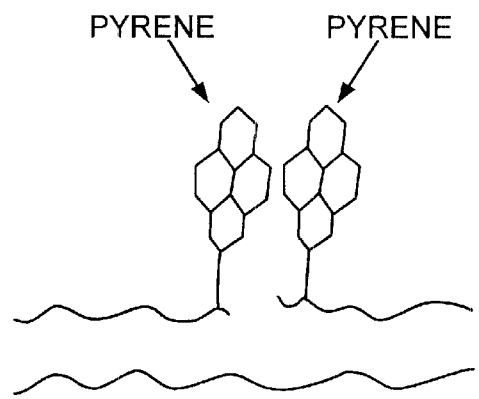

FIG. 3 presents monomer:excimer fluorescence.

Figure 4:
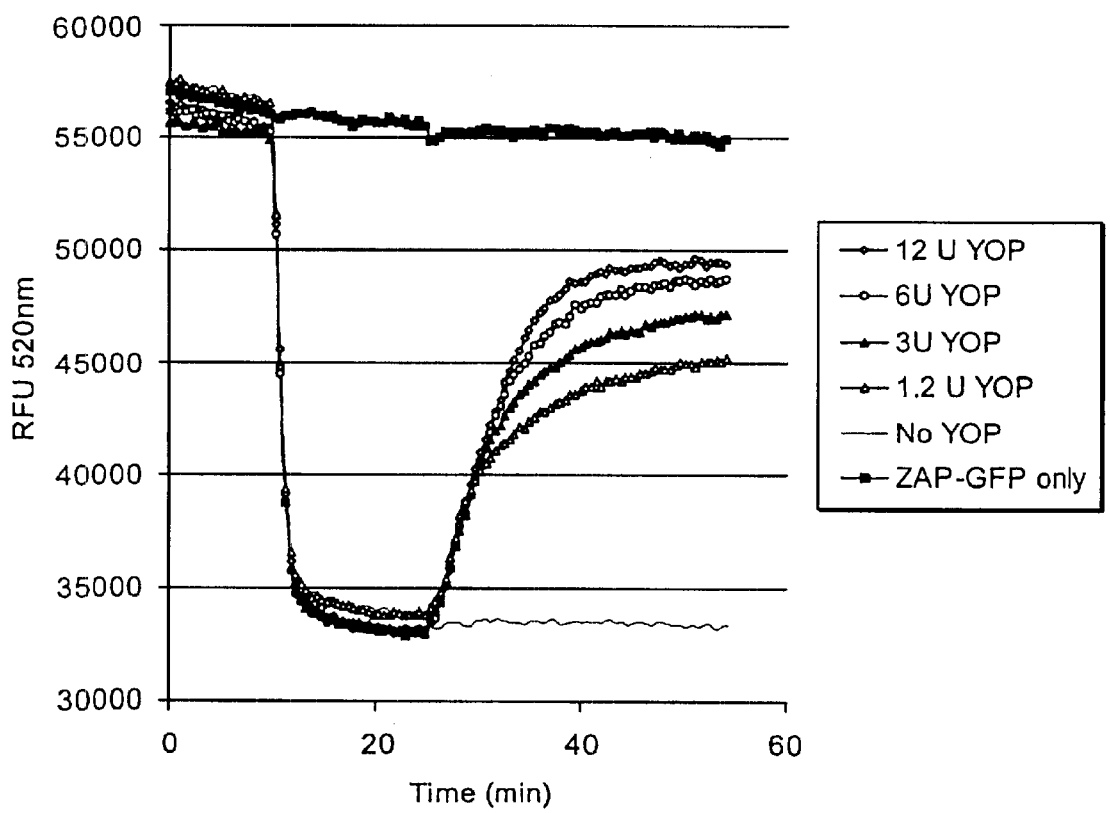

FIG. 4 demonstrates the results of FRET between ZAP70-GFP and a rhodamine labelled TCRζ derived peptide.

Figure 5:
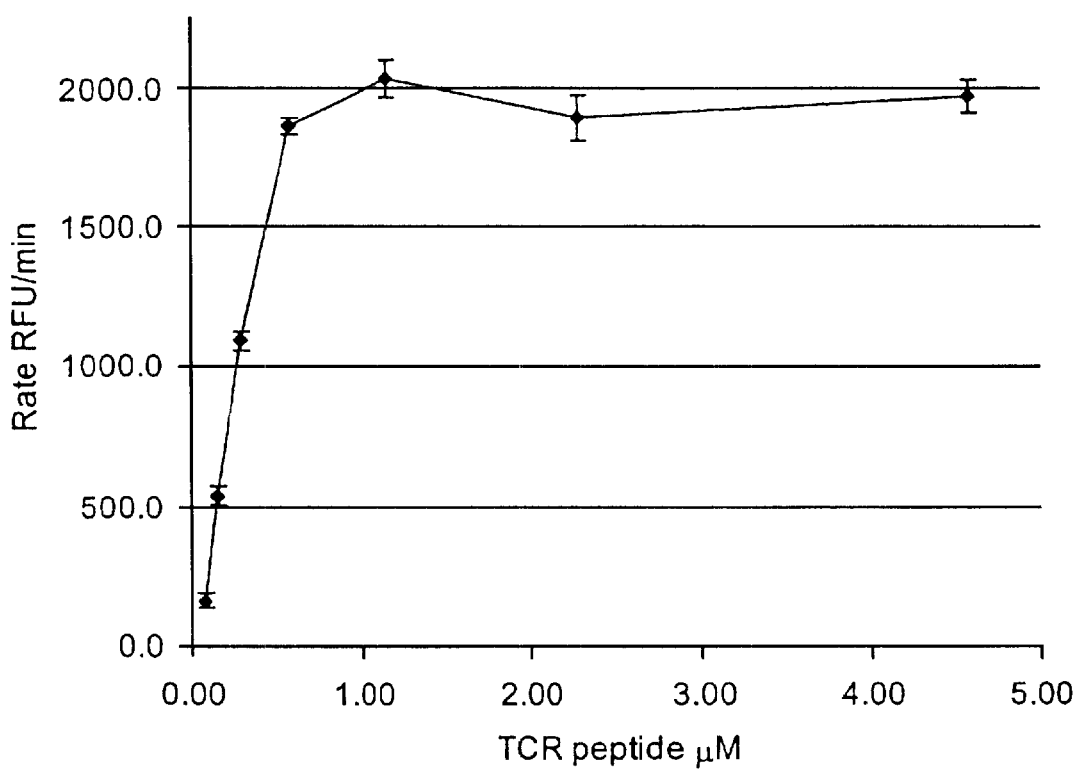

FIG. 5 demonstrates the dependence of YOP activity on different concentrations of TCRζ peptide.

Figure 6:
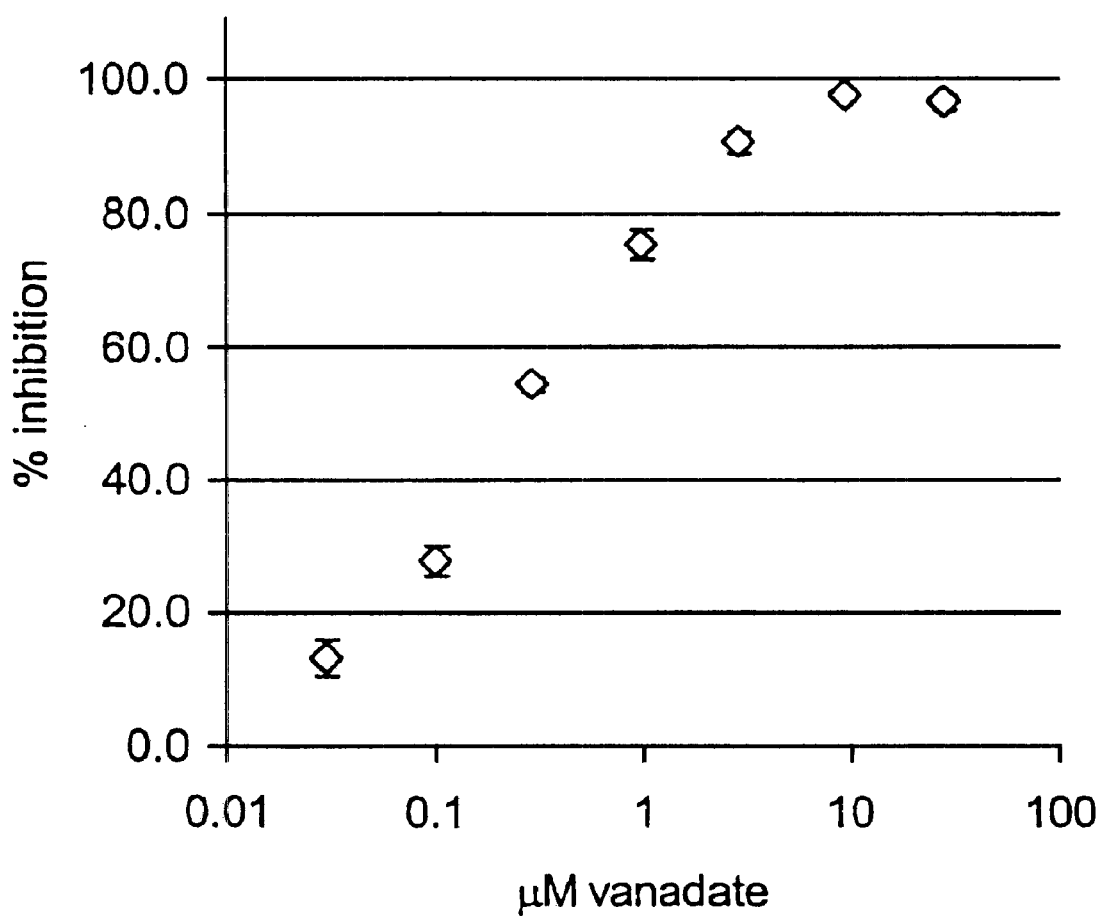

FIG. 6 presents the results of a FRET based assay for measuring inhibition of YOP by sodium orthovanadate.

Figure 7:
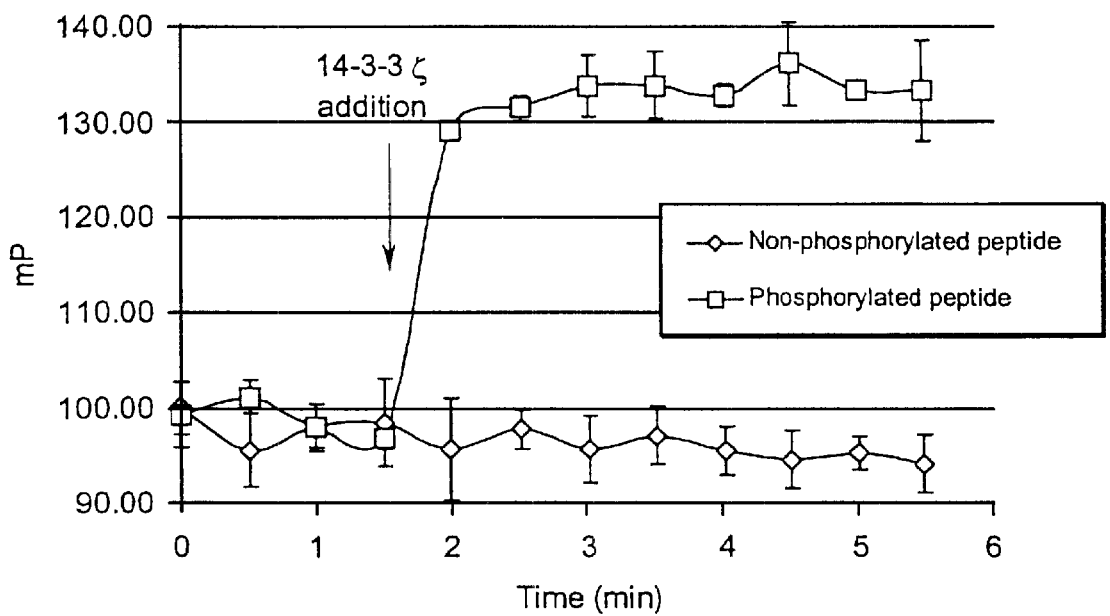

FIG. 7 demonstrates detection of binding of Chk1 phosphorylated, fluorescein labelled Chktide to 14-3-3ζ by fluorescence polarisation.

Figure 8:
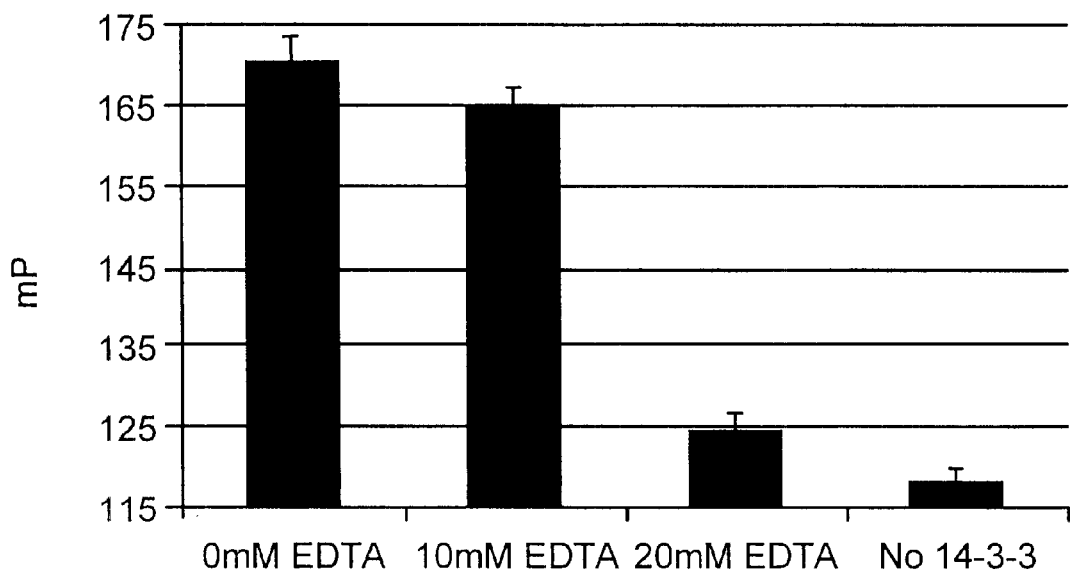

FIG. 8 demonstrates inhibition of Chk1 phosphorylation of Chktide peptide by EDTA.

Figure 9:
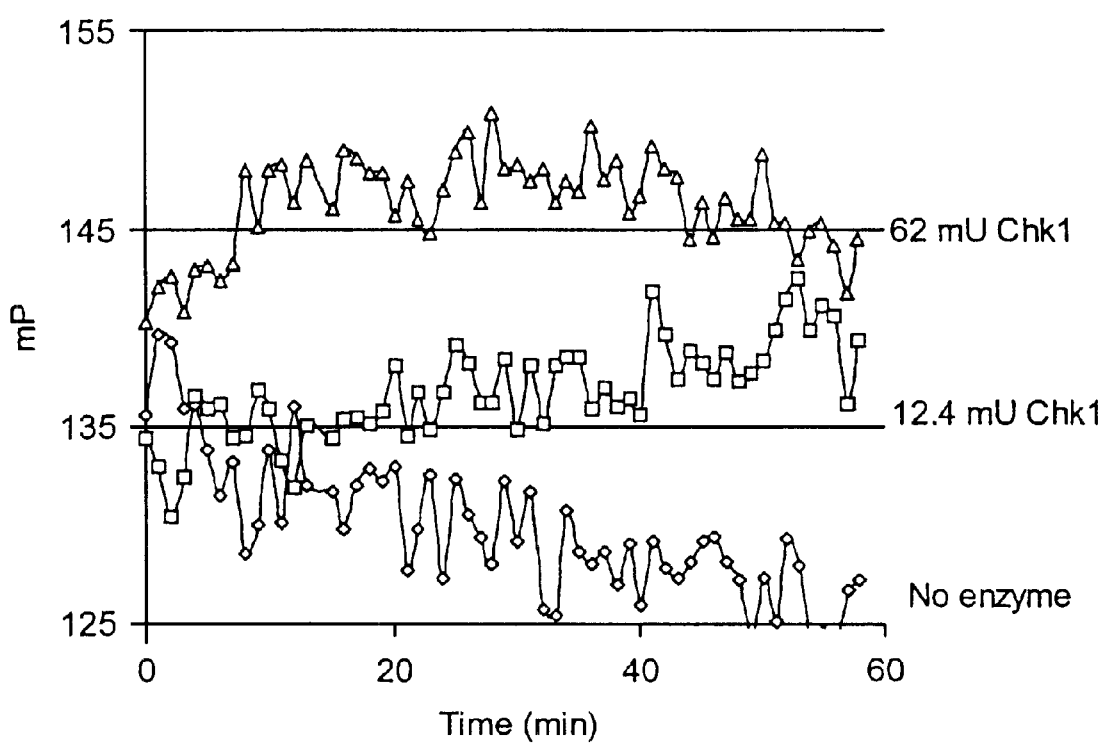

FIG. 9 presents the results of a real time assay for Chk1 activity monitoring the fluorescence polarisation of fluorescein labelled Chktide substrate binding to 14-3-3ζ protein.

Figure 10:
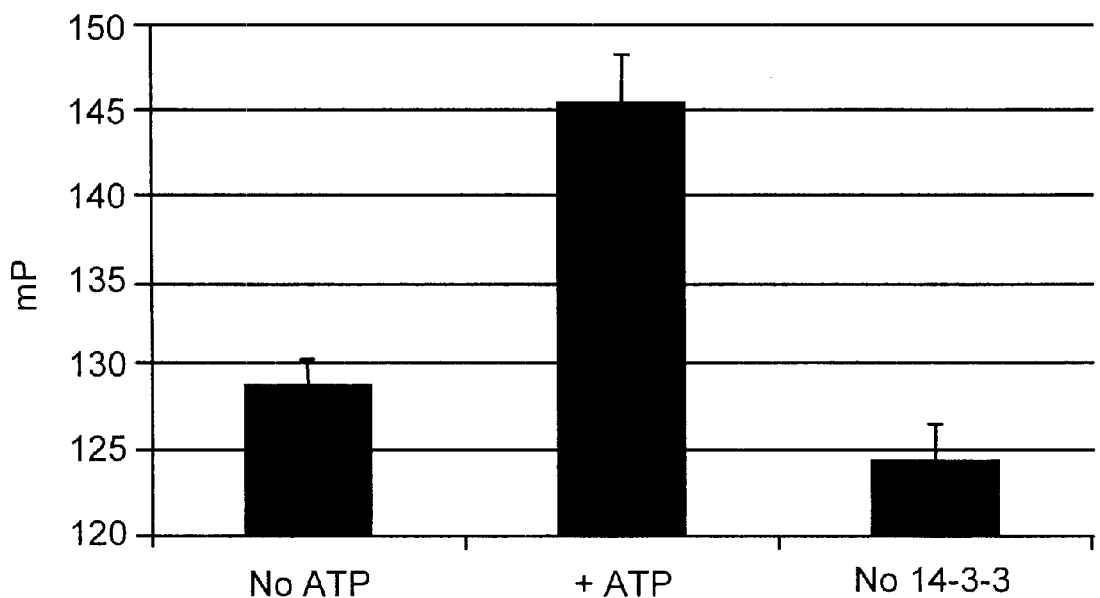

FIG. 10 demonstrates that Chk1 activity measured by Chktide:14-3-3 binding is dependent on ATP and the presence of 14-3-3ζ protein.

Figure 11:
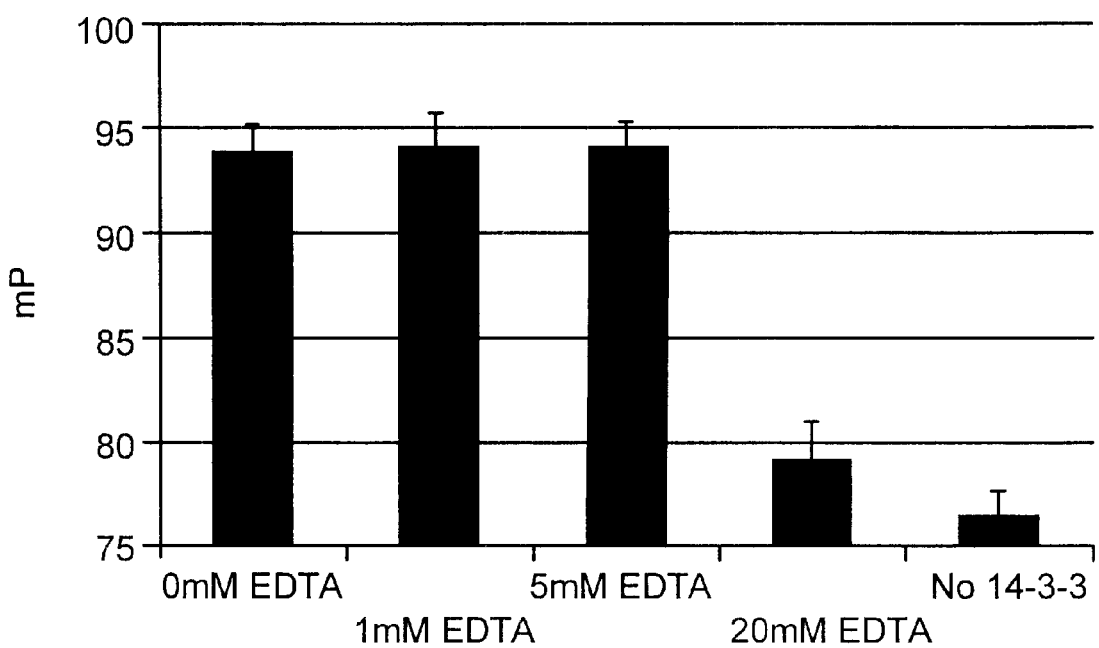

FIG. 11 demonstrates inhibition of Chk1 phosphorylation of fluorescein labelled Chktide by EDTA.

Figure 12:
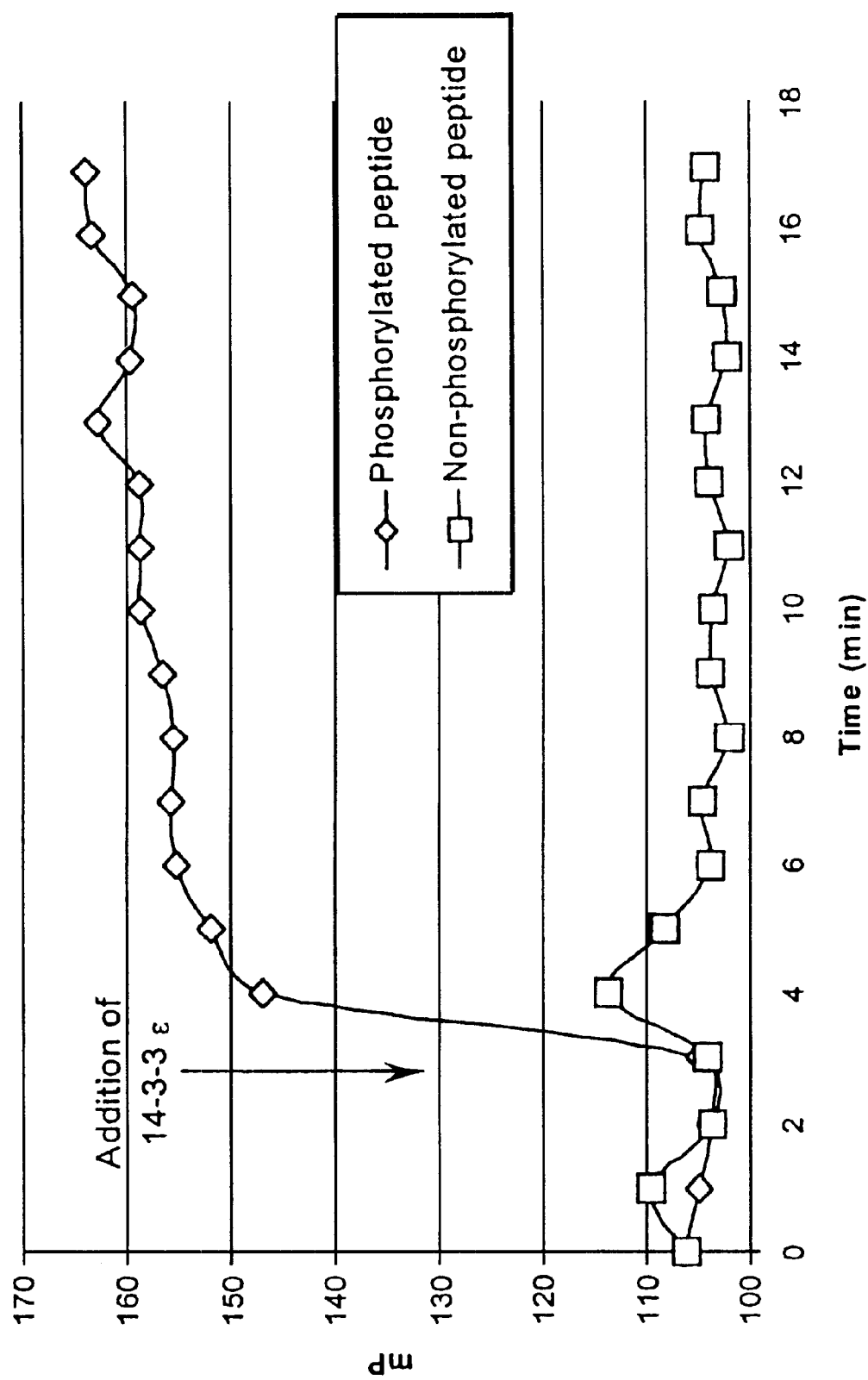

FIG. 12 presents the results of an assay for Chk1 phosphorylation of Chktide peptide as measured by 14-3-3ε binding.

Figure 13:
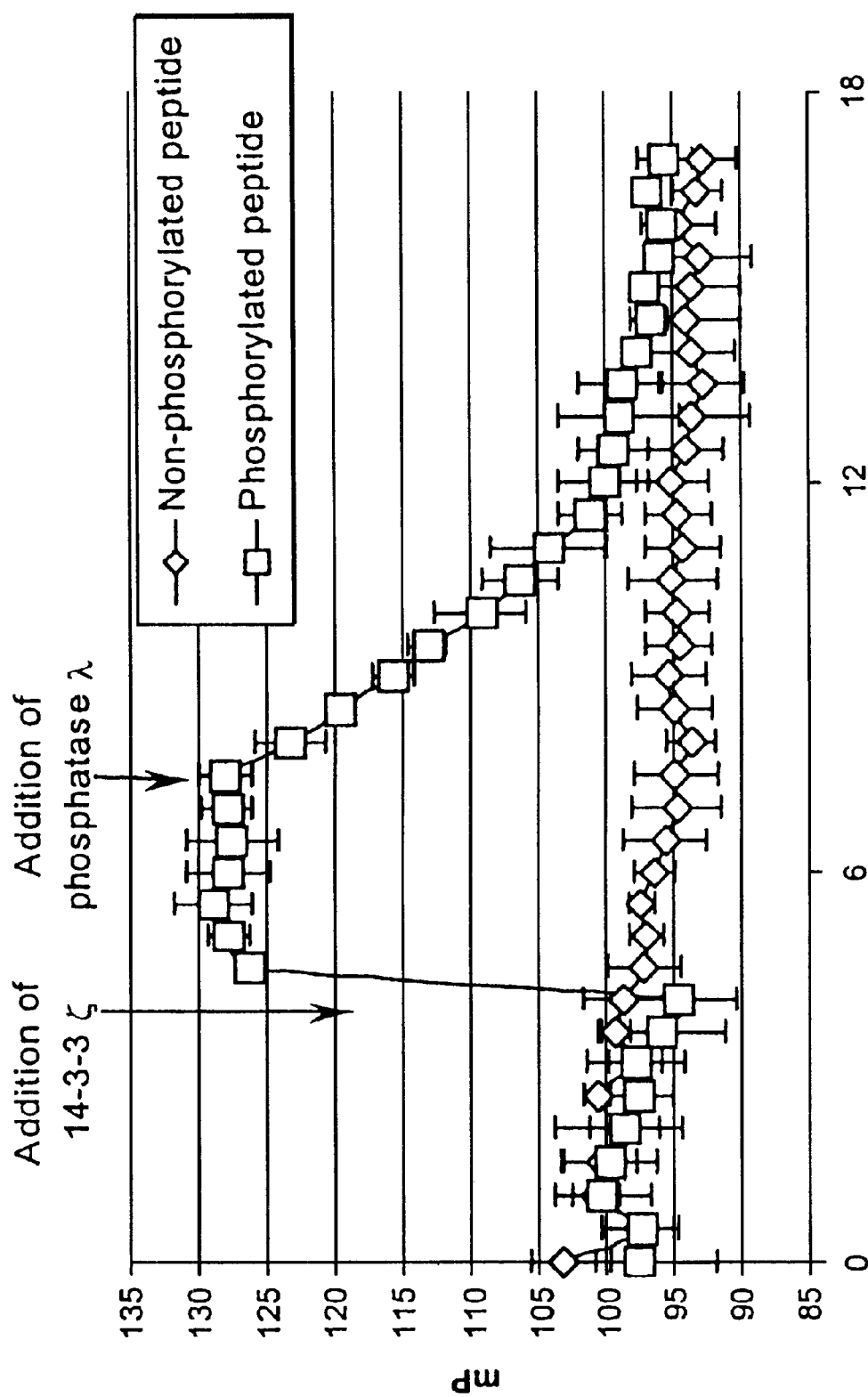

FIG. 13 demonstrates phosphatase λ activity as measured by dephosphorylation of fluorescein labelled Chktide and decreased binding to 14-3-3ζ.

Figure 14:
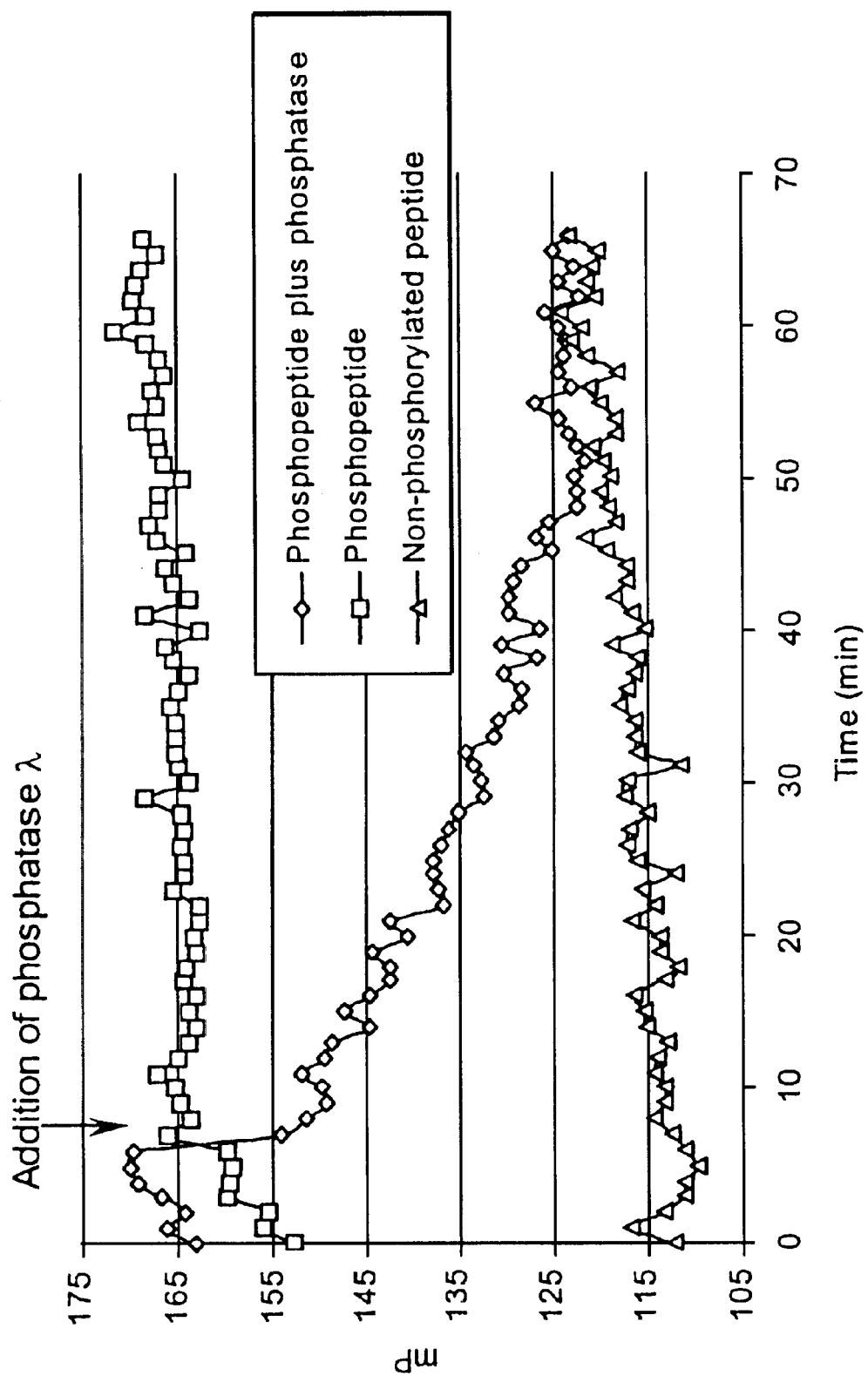

FIG. 14 demonstrates phosphatase λ activity as measured by dephosphorylation of fluorescein labelled Chktide and decreased binding to 14-3-3ε.

Figure 15:
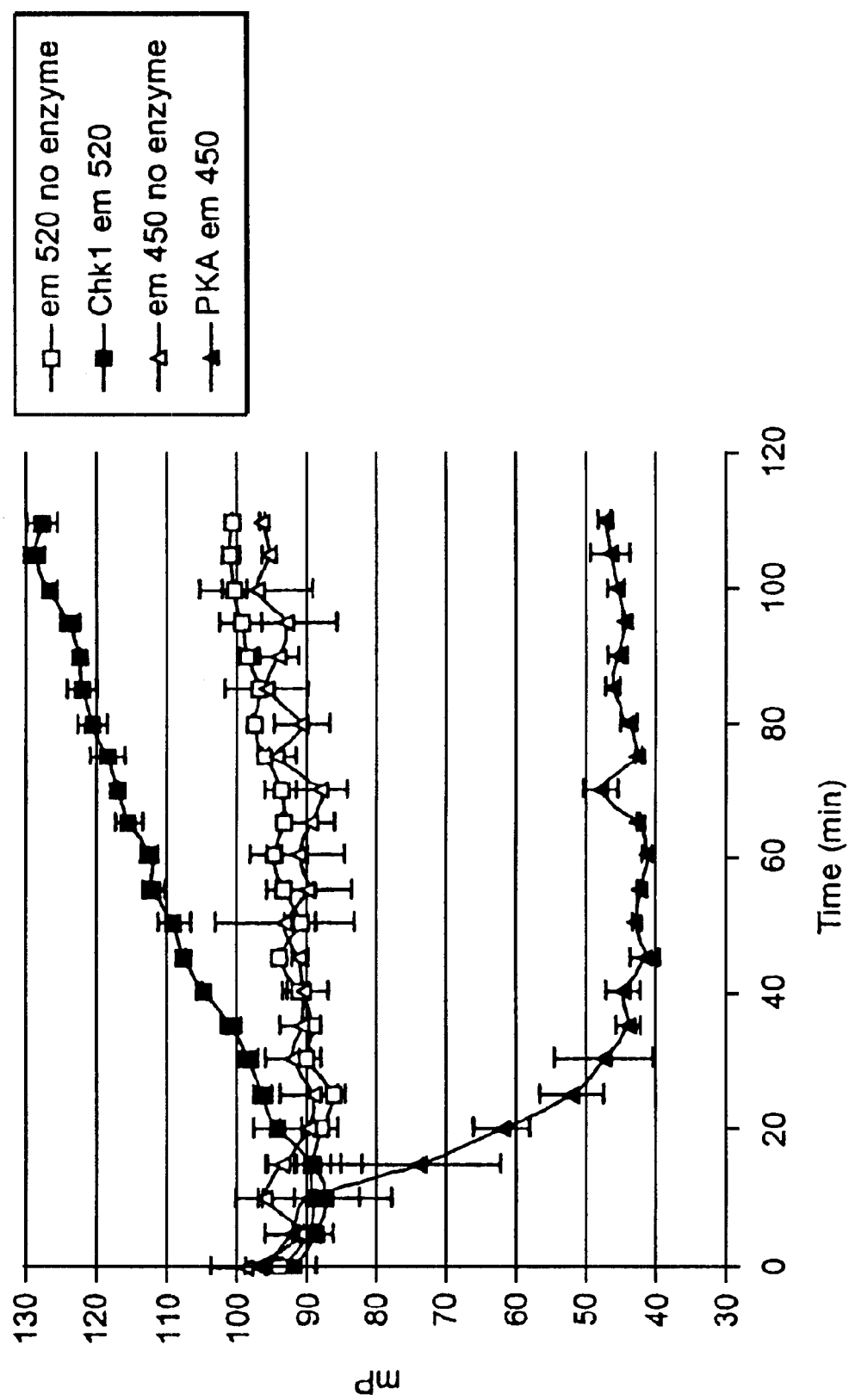

FIG. 15 presents a time course of Chk1 and PKA activity measured using fluorescence polarisation.

Figure 16:
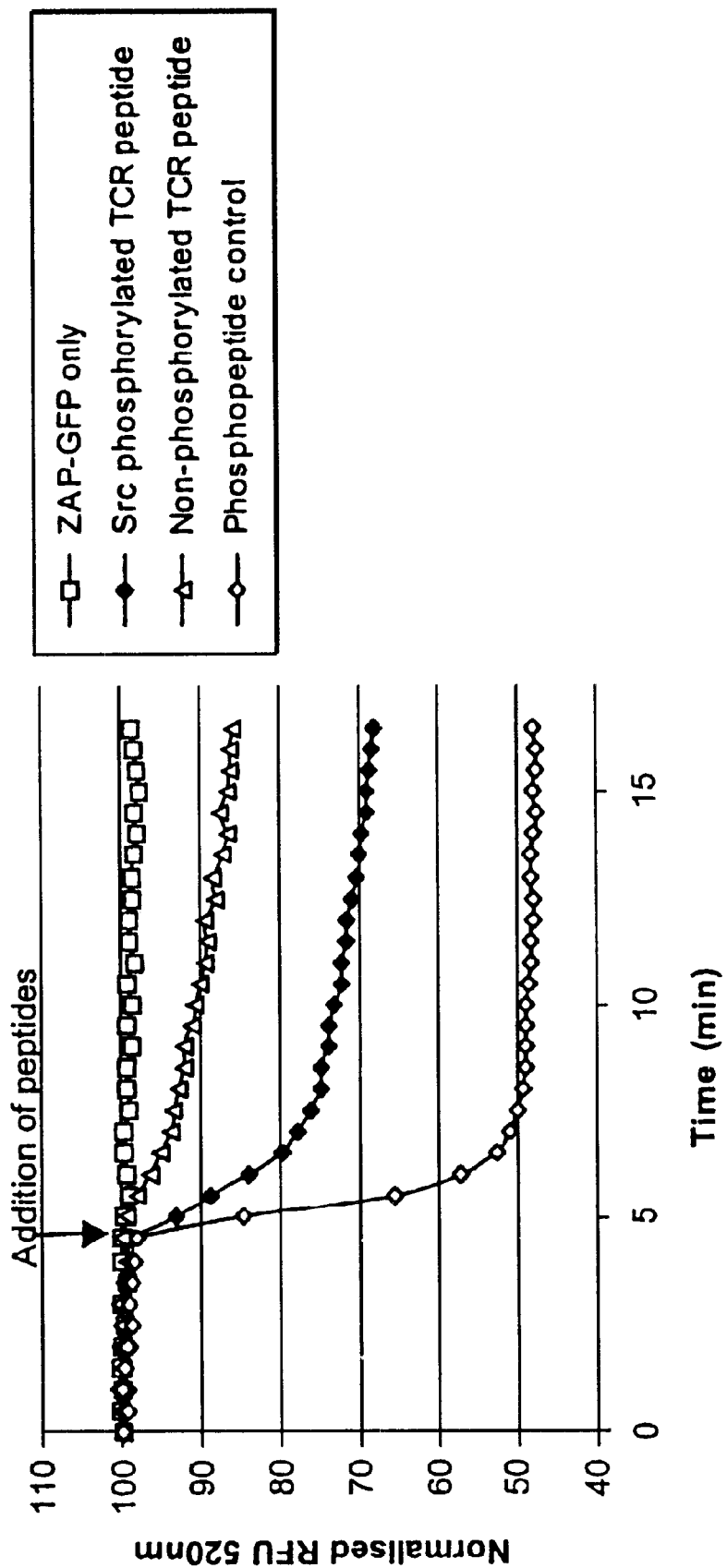

FIG. 16 demonstrates detection of peptide phosphorylation by Src kinase, by measuring FRET between ZAP-GFP and a rhodamine labelled substrate peptide.

Figure 17:
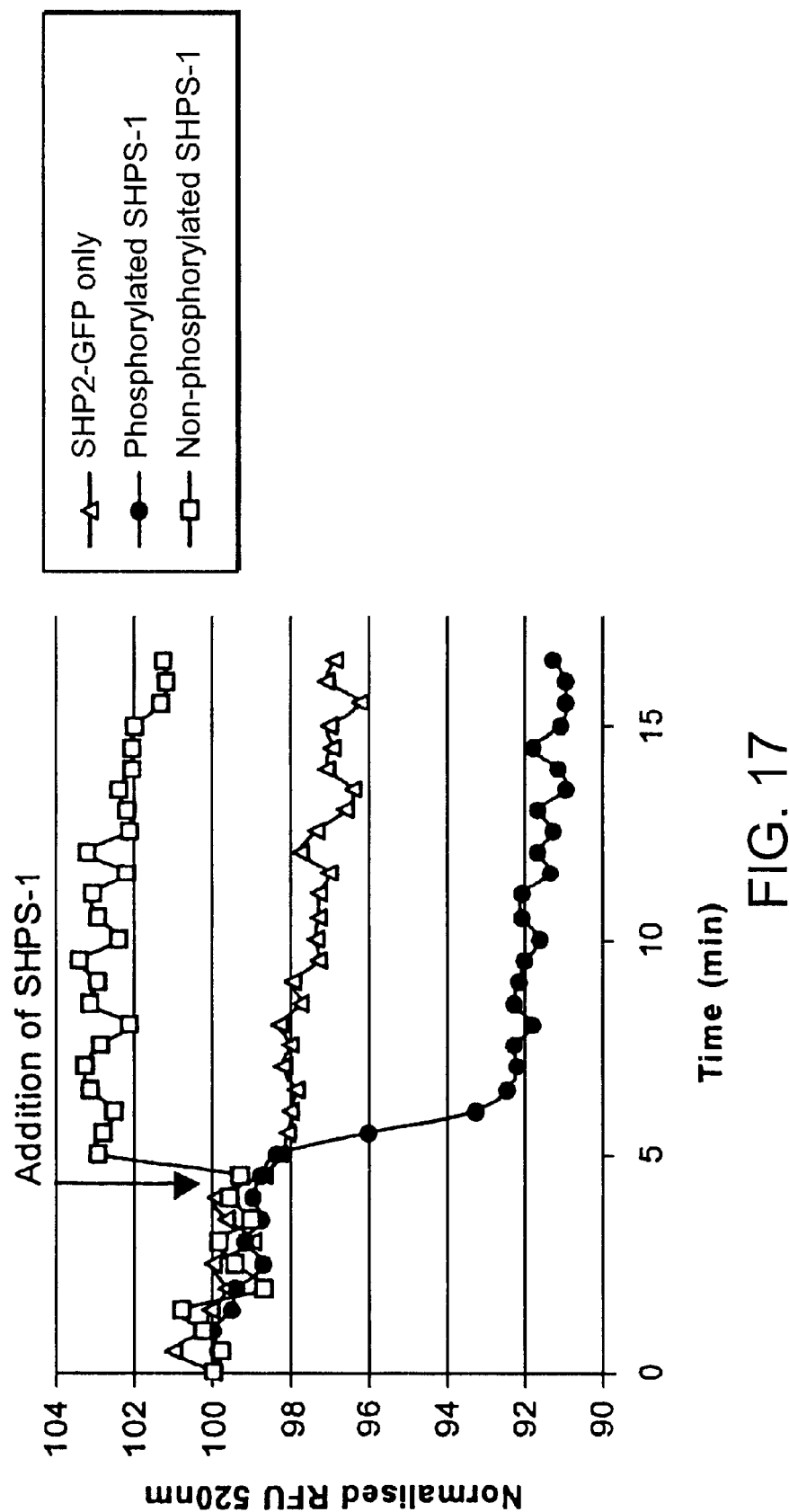

FIG. 17 demonstrates detection of SHPS-1 derived peptide phosphorylation by Src, and binding of SHPS-1 to SHP2-GFP partner.

Figure 18:
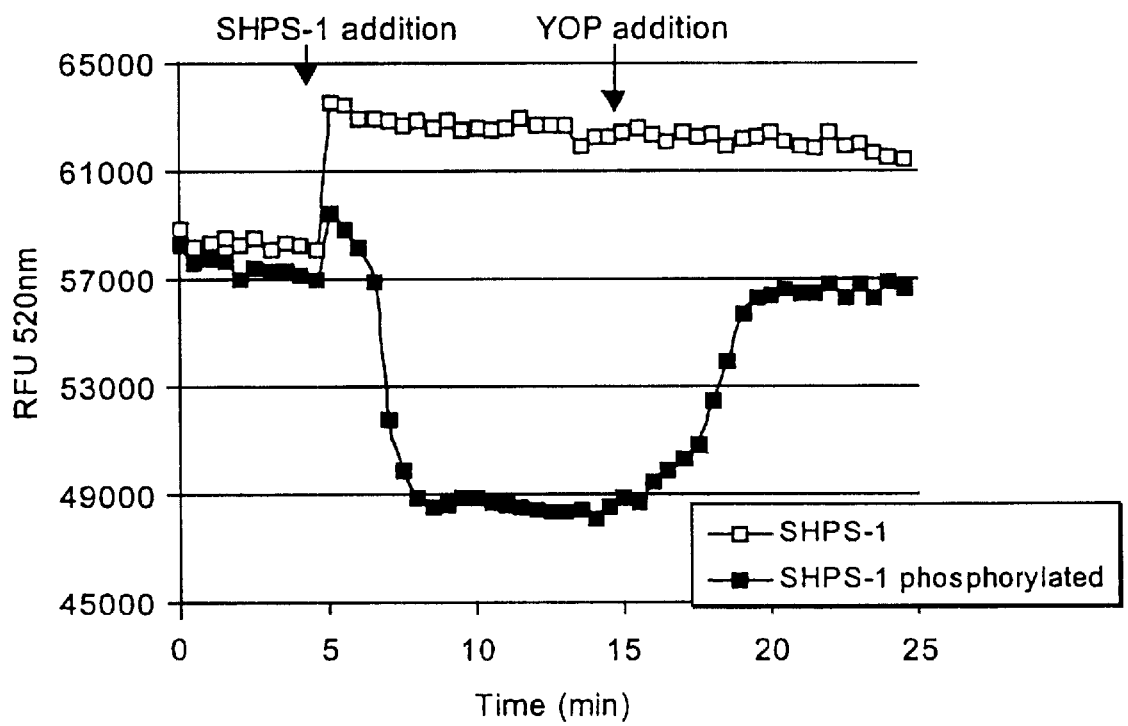

FIG. 18 demonstrates YOP mediated reversal of FRET between SHP2-GFP and rhodamine labelled, phosphorylated, SHPS-1 peptide.

Figure 19:
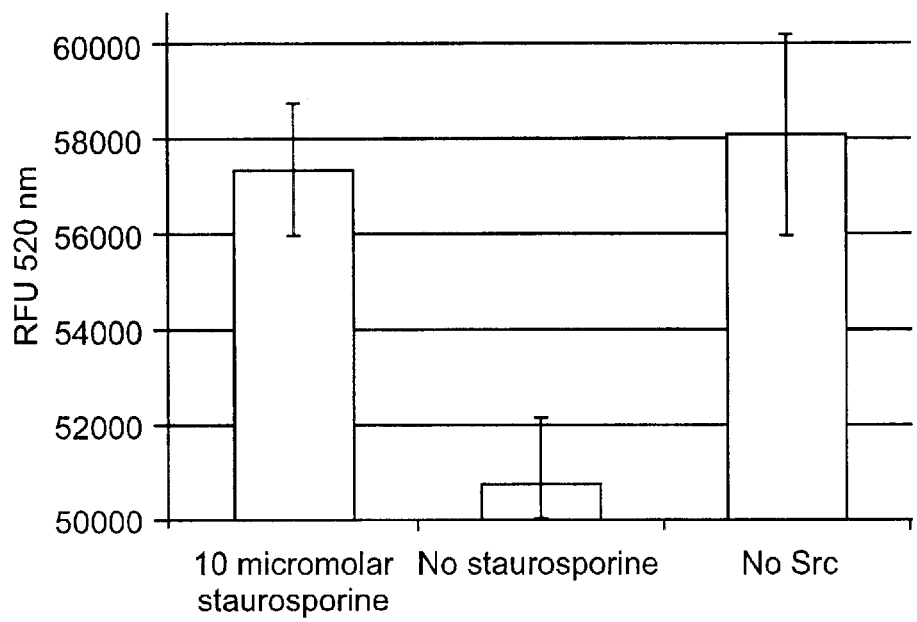

FIG. 19 presents detection of Src inhibition by staurosporine using a FRET-based assay between rhodamine labelled SHPS-1 and SHP2-GFP.

Figure 20:
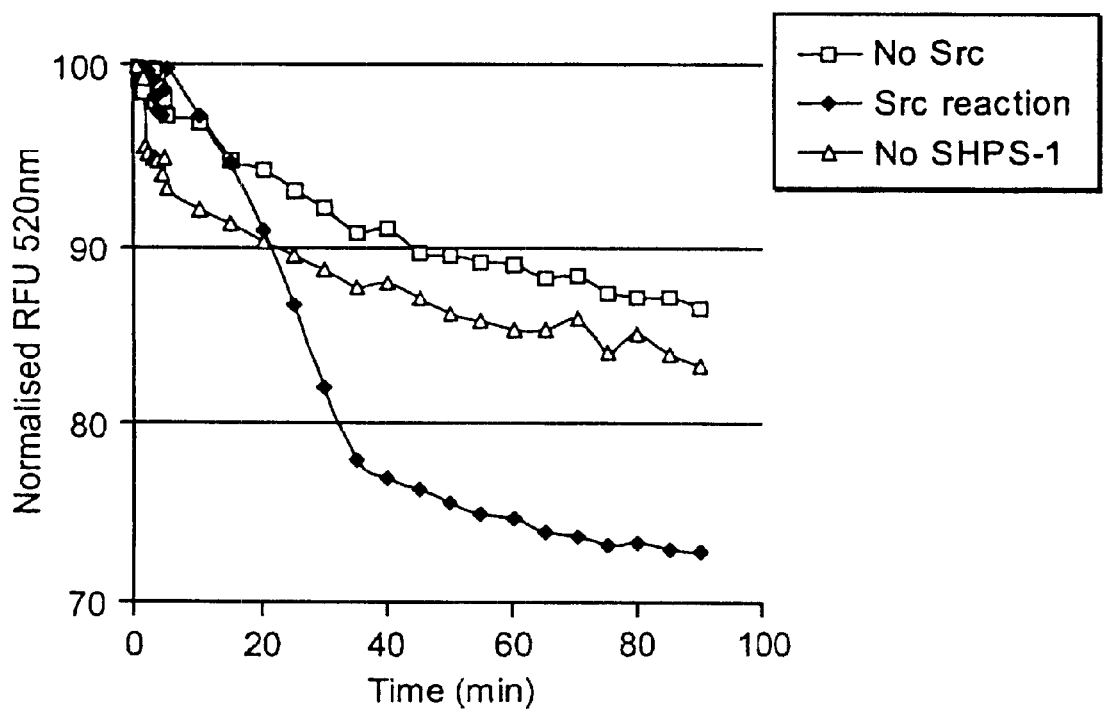

FIG. 20 presents the results of a real-time, FRET-based assay, measuring Src phosphorylation of SHPS-1 peptide.

DESCRIPTION

The invention is based upon the discovery that a natural binding domain, sequence or polypeptide, as defined above, associates with a binding partner to form a complex or dissociates from a binding partner, in a manner that is dependent upon the presence or absence of a phosphate moiety, and that is detectable and measurable in a highly sensitive manner that may be observed in real time.
Polypeptides of use in the invention The invention provides reporter molecules and assays for measuring the activity of protein kinases and phosphatases. These reporter molecules are naturally-occurring polypeptides which include natural binding domains, natural binding sequences and natural binding polypeptides, each as defined above, which are used in assays of the invention in combination with polypeptide binding partners, also as defined above.

Minimally, such a reporter molecule comprises or consists of a natural binding domain. The amino acids of a natural binding domain are those which are necessary for phosphorylation-dependent binding of the molecule comprising or consisting of the natural binding domain with a binding partner, whether such a partner is present on the same or a different polypeptide chain as the natural binding domain. Such amino acids may include points of direct contact between the domain and the binding partner, those which are recognized and/or modified (i.e., phosphorylated or dephosphorylated) by a kinase or phosphatase and those which maintain the three-dimensional structure or charge of the binding domain in a manner which permits phosphorylation and/or dephosphorylation and the consequent phosphorylation- and/or dephosphorylation-dependent binding of the domain to the binding partner. The amino acids of a natural binding domain may be contiguous or may be separated by non-domain amino acids; such non-domain residues may be either those which are naturally present between the amino acids of the natural binding domain or which are non-natural. In cases in which non-natural amino acids are found interspersed with those of a natural binding domain, such non-natural residues will be residues which do not substantially (that is, measurably) alter the natural phosphorylation-dependent binding of the natural binding domain to its binding partner.

A second reporter molecule of use in the invention is that which comprises or consists of a naturally-occurring stretch of contiguous amino acids sufficient for phosphorylation-dependent binding to a binding partner, as defined above, i.e., at least the minimum number of contiguous amino acids required to encompass a natural binding domain. The phosphorylation-dependence of such a molecule, referred to herein as a "natural binding sequence", is, itself natural. A reporter molecule of the invention may either consist of or comprise a natural binding sequence. In the latter case, amino acids outside of the natural binding sequence do not substantially influence phosphorylation-dependent binding of the natural binding domain to the binding partner.

Lastly, a reporter molecule of use in the invention may be a "natural binding polypeptide", as defined above. Such a polypeptide molecule comprises or consists of multiple natural binding domains (above), which domains are, either individually or in concert with one another, sufficient to permit natural, phosphorylation-dependent binding of the natural binding polypeptide to a binding partner.

By monitoring the association or dissociation of a natural binding domain, sequence or polypeptide and its binding partner in the presence of a known or candidate protein kinase or phosphatase, the activity of such an enzyme can be measured. In such assays, one or both of the natural binding domain, sequence or polypeptide and its binding partner comprises a detectable label including, but not exclusively, a fluorescent or other light-emitting label, which may be either chemical or proteinaceous. By measuring changes in signal emission or absorption before and after addition to the mixture comprising the natural binding domain, sequence or polypeptide and its binding partner of the enzyme to be assayed, the extent of phosphorylation can be calculated. An important feature of the invention is that such measurements (e.g., of a shift in FRET) can be performed in real-time. This allows for sensitive assessment of enzyme reaction kinetics based upon the rate of change of the protein-binding-dependent signal emission or absorption by the label(s).

Assays in which the above reporter molecules are used according to the invention may be performed either in double- or single-chain format (FIG. 1). In double-chain format, natural binding domain, sequence or polypeptide is comprised by a different polypeptide chain from that comprising or consisting of the binding partner and is not otherwise covalently linked to it. In single-chain format, the natural binding domain, sequence or polypeptide is covalently linked to its binding partner, either through an intervening amino acid sequence or a chemical linker.

The binding partner of a natural binding domain, sequence or polypeptide may, itself, be a natural binding domain, sequence or polypeptide as defined herein. If so, binding of the two molecules may depend upon the phosphorylation state of one or both in a manner that is comparable to that found in nature.

Methods by which assays of the invention are performed are described in detail in the following sections and in the Examples.

Unless defined otherwise, all technical and scientific terms used herein have the same meaning as commonly understood by one of ordinary skill in the art (e.g, in cell culture, molecular genetics, nucleic acid chemistry, hybridization techniques and biochemistry). Standard techniques are used for molecular, genetic and biochemical methods (see generally, Sambrook et al., *Molecular Cloning: A Laboratory Manual*, 2d ed. (1989) Cold Spring Harbor Laboratory Press, Cold Spring Harbor, N.Y., which is incorporated herein by reference), chemical methods, pharmaceutical formulation and delivery and treatment of patients. Methods by which to detect protein:protein binding in assays of the invention Methods of detecting the phosphorylation-dependent binding of a natural binding domain, sequence or polypeptide and a binding partner in an assay of the invention most usefully, although not exclusively, are those which employ light-emitting labels. Several such techniques are described below.

Fluorescence energy resonance transfer (FRET)

A tool with which to assess the distance between one molecule and another (whether protein or nucleic acid) or between two positions on the same molecule is provided by the technique of fluorescence resonance energy transfer (FRET), which is now widely known in the art (for a review, see Matyus, 1992, *J. Photochem. Photobiol. B: Biol.*, 12: 323–337, which is herein incorporated by reference). FRET is a radiationless process in which energy is transferred from an excited donor molecule to an acceptor molecule; the efficiency of this transfer is dependent upon the distance between the donor an acceptor molecules, as described below. Since the rate of energy transfer is inversely proportional to the sixth power of the distance between the donor and acceptor, the energy transfer efficiency is extremely sensitive to distance changes. Energy transfer is said to occur with detectable efficiency in the 1–10 nm distance range, but is typically 4–6 nm for favorable pairs of donor and acceptor.

Radiationless energy transfer is based on the biophysical properties of fluorophores. These principles are reviewed elsewhere (Lakowicz, 1983, *Principles of Flourescence Spectroscopy*, Plenum Press, New York; Jovin and Jovin, 1989, *Cell Structure and Function by Microspectrofluorometry*, eds. E. Kohen and J. G. Hirschberg, Academic Press, both of which are incorporated herein by reference). Briefly, a fluorophore absorbs light energy at a characteristic wavelength. This wavelength is also known as the excitation wavelength. The energy absorbed by a flurochrome is subsequently released through various pathways, one being emission of photons to produce fluorescence. The wavelength of light being emitted is known as the emission wavelength and is an inherent characteristic of a particular fluorophore. Radiationless energy transfer is the quantum-mechanical process by which the energy of the excited state of one fluorophore is transferred without actual photon emission to a second fluorophore. That energy may then be subsequently released at the emission wavelength of the second fluorophore. The first fluorophore is generally termed the donor (D) and has an excited state of higher energy than that of the second fluorophore, termed the acceptor (A). The essential features of the process are that the emission spectrum of the donor overlap with the excitation spectrum of the acceptor, and that the donor and acceptor be sufficiently close. The distance over which radiationless energy transfer is effective depends on many factors including the fluorescence quantum efficiency of the donor, the extinction coefficient of the acceptor, the degree of overlap of their respective spectra, the refractive index of the medium, and the relative orientation of the transition moments of the two fluorophores. In addition to having an optimum emission range overlapping the excitation wavelength of the other fluorophore, the distance between D and A must be sufficiently small to allow the radiationless transfer of energy between the fluorophores.

FRET may be performed either in vivo or in vitro. Proteins are labeled either in vivo or in vitro by methods known in the art. According to the invention, a natural binding domain, sequence or polypeptide and its binding partner, comprised either by the same or by different polypeptide molecules, are differentially labeled, one with a donor and the other with an acceptor, and differences in fluorescence between a test assay, comprising a protein modifying enzyme, and a control, in which the modifying enzyme is absent, are measured using a fluorimeter or laser-scanning microscope. It will be apparent to those skilled in the art that excitation/detection means can be augmented by the incorporation of photomultiplier means to enhance detection sensitivity. The differential labels may comprise either two different fluorescent labels (e.g., fluorescent proteins as described below or the fluorophores rhodamine, fluorescein, SPQ, and others as are known in the art) or a fluorescent label and a molecule known to quench its signal; differences in the proximity of the natural binding domain, sequence or polypeptide with its binding partner with and without the protein-modifying enzyme can be gauged based upon a difference in the fluorescence spectrum or intensity observed.

This combination of protein-labeling methods and devices confers a distinct advantage over prior art methods for determining the activity of protein-modifying enzymes, as described above, in that results of all measurements are observed in real time (i.e., as a reaction progresses). This is significantly advantageous, as it allows both for rapid data collection and yields information regarding reaction kinetics under various conditions.

A sample, whether in vitro or in vivo, assayed according to the invention therefore comprises a mixture at equilibrium of the labeled natural binding domain, sequence or polypeptide and its binding partner which, when disassociated from one another, fluoresce at one frequency and, when complexed together, fluoresce at another frequency or, alternatively, of molecules which either do or do not fluoresce or show reduced fluorescence, depending upon whether or not they are associated.

The natural binding domain, sequence or polypeptide is modified to allow the attachment of a fluorescent label to the surface of that molecule or is fused in-frame with a fluorescent protein, as described below. The choice of fluorescent label will be such that upon excitation with light, labeled peptides which are associated will show optimal energy transfer between fluorophores. In the presence of a protein kinase or phosphatase, the natural binding domain, sequence or polypeptide and its binding partner dissociate due to a structural or electrostatic change which occurs as a consequence of addition or removal of a phosphate to/from the enzyme recognition site, thereby leading to a decrease in energy transfer and increased emission of light by the donor fluorophore. In this way, the state of polypeptide phosphorylation can be monitored and quantitated in real-time. This scheme, which represents the broadest embodiment of the invention, is shown in FIG. 2.

As used herein, the terms "fluorophore" and "fluorochrome" refer interchangeably to a molecule which is capable of absorbing energy at a wavelength range and releasing energy at a wavelength range other than the absorbance range. The term "excitation wavelength" refers to the range of wavelengths at which a fluorophore absorbs energy. The term "emission wavelength" refers to the range of wavelength that the fluorophore releases energy or fluoresces.

A non-limiting list of chemical fluorophores of use in the invention, along with their excitation and emission wavelengths, is presented in Table 1.

TABLE 1

| Fluorophore | Excitation (nm) | Emission (nm) | Color |
| --- | --- | --- | --- |
| PKH2 | 490 | 504 | green |
| PKH67 | 490 | 502 | green |
| Fluorescein (FITC) | 495 | 525 | green |
| Hoechst 33258 | 360 | 470 | blue |
| R-Phycoerythrin (PE) | 488 | 578 | orange-red |
| Rhodamine (TRITC) | 552 | 570 | red |
| Quantum Red ™ | 488 | 670 | red |
| PKH26 | 551 | 567 | red |

TABLE 1-continued

| Fluorophore | Excitation (nm) | Emission (nm) | Color |
| --- | --- | --- | --- |
| Texas Red | 596 | 620 | red |
| Cy3 | 552 | 570 | red |

Examples of fluorescent proteins which vary among themselves in excitation and emission maxima are listed in Table 1 of WO 97/28261 (Tsien et al., 1997, supra). These (each followed by [excitation max./emission max.] wavelengths expressed in nanometers) include wild-type Green Fluorescent Protein [395(475)/508] and the cloned mutant of Green Fluorescent Protein variants P4 [383/447], P4–3 [381/445], W7 [433(453)/475(501)], W2 [432(453)/480], S65T [489/511], P4–1 [504(396)/480], S65A [471/504], S65C [479/507], S65L [484/510], Y66F [360/442], Y66W [458/480], I0c [513/527], W1B [432(453)/476(503)], Emerald [487/508] and Sapphire [395/511]. This list is not exhaustive of fluorescent proteins known in the art; additional examples are found in the Genbank and SwissProt public databases.

A number of parameters of fluorescence output are envisaged including
1) measuring fluoresence emitted at the emission wavelength of the acceptor (A) and donor (D) and determining the extent of energy transfer by the ratio of their emission amplitudes;
2) measuring the fluoresence lifetime of D;
3) measuring the rate of photobleaching of D;
4) measuring the anisotropy of D and/or A; or
5) measuring the Stokes shift monomer; excimer fluorescence. Certain of these techniques are presented below.

Alternative fluorescent techniques suitable for monitoring protein:protein binding in assays of the invention One embodiment of the technology can utilize monomer-:excimer fluorescence as the output. The association of a natural binding domain with a binding partner in this format is shown in FIG. 3.

The fluorophore pyrene when present as a single copy displays fluorescent emission of a particular wavelength significantly shorter than when two copies of pyrene form a planar dimer (excimer), as depicted. As above, excitation at a single wavelength (probably 340 nm) is used to review the excimer fluorescence (~470 nm) over monomer fluorescence (~375 nm) to quantify assembly:disassembly of the reporter molecule.

Additional embodiments of the present invention are not dependent on FRET. For example the invention can make use of fluorescence correlation spectroscopy (FCS), which relies on the measurement of the rate of diffusion of a label (see Elson and Magde, 1974 *Biopolymers*, 13: 1–27; Rigler et al., 1992, in *Fluorescence Spectroscopy: New Methods and Applications*, Springer Verlag, pp.13–24; Eigen and Rigler, 1994, Proc. Natl. Acad. Sci. U.S.A., 91: 5740–5747; Kinjo and Rigler, 1995, *Nucleic Acids Res.*, 23: 1795–1799).

In FCS, a focused laser beam illuminates a very small volume of solution, of the order of $10^{-15}$ liter, which at any given point in time contains only one molecule of the many under analysis. The diffusion of single molecules through the illuminated volume, over time, results in bursts of fluorescent light as the labels of the molecules are excited by the laser. Each individual burst, resulting from a single molecule, can be registered.

A labeled polypeptide will diffuse at a slower rate if it is large than if it is small. Thus, multimerized polypeptides will display slow diffusion rates, resulting in a lower number of fluorescent bursts in any given timeframe, while labeled polypeptides which are not multimerized or which have dissociated from a multimer will diffuse more rapidly. Binding of polypeptides according to the invention can be calculated directly from the diffusion rates through the illuminated volume.

Where FCS is employed, rather than FRET, it is not necessary to label more than one polypeptide. Preferably, a single polypeptide member of the multimer is labeled. The labeled polypeptide dissociates from the multimer as a result of modification, thus altering the FCS reading for the fluorescent label.

A further detection technique which may be employed in the method of the present invention is the measurement of time-dependent decay of fluorescence anisotropy. This is described, for example, in Lacowicz, 1983, *Principles of Flourescence Spectroscopy*, Plenum Press, New York, incorporated herein by reference (see, for example, page 167).

Fluorescence anisotropy relies on the measurement of the rotation of fluorescent groups. Larger multimers of polypeptides rotate more slowly than monomers, allowing the formation of multimers to be monitored.

Non-fluorescent detection methods for use in the invention

The invention may be configured to exploit a number of non-fluorescent labels. In a first embodiment, the natural binding domain and binding partner therefor form, when bound, an active enzyme which is capable of participating in an enzyme-substrate reaction which has a detectable endpoint. The enzyme may comprise two or more polypeptide chains or regions of a single chain, such that upon binding of the natural binding domain to the binding partner, which are present either on two different polypeptide chains or in two different regions of a single polypeptide, these components assemble to form a functional enzyme. Enzyme function may be assessed by a number of methods, including scintillation counting and photospectroscopy. In a further embodiment, the invention may be configured such that the label is a redox enzyme, for example glucose oxidase, and the signal generated by the label is an electrical signal.

Phosphorylation of the natural binding domain and, optionally, its binding partner according to the invention is required to inhibit binding and, consequently, enzyme component assembly, thus reducing enzyme activity.

In another assay format, an enzyme is used together with a modulator of enzyme activity, such as an inhibitor or a cofactor. In such an assay, one of the enzyme and the inhibitor or cofactor is an natural binding domain, the other its binding partner. Binding of the enzyme to its inhibitor or cofactor results in modulation of enzymatic activity, which is detectable by conventional means (such as monitoring for the conversion of substrate to product for a given enzyme).

Fluorescent protein labels in assays of the invention

In a FRET assay of the invention, the fluorescent protein labels are chosen such that the excitation spectrum of one of the labels (the acceptor) overlaps with the emission spectrum of the excited fluorescent label (the donor). The donor label is excited by light of appropriate intensity within the donor's excitation spectrum. The donor then emits some of the absorbed energy as fluorescent light and dissipates some of the energy by FRET to the acceptor fluorescent label. The fluorescent energy it produces is quenched by the acceptor fluorescent protein label. FRET can be manifested as a reduction in the intensity of the fluorescent signal from the donor, reduction in the lifetime of its excited state, and re-emission of fluorescent light at the longer wavelengths (lower energies) characteristic of the acceptor. When the donor and acceptor labels become spatially separated, FRET is diminished or eliminated.

One can take advantage of the FRET exhibited by a natural binding domain, sequence or polypeptide and its binding partner labeled with different fluorescent proteins, wherein one is linked to a donor and the other to an acceptor fluorescent protein, in monitoring protein phosphorylation according to the present invention. A single polypeptide may comprises a blue fluorescent protein donor and a green fluorescent protein acceptor, wherein each is fused to a different assay component (i.e., in which one is fused to the natural binding domain, sequence or polypeptide and the other to its binding partner); such a construct is herein referred to as a "tandem" fusion protein. Alternatively, two distinct polypeptides ("single" fusion proteins) one comprising a natural binding domain, sequence or polypeptide and the other its binding partner may be differentially labeled with the donor and acceptor fluorescent proteins, respectively. The construction and use of tandem fusion proteins in the invention can reduce significantly the molar concentration of peptides necessary to effect an association between differentially-labeled polypeptide assay components relative to that required when single fusion proteins are instead used. The labeled natural binding domain, sequence or polypeptide and/or its binding partner may be produced via the expression of recombinant nucleic acid molecules comprising an in-frame fusion of sequences encoding a such a polypeptide and a fluorescent protein label either in vitro (e.g., using a cell-free transcription/translation system, as described below, or instead using cultured cells transformed or transfected using methods well known in the art) or in vivo, for example in a transgenic animal including, but not limited to, insects, amphibians and mammals. A recombinant nucleic acid molecule of use in the invention may be constructed and expressed by molecular methods well known in the art, and may additionally comprise sequences including, but not limited to, those which encode a tag (e.g., a histidine tag) to enable easy purification, a secretion signal, a nuclear localization signal or other primary sequence signal capable of targeting the construct to a particular cellular location, if it is so desired.

The means by which a natural binding domain, sequence or polypeptide and its binding partner are assayed for association using fluorescent protein labels according to the invention may be briefly summarized as follows:

Whether or not the natural binding domain, sequence or polypeptide and its binding partner are present on a single polypeptide molecule, one is labeled with a green fluorescent protein, while the other is preferably labeled with a red or, alternatively, a blue fluorescent protein. Useful donor:acceptor pairs of fluorescent proteins (see Tsien et al., 1997, supra) include, but are not limited to:

Donor: S72A, K79R, Y145F, M153A and T203I (excitation $\lambda$ 395 nm; emission $\lambda$ 511)

Acceptor: S65G, S72A, K79R and T203Y (excitation $\lambda$ 514 nm; emission $\lambda$ 527 nm), or T203Y/S65G, V68L, Q69K or S72A (excitation $\lambda$ 515 nm; emission $\lambda$ 527 nm).

An example of a blue:green pairing is P4–3 (shown in Table 1 of Tsien et al., 1997, supra) as the donor label and S65C (also of Table 1 of Tsien et al., 1997, supra) as the acceptor label. The natural binding domain, sequence or polypeptide and corresponding binding partner are exposed to light at, for example, 368 nm, a wavelength that is near the excitation maximum of P4–3. This wavelength excites S65C only minimally. Upon excitation, some portion of the energy absorbed by the blue fluorescent protein donor is transferred to the acceptor through FRET if the natural binding domain, sequence or polypeptide and its binding partner are in close association. As a result of this quenching, the blue fluorescent light emitted by the blue fluorescent protein is less bright than would be expected if the blue fluorescent protein existed in isolation. The acceptor (S65C) may re-emit the energy at longer wavelength, in this case, green fluorescent light.

After phosphorylation or dephosphorylation of one or both of the natural binding domain, sequence or polypeptide and its binding partner by an kinase or phosphatase, respectively, the natural binding domain, sequence or polypeptide and its binding partner (and, hence, the green and red or, less preferably, green and blue fluorescent proteins) physically separate or associate, accordingly inhibiting or promoting FRET. For example, if activity of the modifying enzyme results in dissociation of a protein:protein dimer, the intensity of visible blue fluorescent light emitted by the blue fluorescent protein increases, while the intensity of visible green light emitted by the green fluorescent protein as a result of FRET, decreases.

Such a system is useful to monitor the activity of enzymes that phosphorylate or dephosphorylate the phosphorylation site of a natural binding domain, sequence or polypeptide and, optionally, its binding partner to which the fluorescent protein labels are fused, as well as the activity of kinases or phosphatases or candidate modulators of those enzymes.

In particular, this invention contemplates assays in which the amount- or activity of a modifying enzyme in a sample is determined by contacting the sample with a natural binding domain, sequence or polypeptide and its binding partner, differentially-labeled with fluorescent proteins, as described above, and measuring changes in fluorescence of the donor label, the acceptor label or the relative fluorescence of both. Fusion proteins, as described above, which comprise either one or both of the labeled natural binding domain, sequence or polypeptide and its binding partner of an assay of the invention can be used for, among other things, monitoring the activity of a protein kinase or phosphatase inside the cell that expresses the recombinant tandem construct or two different recombinant constructs.

Advantages of single- and tandem fluorescent protein/polypeptides comprising a natural binding domain, sequence or polypeptide fused to a fluorescent protein include the potential to express the natural binding domain, sequence or polypeptide in the cell (providing a convenient experimental format), the greater extinction coefficient and quantum yield of many of these proteins compared with those of the Edans fluorophore. Also, the acceptor in such a construct or pair of constructs is, itself, a fluorophore rather than a non-fluorescent quencher like Dabcyl. Alternatively, in single-label assays of the invention, whether involving use of a chemical fluorophore or a single fluorescent fusion construct, such a non-fluorescent quencher may be used. Thus, the enzyme's substrate (i.e., the natural binding domain and, optionally, the corresponding binding partner), and reaction products (i.e., the natural binding domain and, optionally, the corresponding binding partner after modification) are both fluorescent but with different fluorescent characteristics.

In particular, the substrate and modified products exhibit different ratios between the amount of light emitted by the donor and acceptor labels. Therefore, the ratio between the two fluorescences measures the degree of conversion of substrate to products, independent of the absolute amount of either, the optical thickness of the sample, the brightness of the excitation lamp, the sensitivity of the detector, etc. Furthermore, Aequorea-derived or -related fluorescent protein labels tend to be protease resistant. Therefore, they are likely to retain their fluorescent properties throughout the course of an experiment.

Reporter polyeptide fusion according to the invention

As stated above, recombinant nucleic acid constructs of particular use in the invention are those which comprise in-frame fusions of sequences encoding a natural binding domain, sequence or polypeptide or a binding partner therefor and a fluorescent protein. If a natural binding domain, sequence or polypeptide and its binding partner are to be expressed as part of a single polypeptide, the nucleic acid molecule additionally encodes, at a minimum, a donor fluorescent protein fused to one, an acceptor fluorescent protein label fused to the other, a linker that couples the two and is of sufficient length and flexibility to allow for folding of the polypeptide and pairing of the natural binding domain, sequence or polypeptide with the binding partner, and gene regulatory sequences operatively linked to the fusion coding sequence. If single fusion proteins are instead encoded (whether by one or more nucleic acid molecules), each nucleic acid molecule need only encode a natural binding domain, sequence or polypeptide or a binding partner therefor, fused either to a donor or acceptor fluorescent protein label and operatively linked to gene regulatory sequences. "Operatively-linked" refers to polynucleotide sequences which are necessary to effect the expression of coding and non-coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, components whose presence can influence expression, and can also include additional components whose presence is advantageous, for example, leader sequences and fusion partner sequences.

As described above, the donor fluorescent protein label is capable of absorbing a photon and transferring energy to another fluorescent label. The acceptor fluorescent protein label is capable of absorbing energy and emitting a photon. If needed, the linker connects the natural binding domain, sequence or polypeptide and its binding partner either directly or indirectly, through an intermediary linkage with one or both of the donor and acceptor fluorescent protein labels. Regardless of the relative order of the natural binding domain, sequence or polypeptide, its binding partner and the donor and acceptor fluorescent protein labels on a polypeptide molecule, it is essential that sufficient distance be placed between the donor and acceptor by the linker and/or the natural binding domain, sequence or polypeptide and its binding partner to ensure that FRET does not occur unless the natural binding domain, sequence or polypeptide and its binding partner bind. It is desirable, as described in greater detail in WO97/28261, to select a donor fluorescent protein with an emission spectrum that overlaps with the excitation spectrum of an acceptor fluorescent protein. In some embodiments of the invention the overlap in emission and excitation spectra will facilitate FRET. Such an overlap is not necessary, however, if intrinsic fluorescence is measured instead of FRET. A fluorescent protein of use in the invention includes, in addition to those with intrinsic fluorescent properties, proteins that fluoresce due intramolecular rearrangements or the addition of cofactors that promote fluorescence.

For example, green fluorescent proteins ("GFPs") of cnidarians, which act as their energy-transfer acceptors in bioluminescence, can be used in the invention. A green fluorescent protein, as used herein, is a protein that fluoresces green light, and a blue fluorescent protein is a protein that fluoresces blue light. GFPs have been isolated from the Pacific Northwest jellyfish, *Aequorea victoria*, from the sea pansy, *Renilla reniformis*, and from *Phialidium gregarium*. (Ward et al., 1982, *Photochem. Photobiol.*, 35: 803–808; Levine et al., 1982, *Comp. Biochem. Physiol.*, 72B: 77–85).

A variety of Aequorea-related GFPs having useful excitation and emission spectra have been engineered by modifying the amino acid sequence of a naturally occurring GFP from *Aequorea victoria*. (Prasher et al., 1992, *Gene*, 111: 229–233; Heim et al., 1994, *Proc. Natl. Acad. Sci. U.S.A.*, 91: 12501–12504; PCT/US95/14692). As used herein, a fluorescent protein is an Aequorea-related fluorescent protein if any contiguous sequence of 150 amino acids of the fluorescent protein has at least 85% sequence identity with an amino acid sequence, either contiguous or non-contiguous, from the wild-type Aequorea green fluorescent protein of SwissProt Accession No. P42212. Similarly, the fluorescent protein may be related to Renilla or Phialidium wild-type fluorescent proteins using the same standards.

Aequorea-related fluorescent proteins include, for example, wild-type (native) *Aequorea victoria* GFP, whose nucleotide and deduced amino acid sequences are presented in Genbank Accession Nos. L29345, M62654, M62653 and others Aequorea-related engineered versions of Green Fluorescent Protein, of which some are listed above. Several of these, i.e., P4, P4–3, W7 and W2 fluoresce at a distinctly shorter wavelength than wild type.

Recombinant nucleic acid molecules encoding single- or tandem fluorescent protein/polypeptide comprising a natural binding domain, sequence or polypeptide or a binding partner therefor fused to a fluorescent protein useful in the invention may be expressed for in vivo assay of the activity of a modifying enzyme on the encoded products. Alternatively, the encoded fusion proteins may be isolated prior to assay, and instead assayed in a cell-free in vitro assay system, as described elsewhere herein.

Protein phosphorylation in assays of the invention

As highlighted in the Background, the phosphorylation of proteins is a frequent and important post-translational modification of proteins. There are many examples of situations in which dysfunction of the kinases and phosphatases mediating the phosphorylation state of proteins can lead to disease. The methods currently available to analyze the phosphorylation state each have drawbacks, as described above. Assay formats of the invention, as outlined in the following sections and in the Examples, below, will allow monitoring of the phosphorylation state of a specific target protein or activity of a specific kinase or phosphatase in real time in the cell.

Three systems, presented in Examples 1 through 4, can be used to exemplify in non-limiting fashion the phosphorylation assay, each of which involves the interaction between a binding domain, sequence or polypeptide and a binding partner, of which at least the former comprises a modification site that serves as a substrate for the protein kinases and phosphatases involved in the system. At the present time, good structural information is available for such interactions.

Methods for detection of protein phosphorylation in real time

A. A in vitro protein modification and detection thereof

Modifying enzymes

The invention requires the presence of a modifying enzyme which catalyzes either the addition or removal of a modifying group. A range of kinases, phosphatases and other modifying enzymes are available commercially (e.g. from Sigma, St. Louis, Mo.; Promega, Madison, Wis.; Boehringer Mannheim Biochemicals, Indianapolis, Ind.; New England Biolabs, Beverly, Mass.; and others). Alternatively, such enzymes may be prepared in the laboratory by methods well known in the art.

The catalytic sub-unit of protein kinase A (c-PKA) can be purified from natural sources (e.g. bovine heart) or from cells/organisms engineered to heterologously express the enzyme. Other isofonrns of this enzyme may be obtained by these procedures. Purification is performed as previously described from bovine heart (Peters et al.,1977, *Biochemistry*, 16: 5691–5697) or from a heterologous source (Tsien et al., WO92/00388), and is in each case briefly summarized as follows:

Bovine ventricular cardiac muscle (2 kg) is homogenized and then centrifuged. The supernatant is applied to a strong anion exchange resin (e.g. Q resin, Bio-Rad) equilibrated in a buffer containing 50 mM Tris-HCl, 10 mM NaCl, 4 mM EDTA pH 7.6 and 0.2 mM 2-mercaptoethanol. The protein is eluted from the resin in a second buffer containing 50 mM Tris-HCI, 4 mM EDTA pH 7.6, 0.2 mM 2-mercaptoethanol, 0.5M NaCi. Fractions containing PKA are pooled and ammonium sulphate added to 30% saturation. Proteins precipitated by this are removed by centrifugation and the ammonium sulphate concentration of the supernatant was increased to 75% saturation. Insoluble proteins are collected by centrifugation (included c-PKA) and are dissolved in 30 mM phosphate buffer pH 7.0, 1 mM EDTA, 0.2 mM 2-mercaptoethanol. These proteins are then dialysed against the same buffer (500 volume excess) at 4° C for two periods of 8 hours each. The pH of the sample is reduced to 6.1 by addition of phosphoric acid, and the sample is mixed sequentially with 5 batches of CM-Sepharose (Pharmacia, ~80 ml resin each) equilibrated in 30 mM phosphate pH 6.1, 1 mM EDTA, 0.2 mM 2-mercaptoethanol. Cyclic AMP (10 $\mu$M) is added to the material which fails to bind to the CM-Sepharose, and the sample- cAMP mix is incubated with a fresh resin of CM-Sepharose (~100 ml) equilibrated as before. c-PKA is eluted from this column following extensive washing in equilibration buffer by addition of 3OmM phosphate pH 6.1, 1 mM EDTA, IM KCl, 0.2 mM 2- mercaptoethanol. Fractions containing c-PKA are pooled and concentrated by filtration through a PM-30 membrane (or similar). The c-PKA sample is then subjected to gel-filtration chromatography on a resin such as Sephacryl 200HR (Pharmacia).

The purification of recombinant c-PKA is as described in WO 92/00388. General methods of preparing pure and partially-purified recombinant proteins, as well as crude cellular extracts comprising such proteins, are well known in the art. Molecular methods useful in the production of recombinant proteins, whether such proteins are the enzymes to be assayed according to the invention or the labeled reporter polypeptides of the invention (i.e., the natural binding domain, sequence or polypeptide and its binding partner), are well known in the art (for methods of cloning, expression of cloned genes and protein purification, see Sambrook et al., 1989, *Molecular Cloning. A Laboratory Manual.*, 2nd *Edition*, Cold Spring Harbor Laboratory Press, Cold Spring Harbor, N.Y.; Ausubel et al., *Current Protocols in Molecular Biology*, copyright 1987–1994, Current Protocols, copyright 1994–1998, John Wiley & Sons, Inc.). The sequences of the catalytic subunit of several PKA molecules are found in the Genbank database (see PKA Cα, bovine, Genbank Accession Nos. X67154 and S49260; PKA Cβ1, bovine, Genbank Accession No. J02647; PKA Cβ2, bovine, M60482, the form most likely purified from bovine heart by the protocol described above).

According to the invention, assays of the activity of protein kinases or phosphatases may be performed using crude cellular extracts, whether to test the activity of a recombinant protein or one which is found in nature, such as in a biological sample obtained from a test cell line or animal or from a clinical patient. In the former case, use of a crude cell extract enables rapid screening of many samples, which potentially finds special application in high-throughput screening methods, e.g. of candidate modulators of protein kinase/phosphatase activity. In the latter case, use of a crude extract with the labeled reporter polypeptide comprising a natural binding domain, sequence or polypeptide of the invention facilitates easy and rapid assessment of the activity of an enzyme of interest in a diagnostic procedure, e.g., one which is directed at determining whether a protein kinase or phosphatase is active at an a physiologically-appropriate level, or in a procedure designed to assess the efficacy of a therapy aimed at modulating the activity of a particular enzyme.

Production of a natural binding domain, sequence or polypeptide

Polypeptides comprising or consisting of a natural binding domain, sequence or polypeptide or a binding partner thereof may be synthesized by Fmoc or Tboc chemistry according to methods known in the art (e.g., see Atherton et al., 1981, *J. Chem. Soc. Perkin* I, 1981(2): 538–546; Merrifield, 1963, *J. Am. Chem. Soc.*, 85: 2149–2154, respectively). Following deprotection and cleavage from the resin, peptides are desalted by gel filtration chromatography and analysed by mass spectroscopy, HPLC, Edman degradation and/or other methods as are known in the art for protein sequencing using standard methodologies.

Alternatively, nucleic acid sequences encoding such peptides may be expressed either in cells or in an in vitro transcription/translation system (see below) and, as with enzymes to be assayed according to the invention, the proteins purified by methods well known in the art.

Labelling of polypeptides with fluorophores

Polypeptides comprising or consisting of natural binding domains, sequences or polypeptides or a binding partner therefor are labeled with thiol reactive derivatives of fluorescein and tetramethylrhodamine (isothiocyanate or iodoacetamide derivatives, Molecular Probes, Eugene, OR, USA) or other fluorophores as are known in the art using procedures described by Hermanson G.T., 1995, Bioconjugate ues, Academic Press, London. Alternatively, primary-amine-directed conjugation reactions can be used to label lysine sidechains or the free peptide N-terminus (Hermason, 1995, supra).

Purification of fluorescent natural binding domains and/or binding partners therefor Fluorescent peptides are separated from unreacted fluorophores by gel filtration chromatography or reverse phase HPLC.

Phosphorylation of natural binding domains and, optionally, binding partners therefor in vitro Natural binding domains and, optionally, binding partners therefor (0.01–100.0CM) are phosphorylated by purified c-PKA in 50mM Histidine buffer pH 7.0, 5 mM $MgSO_4$, 1mM EGTA, 0.1–10.0 μM c-PKA, and 0.2 mM [$^{32}P$] γ-ATP (specific activity ~2Bq/pmol) at 15–40° C. for periods of time ranging from 0 to 60 minutes. Where the chemistry of the peptide is appropriate (i.e. having a basic charge) the phosphopeptide is captured on a cation exchange filter paper (e.g. phosphocellulose P81 paper; Whatman), and reactants are removed by extensive washing in 1% phosphoric acid (see Casnellie, 1991, *Methods Enzynmol.*, 200: 115–120). Alternatively, phosphorylation of samples is terminated by the addition of SDS-sample buffer (Laemmli,1970, *Nature*, 227: 680–685) and the samples analysed by SDS-PAGE electrophoresis, autoradiography and scintillation counting of gel pieces.

Dephosphorylation of a natural binding domain or binding partner therefor in vitro The dephosphorylation of natural binding domains and, optionally, binding partners therefor, phosphorylated as above is studied by removal of ATP (through the addition of 10 mM glucose and 30 U/ml hexokinase; Sigma, St. Louis, Mo.) and addition of protein phosphatase-1 (Sigma). Dephosphorylation is followed at 15–40° C. by quantitation of the remaining phosphopeptide component at various time points, determined as above.

Fluorescence measurements of protein modification in vitro in real time

Donor and acceptor fluorophore-labeled polypeptides comprising or consisting of natural binding domains, sequences or polypeptides (molar equivalents of fluorophore- labeled polypeptide or molar excess of acceptor-labeled polypeptide) are first mixed (if the natural binding domains, sequence or polypeptide and its binding partner are present on separate polypeptides). Samples are analyzed in a fluorimeter using excitation wavelengths relevant to the donor fluorescent label and emission wavelengths relevant to both the donor and acceptor labels. A ratio of emission from the acceptor over that from the donor following excitation at a single wavelength is used to determine the efficiency of fluorescence energy transfer between fluorophores, and hence their spatial proximity. Typically, measurements are performed at 0–37° C as a function of time following the addition of the modifying enzyme (and, optionally, a modulator or candidate modulator of function for that enzyme, as described below) to the system in 50mM histidine pH 7.0, 120 mM KCl, 5 mM $MgSO_4$, 5 mM NaF, 0.05 mM EGTA and 0.2 mM ATP. The assay may be performed at a higher temperature if that temperature is compatible with the enzyme(s) under study.

Altenative cell-free assay system of the invention

A cell-free assay system according to the invention is required to permit binding of an unmodified, labeled natural binding domain, sequence or polypeptide and its binding partner to occur. As indicated herein, such a system may comprise a low-ionic-strength buffer (e.g., physiological salt, such as simple saline or phosphate- and/or Tris-buffered saline or other as described above), a cell culture medium, of which many are known in the art, or a whole or fractionated cell lysate. The components of an assay of protein modification according to the invention may be added into a buffer, medium or lysate or may have been expressed in cells from which a lysate is derived. Alternatively, a cell-free transcription- and/or translation system may be used to deliver one or more of these components to the assay system. Nucleic acids of use in cell-free expression systems according to the invention are as described for in vivo assays, below.

An assay of the invention may be peformed in a standard in vitro transcription/translation system under conditions which permit expression of a recombinant or other gene. The TNT® T7 Quick Coupled Transcription/Translation System (Cat.# L1170; Promega) contains all reagents necessary for in vitro transcription/translation except the DNA of interest and the detection label; as discussed below, polypeptides comprising natural binding domains, sequences or polypeptides or their binding partners may be encoded by expression constructs in which their coding sequences are fused in-frame to those encoding fluorescent proteins. The TNT® Coupled Reticulocyte Lysate Systems (comprising a rabbit reticulocyte lysate) include: TNT®V T3 Coupled Reticulocyte Lysate System (Cat. # L4950; Promega); TNT® T7 Coupled Reticulocyte Lysate System (Cat. # L4610; Promega); TNT® SP6 Coupled Reticulocyte Lysate System (Cat. # L4600; Promega); TNT® T7/SP6 Coupled Reticulocyte Lysate System (Cat. # L5020; Promega); TNT® T7/T3 Coupled Reticulocyte Lysate System (Cat. # L5010; Promega).

An assay involving a cell lysate or a whole cell (see below) may be performed in a cell lysate or whole cell preferably eukaryotic in nature (such as yeast, fungi, insect, e.g., Drosophila), mouse, or human). An assay in which a cell lysate is used is performed in a standard in vitro system under conditions which permit gene expression. A rabbit reticulocyte lysate alone is also available from Promega, either nuclease-treated (Cat. # L4960) or untreated (Cat. # L4151).

Candidate modulators is of protein kinases and/or phosphatases to be screened according to the invention Whether in vitro or in an in vivo system (see below), the invention encompasses methods by which to screen compositions which may enhance, inhibit or not affect (e.g., in a cross-screening procedure in which the goal is to determine whether an agent intended for one purpose additionally affects general cellular functions, of which protein phosphorylation/dephosphorylation is an example) the activity of a protein kinase or phosphatase.

Candidate modulator compounds from large libraries of synthetic or natural compounds can be screened. Numerous means are currently used for random and directed synthesis of saccharide, peptide, and nucleic acid based compounds. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Combinatorial libraries are available and can be prepared. Alternatively, libraries of natural compounds in the form of bacterial, fungal, plant and animal extracts are available from e.g., Pan Laboratories (Bothell, Wash.) or MycoSearch (NC), or are readily produceable by methods well known in the art. Additionally, natural and synthetically produced libraries and compounds are readily modified through conventional chemical, physical, and biochemical means.

Useful compounds may be found within numerous chemical classes, though typically they are organic compounds, including small organic compounds. Small organic compounds have a molecular weight of more than 50 yet less than about 2,500 daltons, preferably less than about 750, more preferably less than about 350 daltons. Exemplary classes include heterocycles, peptides, saccharides, steroids, and the like. The compounds may be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxylic terminus, e.g. for the amino group, acylation or alkylation, and for the carboxyl group, esterification or amidification, or the like.

Candidate modulators which may be screened according to the methods of the invention include receptors, enzymes, ligands, regulatory factors, and structural proteins. Candidate modulators also include nuclear proteins, cytoplasmic proteins, mitochondrial proteins, secreted proteins, plasmalemma-associated proteins, serum proteins, viral antigens, bacterial antigens, protozoal antigens and parasitic antigens. Candidate modulators additionally comprise proteins, lipoproteins, glycoproteins, phosphoproteins and nucleic acids (e.g., RNAs such as ribozymes or antisense nucleic acids). Proteins or polypeptides which can be screened using the methods of the present invention include hormones, growth factors, neurotransmitters, enzymes, clotting factors, apolipoproteins, receptors, drugs, oncogenes, tumor antigens, tumor suppressors, structural proteins, viral antigens, parasitic antigens, bacterial antigens and antibodies (see below).

Candidate modulators which may be screened according to the invention also include substances for which a test cell or organism might be deficient or that might be clinically effective in higher-than-normal concentration as well as those that are designed to eliminate the translation of unwanted proteins. Nucleic acids of use according to the invention not only may encode the candidate modulators described above, but may eliminate or encode products which eliminate deleterious proteins. Such nucleic acid sequences are antisense RNA and ribozymes, as well as DNA expression constructs that encode them. Note that antisense RNA molecules, ribozymes or genes encoding them may be administered to a test cell or organism by a method of nucleic acid delivery that is known in the art, as described below. Inactivating nucleic acid sequences may encode a ribozyme or antisense RNA specific for the a target MRNA. Ribozymes of the hammerhead class are the smallest known, and lend themselves both to in vitro production and delivery to cells (summarized by Sullivan, 1994, *J. Invest. Dermatol.*, 103: 85S–98S; Usman et al., 1996, *Curr. Opin. Struct. Biol.*, 6: 527–533).

As stated above, antibodies are of use in the invention as modulators (specifically, as inhibitors) of protein kinases and/or phosphatases. Methods for the preparation of antibodies are well known in the art, and are briefly summarized as follows:

Either recombinant proteins or those derived from natural sources can be used to generate antibodies using standard techniques, well known to those in the field. For example, the proteins are administered to challenge a mammal such as a monkey, goat, rabbit or mouse. The resulting antibodies can be collected as polyclonal sera, or antibody-producing cells from the challenged animal can be immortalized (e.g. by fusion with an immortalizing fusion partner) to produce monoclonal antibodies.

1. Polyclonal antibodies.

The antigen protein may be conjugated to a conventional carrier in order to increases its immunogenicity, and an antiserum to the peptide-carrier conjugate is raised. Coupling of a peptide to a carrier protein and immunizations may be performed as described (Dymecki et al., 1992, *J. Biol. Chem.*, 267: 4815–4823). The serum is titered against protein antigen by ELISA (below) or alternatively by dot or spot blotting (Boersma and Van Leeuwen, 1994, *J. Neurosci.*

*Methods*, 51: 317). At the same time, the antiserum may be used in tissue sections prepared as described below. The serum is shown to react strongly with the appropriate peptides by ELISA, for example, following the procedures of Green et al., 1982, *Cell*, 28: 477–487.

2. Monoclonal antibodies.

Techniques for preparing monoclonal antibodies are well known, and monoclonal antibodies may be prepared using a candidate antigen whose level is to be measured or which is to be either inactivated or affinity-purified, preferably bound to a carrier, as described by Amheiter et al., *Nature*, 294, 278–280 (1981).

Monoclonal antibodies are typically obtained from hybridoma tissue cultures or from ascites fluid obtained from animals into which the hybridoma tissue is introduced. Nevertheless, monoclonal antibodies may be described as being "raised to" or "induced by" a protein.

Monoclonal antibody-producing hybridomas (or polyclonal sera) can be screened for antibody binding to the target protein. By antibody, we include constructions using the binding (variable) region of such an antibody, and other antibody modifications. Thus, an antibody useful in the invention may comprise a whole antibody, an antibody fragment, a polyfunctional antibody aggregate, or in general a substance comprising one or more specific binding sites from an antibody. The antibody fragment may be a fragment such as an Fv, Fab or F(ab')$_2$ fragment or a derivative thereof, such as a single chain Fv fragment. The antibody or antibody fragment may be non-recombinant, recombinant or humanized. The antibody may be of an immunoglobulin isotype, e.g., IgG, IgM, and so forth. In addition, an aggregate, polymer, derivative and conjugate of an immunoglobulin or a fragment thereof can be used where appropriate.

Determination of activity of candidate modulator of a protein kinase or phosphatase A candidate modulator of the activity of a protein kinase or phosphatase may be assayed according to the invention as described herein, is determined to be effective if its use results in a difference of about 10% or greater relative to controls in which it is not present (see below) in FRET resulting from the association of a labeled natural binding domain, sequence or polypeptide and its binding partner in the presence of a protein-modifying enzyme.

The level of activity of a candidate modulator may be quantified using any acceptable limits, for example, via the following formula:

$$\text{Percent Modulation} = \frac{(\text{Index}_{Control} - \text{Index}_{Sample})}{(\text{Index}_{Control})} \times 100$$

where Index$_{Control}$ is the quantitative result (e.g., amount of- or rate of change in fluorescence at a given frequency, rate of molecular rotation, FRET, rate of change in FRET or other index of modification, including, but not limited to, enzyme inhibition or activation) obtained in assays that lack the candidate modulator (in other words, untreated controls), and Indexsample represents the result of the same measurement in assays containing the candidate modulator. As described below, control measurements are made with differentially labeled natural binding domains, sequences or polypeptides and their binding partners only, and then with these molecules plus a protein kinase or phosphatase which recognizes a phosphorylation site present on them.

Such a calculation is used in either in vitro or in vivo assays performed according to the invention.

B. In vivo assays of enzymatic activity according to the invention

Reporter group protein modification in living cells

Differentially-labeled natural binding domains, sequences or polypeptides and their corresponding binding partners of the invention are delivered (e.g., by microinjection) to cells, such as smooth muscle cells (DDTI) or ventricular cardiac myocytes as previously described (Riabowol et al., 1988, *Cold Spring Harbor Symposia on Quantitatve Biology*, 53: 85–90). The ratio of emission from the labeled molecule(s) is measured as described above via a photomultiplier tube focused on a single cell. Activation of a kinase (e.g., PKA by the addition of dibutyryl cAMP or P-adrenergic agonists) is performed, subsequent inhibition is performed by removal of stimulus and by addition of a suitable antagonist (e.g., cAMP antagonist Rp-cAMPS).

Heterologous expression of peptides

Natural binding domains, sequences or polypeptides and/ or their binding partners can be produced from the heterologous expression of DNA sequences that encode them or by chemical synthesis of the same. Expression can be in procaryotic or eukaryotic cells using a variety of plasmid vectors capable of instructing heterologous expression. Purification of these products is achieved by destruction of the cells (e.g. French Press) and chromatographic purification of the products. This latter procedure can be simplified by the inclusion of an affinity purification tag at one extreme of the peptide, separated from the peptide by a protease cleavage site if necessary.

The use of cells or whole organisms in assays of the invention

When performed using cells, the assays of the invention are broadly applicable to a host cell susceptible to transfection or transformation including, but not limited to, bacteria (both gram-positive and gram-negative), cultured- or explanted plant (including, but not limited to, tobacco, arabidopsis, carnation, rice and lentil cells or protoplasts), insect (e.g., cultured Drosophila or moth cell lines) or vertebrate cells (e.g., mammalian cells) and yeast.

Organisms are currently being developed for the expression of agents including DNA, RNA, proteins, non-proteinaceous compounds, and viruses. Such vector microorganisms include bacteria such as Clostridium (Parker et al., 1947, *Proc. Soc. Exp. Biol. Med.*, 66: 461–465; Fox et al., 1996, GeneTherapy, 3: 173–178; Minton et al., 1995, FEMS Microbiol. Rev., 17: 357–364), Salmonella (Pawelek et al., 1997, *Cancer Res.*, 57: 4537–4544; Saltzman et al., 1996, Cancer Biother. Radiopharm., 11: 145–153; Carrier et al., 1992, J. Immunol., 148: 1176–1181; Su et al., 1992, *Microbiol. Pathol.*, 13: 465–476; Chabalgoity et al., 1996, *Infect. Immunol.*, 65: 2402–2412), Listeria (Schafer et al., 1992, *J. Immunol.*, 149: 53–59; Pan et al., 1995, *Nature Med.*, 1: 471–477) and Shigella (Sizemore et al., 1995, *Science*, 270: 299–302), as well as yeast, mycobacteria, slime molds (members of the taxa Dictyosteliida—such as of the genera Polysphondylium and Dictystelium, e.g. *Dictyostelium discoideum*—and Myxomycetes—e.g. of the genera Physarum and Didymium) and members of the Domain Arachaea (including, but not limited to, archaebacteria), which have begun to be used in recombinant nucleic acid work, members of the phylum Protista, or other cell of the algae, fungi, or any cell of the animal or plant kingdoms.

Plant cells useful in expressing polypeptides of use in assays of the invention include, but are not limited to, tobacco (Nicotiana plumbaginifolia and Nicotiana tabacum), arabidopsis (Arabidopsis thaliana), Aspergillus niger, Brassica napus, Brassica nigra, Datura innoxia, Vicia narbonensis, Viciafaba, pea (Pisum sativum), cauliflower, carnation and lentil (Lens culinaris). Either whole plants, cells or protoplasts may be transfected with a nucleic acid of choice. Methods for plant cell transfection or stable transformation include inoculation with Agrobacterium tumefaciens cells carrying the construct of interest (see, among others, Turpen et al., 1993, I-.VLirol.Mitllds, 42: 227- 239), administration of liposome-associated nucleic acid molecules (Maccarrone et al., 1992, Biochem.BiophysRes.Corinun., 186: 1417–1422) and microparticle injection (Johnston and Tang, 1993, *Genet. Eng. (NY)*, 15: 225–236), among other methods. A generally useful plant transcriptional control element is the cauliflower mosaic virus (CaMV) 35S promoter (see, for example, Saalbach et al., 1994, *Mol. Gen. Genet.*, 242: 226–236). Non-limiting examples of nucleic acid vectors useful in plants include pGSGLUCl (Saalbach et al., 1994, supra), pGA492 (Perez et al., 1989, *Plant. Mol. Biol.*, 13: 365–373), pOCA18 (Olszewski et al., 1988, *Nucleic. Acids Res.*, 16: 10765–10782), the Ti plasmid (Roussell et al., 1988, *Mol. Gen. Genet.*, 211: 202–209) and pKR612B1 (Balazs et al., 1985, *Gene*, 40: 343–348).

Mammalian cells are of use in the invention. Such cells include, but are not limited to, neuronal cells (those of both primary explants and of established cell culture lines) cells of the immune system (such as T-cells, B-cells and macrophages), fibroblasts, hematopoietic cells and dendritic cells. Using established technologies, stem cells (e.g. hematopoietic stem cells) may be used for gene transfer after enrichment procedures. Alternatively, unseparated hematopoietic cells and stem cell populations may be made susceptible to DNA uptake. Transfection of hematopoietic stem cells is described in Mannion-Henderson et al., 1995, *Exp. Hemato.*, 23: 1628; Schiffmann et al., 1995, *Blood, 86:* 1218; Williams, 1990, *Bone Marrow Transplant*, 5: 141; Boggs, 1990, *Int. J. Cell Cloning*, 8: 80; Martensson et al., 1987, *Eur. J. Immunol,.* 17: 1499; Okabe et al., 1992, *Eur. J. Immunol.*, 22: 37–43; and Banerji et al., 1983, *Cell*, 33: 729. Such methods may advantageously be used according to the present invention.

Nucleic acid vectors for the expression of assay components of the invention in cells or multicellular organisms A nucleic acid of use according to the methods of the invention may be either double- or single stranded and either naked or associated with protein, carbohydrate, proteoglycan and/or lipid or other molecules. Such vectors may contain modified and/or unmodified nucleotides or ribonucleotides. In the event that the gene to be transfected may be without its native transcriptional regulatory sequences, the vector must provide such sequences to the gene, so that it can be expressed once inside the target cell. Such sequences may direct transcription in a tissue-specific manner, thereby limiting expression of the gene to its target cell population, even if it is taken up by other surrounding cells. Alternatively, such sequences may be general regulators of transcription, such as those that regulate housekeeping genes, which will allow for expression of the transfected gene in more than one cell type; this assumes that the majority of vector molecules will associate preferentially with the cells of the tissue into which they were injected, and that leakage of the vector into other cell types will not be significantly deleterious to the recipient organism. It is also possible to design a vector that will express the gene of choice in the Target cells at a specific time, by using an inducible promoter, which will not direct transcription unless a specific stimulus, such as heat shock, is applied.

A gene encoding a component of the assay system of the invention or a candidate modulator of protein kinase or phosphatase activity may be transfected into a cell or organism using a viral or non-viral DNA or RNA vector, where non-viral vectors include, but are not limited to, plasmids, linear nucleic acid molecules, artificial chromomosomes and episomal vectors. Expression of heterologous genes in mammals has been observed after injection of plasmid DNA into muscle (Wolff J. A. et al., 1990, *Science*, 247: 1465–1468; Carson D. A. et al., U.S. Pat. No. 5,580, 859), thyroid (Sykes et al. 1994, *Human Gene Ther.*, 5: 837–844), melanoma (Vile et al., 1993, *Cancer Res.*, 53: 962–967), skin (Hengge et al., 1995, Nature Genet., 10: 161–166), liver (Hickman et al., 1994, Human Gene Therapy, 5: 1477–1483) and after exposure of airway epithelium (Meyer et al., 1995, *Gene Therapy*, 2: 450–460).

In addition to vectors of the broad classes described above and fusion gene expression construct encoding a natural binding domain, sequence or polypeptide fused in-frame to a fluorescent protein, as described above (see "Fluorescent resonance energy transfer"), microbial plasmids, such as those of bacteria and yeast, are of use in the invention.

Bacterial plasmids:

Of the frequently used origins of replication, pBR322 is useful according to the invention, and pUC is preferred. Although not preferred, other plasmids which are useful according to the invention are those which require the presence of plasmid encoded proteins for replication, for example, those comprising pT181, FII, and Fl origins of replication.

Examples of origins of replication which are useful in assays of the invention in *E. coli* and *S. typhimurium* include but are not limited to, pHETK (Garapin et al., 1981, *Proc. Natl. Acad. Sci U.S.A*, 78: 815–819), p279 (Talmadge et al., 1980, *Proc. Natl. Acad. Sci. U.SA.*, 77: 3369–3373), p5–3 and p21A-2 (both from Pawalek et al., 1997, *Cancer Res.*, 57: 4537–4544), pMB1 (Bolivar et al., 1977, *Gene*, 2: 95–113), ColEl (Kahn et al., 1979, *Methods Enzymol.*, 68: 268–280), p15A (Chang et al., 1978, *J. Bacteriol*, 134: 1141–1156); pSC101 (Stoker et al., 1982, *Gene*, 18: 335–341); R6K (Kahn et al., 1979, supra); R1 (temperature dependent origin of replication, Uhlin et al., 1983, *Gene*, 22: 255–265); lambda dv (Jackson et al., 1972, *Proc. Nat. Aca. Sci. U.S.A.*, 69: 2904–2909); pYA (Nakayama et al., 1988, infra). An example of an origin of replication that is useful in Staphylococcus is pT181 (Scott, 1984, *Microbial Reviews* 48: 1–23). Of the above-described origins of replication, pMB 1, p15A and ColEI are preferred because these origins do not require plasmid-encoded proteins for replication.

Yeast plasmids:

Three systems are used for recombinant plasmid expression and replication in yeasts:

1. Integrating. An example of such a plasmid is YIp, which is maintained at one copyper haploid genome, and is inherited in Mendelian fashion. Such a plasmid, containing a gene of interest, a bacterial origin of replication and a selectable gene (typically an antibiotic-resistance marker), is produced in bacteria. The purified vector is linearized within the selectable gene and used to transform competent yeast cells. Regardless of the type of plasmid used, yeast cells are typically transformed by chemical methods (e.g. as described by Rose et al., 1990, *Methods in Yeast Genetics*, Cold Spring Harbor Laboratory Press, Cold Spring Harbor, N.Y.). The cells are treated with lithium acetate to achieve transformation efficiencies of approximately $10^4$ colony-forming units (transformed cells)/μg of DNA. Yeast perform homologous recombination such that the cut, selectable marker recombines with the mutated (usually a point mutation or a small deletion) host gene to restore function. Transformed cells are then isolated on selective media.

2. Low copy-number ARS-CEN, of which YCp is an example. Such a plasmid contains the autonomous replicating sequence (ARS1), a sequence of approximately 700 bp which, when carried on a plasmid, permits its replication in yeast, and a centromeric sequence (CEN4), the latter of which allows mitotic stability. These are usually present at 1–2 copies per cell. Removal of the CEN sequence yields a YRp plasmid, which is typically present in 100–200 copes per cell; however, this plasmid is both mitotically and meioticaily unstable.

3. High-copy-number 2 μ circles. These plasmids contain a sequence approximately 1 kb in length, the 2μ sequence, which acts as a yeast replicon giving rise to higher plasmid copy number; however, these plasmids are unstable and require selection for maintenance. Copy number is increased by having on the plasmid a selection gene operatively linked to a crippled promoter. This is usually the LEU2 gene with a truncated promoter (LEU2-d), such that low levels of the Leu2p protein are produced; therefore, selection on a leucine-depleted medium forces an increase in copy number in order to make an amount of Leu2p sufficient for cell growth.

As suggested above, examples of yeast plasmids use fill in the invention include the YRp plasmids (based on autonomously-replicating sequences, or ARS) and the YEp plasmids (based on the 2 μ circle), of which examples are YEp24 and the YEplac series of plasmids (Gietz and Sugino, 1988, *Gene*, 74: 527–534). (See Sikorski, "Extrachromosomal cloning vectors of *Saccharomyces cerevisiae*", in *Plasmids, A Practical Approach*, Ed. K. G. Hardy, IRL Press, 1993; and *Yeast Clonig Vectors and Genes Current Protocols in Molecular Biology*, Section II, Unit 13.4, Eds., Ausubel et al., 1994).

In addition to a yeast origin of replication, yeast plasmid sequences typically comprise an antibiotic resistance gene, a bacterial origin of replication (for propagation in bacterial cells) and a yeast nutritional gene for maintenance in yeast cells. The nutritional gene (or "auxotrophic marker") is most often one of the following (with the gene product listed in parentheses and the sizes quoted encompassing the coding sequence, together with the promoter and terminator elements required for correct expression):

TRP1 (PhosphoADP-ribosylanthranilate isomerase, which is a component of the tryptophan biosynthetic pathway).

URA3 (Orotidine-5'-phosphate decarboxylase, which takes part in the uracil biosynthetic pathway).

LEU2 (3-Isopropylmalate dehydrogenase, which is involved with the leucine biosynthetic pathway).

HIS3 (Imidazoleglycerolphosphate dehydratase, or IGP dehydratase).

LYS2 (α-aminoadipate-semialdehyde dehydrogenase, part of the lysine biosynthetic pathway).

Alternatively, the screening system may operate in an intact, living multicellular organism, such as an insect or a mammal. Methods of generating transgenic Drosophila, mice and other organisms, both transiently and stably, are well known in the art; detection of fluorescence resulting from the expression of Green Fluorescent Protein in live Drosophila is well known in the art. One or more gene expression constructs encoding one or more of a labeled natural binding domain, sequence or polypeptide, a binding partner, a protein kinase or phosphatase and, optionally, a candidate modulator thereof are introduced into the test organism by methods well known in the art (see also below). Sufficient time is allowed to pass after administration of the nucleic acid molecule to allow for gene expression, for binding of a natural binding domain, sequence or polypeptide to its binding partner and for chromophore maturation, if necessary (e.g., Green Fluorescent Protein matures over a period of approximately 2 hours prior to fluorescence) before FRET is measured. A reaction component (particularly a candidate modulator of enzyme function) which is not administered as a nucleic acid molecule may be delivered by a method selected from those described below.

Dosage and administration of a labeled natural binding domain, sequence or polypeptide, binding partner therefor, protein kinase or phosphatase or canditate modulator thereof for use in an in vivo assay of the invention Dosage For example, the amount of each labeled natural binding domain or binding partner therefor must fall within the detection limits of the fluorescence-measuring device employed. The amount of an enzmye or candidate modulator thereof will typically be in the range of about 1 μg–100 mg/kg body weight. Where the candidate modulator is a peptide or polypeptide, it is typically administered in the range of about 100–500 μg/ml per dose. A single dose of a candidate modulator, or multiple doses of such a substance, daily, weekly, or intermittently, is contemplated according to the invention.

A candidate modulator is tested in a concentration range that depends upon the molecular weight of the molecule and the type of assay. For example, for inhibition of protein/protein or protein/DNA complex formation or transcription initiation (depending upon the level at which the candidate modulator is thought or intended to modulate the activity of a protein kinase or phosphatase according to the invention), small molecules (as defined above) may be tested in a concentration range of 1 pg–100 μg/ml, preferably at about 100 pg–10 ng/ml; large molecules, e.g., peptides, may be tested in the range of 10 ng–100 μμg/ml, preferably 100 ng–10 μg/ml.

Administration

Generally, nucleic acid molecules are administered in a manner compatible with the dosage formulation, and in such amount as will be effective. In the case of a recombinant nucleic acid encoding a natural binding domain and/or binding partner therefor, such an amount should be sufficient to result in production of a detectable amount of the labeled protein or peptide, as discussed above. In the case of a protein kinase or phosphatase, the amount produced by expression of a nucleic acid molecule should be sufficient to ensure that at least 10% of natural binding domains or binding partners therefor will undergo modification if they comprise a target site recognized by the enzyme being assayed. Lastly, the amount of a nucleic acid encoding a candidate modulator of a protein kinase or phosphatase of the invention must be sufficient to ensure production of an amount of the candidate modulator which can, if effective, produce a change of at least 10% in the effect of the target protein kinase or phosphatase on FRET or other label emission resulting from binding of a natural binding domain to its binding partner or, if administered to a patient, an amount which is prophylactically and/or therapeutically effective.

When the end product (e.g. an antisense RNA molecule or ribozyme) is administered directly, the dosage to be administered is directly proportional to the amount needed per cell and the number of cells to be transfected, with a correction factor for the efficiency of uptake of the molecules. In cases in which a gene must be expressed from the nucleic acid molecules, the strength of the associated transcriptional regulatory sequences also must be considered in calculating the number of nucleic acid molecules per target cell that will result in adequate levels of the encoded product. Suitable dosage ranges are on the order of, where a gene expression construct is administered, 0.5- to 1 µg, or 10 µg, or optionally 10–100 µg of nucleic acid in a single dose. It is conceivable that dosages of up to 1mg may be advantageously used. Note that the number of molar equivalents per cell vary with the size of the construct, and that absolute amounts of DNA used should be adjusted accordingly to ensure adequate gene copy number when large constructs are injected.

If no effect (e.g., of a protein kinase or phosphatase or an inhibitor thereof) is seen within four orders of magnitude in either direction of the starting dosage, it is likely that a protein kinase or phosphatase does not recognize the target site of the natural binding domain (and, optionally, its binding partner) according to the invention, or that the candidate modulator thereof is not of use according to the invention. It is critical to note that when high dosages are used, the concentration must be kept below harmful levels, which may be known if an enzyme or candidate modulator is a drug that is approved for clinical use. Such a dosage should be one (or, preferably, two or more) orders of magnitude below the $LD_{50}$ value that is known for a laboratory mammal, and preferably below concentrations that are documented as producing serious, if non-lethal, side effects.

Components of screening assays of the invention may be formulated in a physiologically acceptable diluent such as water, phosphate buffered saline, or saline, and further may include an adjuvant. Adjuvants such as incomplete Freund's adjuvant, aluminum phosphate, aluminum hydroxide, or alum are materials well known in the art. Administration of labeled polypeptides comprising a natural binding domain, sequence, polypeptide or a binding partner therefor, a protein kinase or phosphatase or a candidate modulator as described herein may be either localized or systemic.

Localized administration:

Localized administration of a component of an assay of the invention is preferably by via injection or by means of a drip device, drug pump or drug-saturated solid matrix from which the labeled natural binding domain, sequence or polypeptide, binding partner therefor, protein kinase or phosphatase or candidate modulator therefor, or nucleic acid encoding any of these can diffuse implanted at the target site. When a tissue that is the target of delivery according to the invention is on a surface of an organism, topical administration of a pharmaceutical composition is possible.

Compositions comprising a composition of- or of use in the invention which are suitable for topical administration can take one of several physical forms, as summarized below:

(i) A liquid, such as a tincture or lotion, which may be applied by pouring, dropping or "painting" (i.e. spreading manually or with a brush or other applicator such as a spatula) or injection.

(ii) An ointment or cream, which may be spread either manually or with a brush or other applicator (e.g. a spatula), or may be extruded through a nozzle or other small opening from a container such as a collapsible tube.

(iii) A dry powder, which may be shaken or sifted onto the target tissue or, alternatively, applied as a nebulized spray.

(iv) A liquid-based aerosol, which may be dispensed from a container selected from the group that comprises pressure-driven spray bottles (such as are activated by squeezing), natural atomizers (or "pump-spray" bottles that work without a compressed propellant) or pressurized canisters.

(v) A carbowax or glycerin preparation, such as a suppository, which may be used for rectal or vaginal administration of a therapeutic composition.

In a specialized instance, the tissue to which a candidate modulator of a protein kinase or phosphatase is to be delivered for assay (or, if found effective, for therapeutic use) is the lung. In such a case the route of administration is via inhalation, either of a liquid aerosol or of a nebulized powder of. Drug delivery by inhalation, whether for topical or systemic distribution, is well known in the art for the treatment of asthma, bronchitis and anaphylaxis. In particular, it has been demonstrated that it is possible to deliver a protein via aerosol inhalation such that it retains its native activity in vivo (see Hubbard et al., 1989, *J. Clin. Invest.*, 84: 1349–1354).

Systemic administration:

Systemic administration of a protein, nucleic acid or other agent according to the invention may be performed by methods of whole-body drug delivery are well known in the art. These include, but are not limited to, intravenous drip or injection, subcutaneous, intramuscular, intraperitoneal, intracranial and spinal injection, ingestion via the oral route, inhalation, trans-epithelial diffusion (such as via a drug-impregnated, adhesive patch) or by the use of an implantable, time-release drug delivery device, which may comprise a reservoir of exogenously-produced protein, nucleic acid or other material or may, instead, comprise cells that produce and secrete a natural binding domain and/or a binding partner therefor, protein kinase or phosphatase or candidate modulator thereof. Note that injection may be performed either by conventional means (i.e. using a hypodermic needle) or by hypospray (see Clarke and Woodland, 1975, *Rheumatol. Rehabil.*, 14: 47–49). Components of assays of the invention can be given in a single- or multiple dose.

Delivery of a nucleic acid may be performed using a delivery technique selected from the group that includes, but is not limited to, the use of viral vectors and non-viral vectors, such as episomal vectors, artificial chromosomes, liposomes, cationic peptides, tissue-specific cell transfection and transplantation, administration of genes in general vectors with tissue-specific promoters, etc.

Kits According to the Invention

A kit for assaying the activity of a protein kinase or phoshatase

In order to facilitate convenient and widespread use of the invention, a kit is provided which contains the essential components for screening the activity of a protein kinase or phosphatase, as described above. A natural binding domain, sequence or polypeptide, as defined above, and its corresponding binding partner are provided, as is a suitable reaction buffer for in vitro assay or, alternatively, cells or a cell lysate. A reaction buffer which is "suitable" is one which is permissive of the activity of the enzyme to be assayed and which permits phosphorylation-dependent binding of the natural binding domain to the binding partner. The labeled polypeptide components are provided as peptide/protein or a nucleic acid comprising a gene expression construct encoding the one or more of a peptide/protein, as discussed above. Natural binding domains, sequences and polypeptides, as well as their corresponding binding partners, are supplied in a kit of the invention either in solution (preferably refrigerated or frozen) in a buffer which inhibits degradation and maintains biological activity, or are provided in dried form, i.e., lyophilized. In the latter case, the components are resuspended prior to use in the reaction buffer or other biocompatible solution (e.g. water, containing one or more of physiological salts, a weak buffer, such as phosphate or Tris, and a stabilizing substance such as glycerol, sucrose or polyethylene glycol); in the latter case, the resuspension buffer should not inhibit phosphorylation-dependent binding of the natural binding domain, sequence or polypeptide with the binding partner when added to the reaction buffer in an amount necessary to deliver sufficient protein for an assay reaction. Natural binding domains, sequences or polypeptides or their binding partners provided as nucleic acids are supplied- or resuspended in a buffer which permits either transfection/transformation into a cell or organism or in vitro transcription/translation, as described above. Each of these components is supplied separately contained or in admixture with one or more of the others in a container selected from the group that includes, but is not limited to, a tube, vial, syringe or bottle.

Optionally, the kit includes cells. Eukaryotic or prokaryotic cells, as described above, are supplied in- or on a liquid or solid physiological buffer or culture medium (e.g. in suspension, in a stab culture or on a culture plate, e.g. a Petri dish). For ease of shipping, the cells are typically refrigerated, frozen or lyophilized in a bottle, tube or vial. Methods of cell preservation are widely known in the art; suitable buffers and media are widely known in the art, and are obtained from commerical suppliers (e.g., Gibco/LifeTechnologies) or made by standard methods (see, for example Sambrook et al., 1989, *Molecular Cloning. A Laboratory Manual.*, 2nd Eddition, Cold Spring Harbor Laboratory Press, Cold Spring Harbor, N.Y.).

An enzyme being assayed according to the invention is added to the assay system either as a protein (isolated, partially-purified or present in a crude preparation such as a cell extract or even a living cell) or a recombinant nucleic acid. Methods of expressing a nucleic acid comprising an enzyme or other protein are well known in the art (see again above).

An assay of the invention is carried out using the kit according to the methods described above and in the Examples.

A kit for screening a candidate modulator of protein kinase or phosphatase activity according to the invention A candidate modulator of post-translational phosphorylation or dephosphorylation may be assayed using a kit of the invention. A kit as described above is used for this application, with the assay performed further comprising the addition of a candidate modulator of the protein kinase or phosphatase which is present to the reaction system. Optionally, a protein kinase or phosphatase is supplied with the kit, either as a protein or nucleic acid as described above.

Assays of protein activity are performed as described above. At a minimum, three detections are performed, one in which the natural binding domain and binding partner are present without the protein kinase or phosphatase or candidate modulator thereof (control reaction A), one in which the polypeptides are incubated with the modifying enzyme under conditions which permit the phosphorylation or dephosphorylation reaction to occur (control reaction B) and one in which the protein kinase or phosphatase and candidate modulator are both incubated with the labeled polypeptides under conditions which permit the modification reaction to occur (test reaction). In each case, conditions are suitable to permit phosphorylation-dependent association of the natural binding domain, sequence or polypeptide and the binding partner. The result of the last detection procedure is compared with those of the two controls; the candidate modulator is judged to be efficacious if there is a shift in either of the observed amount of signal (i.e., total amount- or rate of change of fluorescence, FRET, mass of a protein complex or inhibition or activation of an enzyme) of at least 10% away from that observed in control reaction B toward that observed in control reaction A.

EXAMPLE 1

Use of a polypeptide comprising a natural binding domain as a phosphorylation reporter according to the invention: Assay 1

An assay of this type involves the following components:

v-Src SH2 domain (amino acids 148–246; Waksman et al., 1993, *Cell*, 72: 779–790; OWL database accession no. M33292), and Hamster polyomavirus middle T antigen (Ag, below) (321–331, EPQYEEIPIYL, SEQ ID NO: 4; Waksman et al., 1993, supra; OWL database accession no. P03079).

SH2 domains are found in proteins involved in a number of signalling pathways and their binding to specific phosphorylated tyrosine residues is key in mediating the transmission of signals between tyrosine kinases and the proteins in the cell which respond to tyrosine phosphorylation (Waksman et al., 1993, supra and references therein). Individual SH2 domains recognize specific sequences, and the sequence specificity of a number of SH2 domains has been determined (Songyang et al., 1993, supra) using a phosphopeptide library. These data provide a number of possible domain/peptide pairs which are useful in assays of enzymatic activity according to the invention. The crystal structure of the Src SH2 domain complexed with a peptide containing its specific recognition motif from the hamster middle-T antigen (target tyrosine for phosphorylation shown in bold above) has been determined by Waksman et. al.(Cell 72, 779–790). Thus, the assay is:

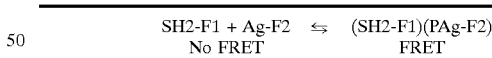

F1 is the donor fluorophore, F2 the acceptor fluorophore and P denotes the addition of a phosphate group to the target tyrosine residue.

The peptide as used in the crystallization described above does not contain suitable residues for convenient labelling, and a label within this short sequence is too close to the phosphorylation site. A short linker (e.g., Gly-Gly) is, therefore, added to either the C- or N-terminus of the peptide with a residue such as Lys for labelling on the end. The location of this linker will depend upon the location of F1 in the SH2 domain.

A number of potential locations for the fluorophore in the SH2 domain have been identified based upon crystal structure:

| SH2 Domain | Middle T Ag. peptide |
|---|---|
| K 232 | C-terminal extension (G-G-K or similar) |
| R 217 | C-terminal extension |
| K 181 | N-terminal extension |
| R 156** | N-terminal extension |

**this site is close to the site of peptide interaction

If a fluorescent protein (e.g., Green Fluorescent Protein, GFP) is used instead of a chemical fluorophore, it is placed at the N-termini of both the SH2 domain and the peptide

EXAMPLE 2
Use of apolypeptide comprising a natural bindmg domain as a phosphorylation reporter according to the invention: Assay 2

This assay involves the following components:
PTB domain of IRS-1 (amino acids 157–267) (Zhou et al., 1996, *Nature Stuctural Biology*, 3: 388–393; OWL accession no. P35568), and
Interleukin 4 Receptor (IL-4R) (amino acids 489–499, LVIAGNPAYRS, SEQ ID NO:5; Zhou et. al., 1996, supra; OWL accession no. P24394) Phosphotyrosine binding (PTB) domains are found in a number of proteins involved in signalling pathways utilizing tyrosine phosphorylation. The PTB domain has functional similarities to the SH2 domain but differs in its mechanism of action and structure, as well as in sequence recognition (Laminet et al., 1996, *J. Biol, Chem.*, 271: 264–269; Zhou et. al., 1996, supra and references therein). These two classes of domain have little sequence identity. NMR structural analysis of the PTB domain of IRS- 1 complexed with the IL-4 receptor peptide has been performed (Zhou et al., 1996, supra).

The assay format is as follows:

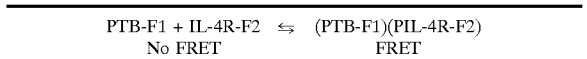

F1 is the donor fluorophore, F2 the acceptor fluorophore, and P denotes the addition of a phosphate group to the target tyrosine residue.

The peptide of the NMR study described above does not contain suitable residues for convenient labelling except the arginine next to the phosphorylation site, and a label within this short sequence may be too close to the target site for phosphorylation. A short linker may be added to either the C- or N-terminus of the peptide with a residue for labelling on the end. The location of such a linker depends upon the location of F1 in the PTB domain.

Several potential locations for the fluorophore in the PTB sequence have been identified from the NMR structure:

| PTB domain | IL-4R peptide |
|---|---|
| K161 | N-terminal extension (G-G-K or similar) |
| K190 | N-terminal extension |
| N-terminal extension | N-terminal extension |
| C-terminal extension | C-terminal extension |

Again, if GFP is used in lieu of a chemical fluorophore, it can be fused in-frame to either the N- or C-terminus of both the PTB sequence and the binding partner.

EXAMPLE 3
An assay analogous to that in Example 2 can be configured according to the invention using the PTB domain of the proto-oncogene product Cbl and a peptide derived from the Zap-70 tyrosine kinase. The Cbl phosphotyrosine-binding domain selects a D(N/D)XpY motif and binds to the $Tyr_{292}$ negative regulatory phosphorylation site of ZAP-70 (Lupher et al., 1997, *J. Biol. Chem.*, 272: 33140–33144).

The components of the assay are:
The Cbl N-terminal domain (amino acids 1–357; Lupher et al., 1996, J. Biol. Chem., 271: 24063–24068; OWL accession no. P22681), and
Zap-70 (amino acids 284–299, $NH_3$-IDTLNSDGYTPEPARI-COOH, SEQ ID NO:6; Lupher et. al., 1996, supra; OWL accession no. P43403)

EXAMPLE 4
Use of a polypeptide comprising a natural binding domain as a phosphorylation reporter according to the invention: Assay 4

This assay involves the following component-c-Src (residues 86–536; Xu et al., 1997, *Nature*, 385: 595–602; *GenBank Accession No. K*03218).

As stated above, Src is a member of a family of non-receptor tyrosine kinases involved in the regulation of responses to extracellular signals. Association of src with both the plasma membrane and intracellular membranes is mediated by myristoylation at the N-terminus. The enzyme has four regions which are conserved throughout the family, the SH2 domain, the SH3 domain, the kinase or SH1 domain and the C-terminal tail. In addition there is a unique region which does not have homology between family members (Brown and Cooper, 1996, BiochimBiophysActa, 1287: 121–149).

The SH2 domain binds tightly to specific tyrosine phosphorylated sequences. This affinity plays a role in the interaction between src and other cellular proteins and also in the regulation of the kinase by phosphorylation. The C-terminal tail of src can be s phosphorylated on $Tyr_{30}$, which phosphorylation leads to almost complete inhibition of kinase activity. There is strong evidence that this inhibition is achieved by the interaction of the C-terminal tail with the SH2 domain. This interaction is thought to promote a conformational change to the 'closed' conformation which is further stabilized by the participation of the SH3 and kinase domains in intramolecular contacts.

The assay is diagramed as follows:

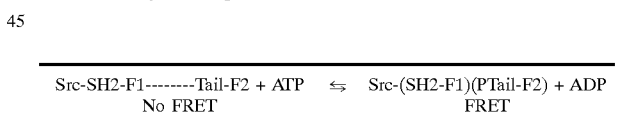

where F1 is the donor fluorophore, F2 is the acceptor fluorophore and P denotes the addition of a phosphate group to the target tyrosine residue.

There are several potential sites for labelling in this structure. Some examples of target residues are shown below:

| C-Terminal tail | SH2 domain |
|---|---|
| E527 | D195, K198 |
| C-Terminal extension (eg. Gly-Gly-Lys) | R220, K235, |

When a fluorescent protein is used in an assay such as this, using an intramolecular interaction to follow chemical modification, it is appropriate to place GFP between domains using a flexible linker to preserve protein domain interactions. This allows the GFP variants to approach more closely and increase the efficiency of the FRET achieved, but must be balanced by the need to achieve a good distance between variants in the 'No FRET' state. If sufficient spacing between donor and acceptor fluorophores or, alternatively, between a fluorophore or other label and a quencher therefor, is not achieved in this manner, other candidate locations for fluorescent protein fusion include, but are not limited to, the C-terminus and the region between the SH2 domain and the SH2-kinase linker.

EXAMPLE 5

Solution FRET assay for Yersinia Tyrosine Phosphatase (YOP) using a natural binding partner labeled with a fluoescent protein and a synthetic peptide labelled with a chemical fluorophore The following solution based assay was performed to detect YOP activity by measuring disruption of a complex between a fluorescently labelled SH2 domain of ZAP-70 and a synthetic peptide based on the TCRC chain labelled with a chemical fluorophore.

A FRET partnership is formed between the SH2 domain of ZAP-70 and a phosphorylated peptide based on the TCRζ chain, providing both partners are labelled with suitable fluorophores. Formation of FRET is followed in real-time by adding the two binding partners together. Disruption of FRET can be achieved by the addition of a phosphatase, which removes the phosphate required for the interaction of the partners.

Methods: TCR peptide sequence Peptide 1. Phosphorylated TCRζ chain: RCKFSRSAEPPAYQQGQNQLY$_{(p)}$NELNLGRREEY$_{(p)}$DVLD, SEQ ID NO:7

Peptide labelling

Peptide 1 was labelled with rhodamine under mild conditions using thiol directed chemistry. 230 $\mu$M peptide was labelled in 2 mM TES pH 7 in the presence of a three-fold excess of rhodamine-6-maleimide (Molecular Probes). Dialysis was utilised to remove excess dye from the peptide. Labelling was verified by MALDI-TOF MS.

ZAP-GP coningand purification

DNA constructs

ZAP-GFP: Primers were designed based on the published ZAP-70 DNA sequence (Genbank accession number L05148). The SH2 domain (amino acids 1–259) of ZAP70 was cloned by PCR using the following oligo-nucleotides:

Forward primer GGGATCCATATGCCAGACCCCGCGGCGCACCTG, SEQ ID NO:8

Reverse Primer GGAATTCGGGCACTGCTGTTGGGGCAGGCCTCC, SEQ ID NO:9

The resultant PCR fragment was digested with BamHI and EcoRI and inserted into pET28a (Novagen) to generate vector pFS45. DNA encoding GFP in the vector pQBI25-FNI (Quantum) was digested with MluI and the resultant 5' overhang was "filled in" using T4 DNA polymerase (NEB). After the polymerase was denatured by heat treatment the DNA was further digested with EcoRI and the resultant 850 bp band was gel purified. The vector pFS45 was digested with HindIII and the resultant 5' overhang was "filled in" with T4 DNA polymerase and then further digested with EcoRI. After the digested vector was gel purified it was ligated with the purified DNA encoding GFP to generate pFS46 which was designed to express a ZAP70-GFP fusion protein in bacteria.

Expression and purification procedure

Fresh transformants of ZAP-GFP pET-28a in BRL(DE3) were used to inoculate 3 ml LB/kanamycin (100 $\mu$/ml). The starter cultures were incubated overnight at 37° C. with constant shaking. From these starter cultures Iml was used to inoculate 400 ml Terrific Broth/kanamycin (100 $\mu$g/ml) in a 2L, baffled flask. Cultures were incubated at 37° C. at 2 rpm for approximately 5 hrs until the OD600 nm reached 0.5Abs units. At this point cultures were induced by adding IPTG to a concentration of lmM. The cultures were then left incubating at room temperature overnight with gentle shaking on a benchtop rotator. Bacteria were harvested by centrifugation at 3000 rpm for 20 mins. The bacterial pellet was resuspended in 25 ml lysis buffer (5 mM phosphate buffer pH 7.0, 300 mM NaCl, 2% Proteinase inhibitor cocktail (Sigma), 0.75 mg/ml Lysozyme). Lysis of the resuspended cells was initiated by gentle stirring for 1hr at room temperature. The partially lysed mixture was subjected to 2 cycles of freeze thawing in liquid nitrogen. Finally the cells were sonicated on ice using a 10 mm probe at high power. Sonication was performed on a pulse setting for a period of 3 min. The crude lysate was then centrifuged at 15,000 rpm for 30 mins to remove cell debris. Hexa-His tagged proteins were purified from the clear lysate using TALON® resin (Clontech). Proteins were bound to the resin in a batchwise manner by gentle shaking at room temperature for 30 min. Non-His tagged proteins were removed by washing the resin at least twice with 10× bed volume of wash buffer (50 mM sodium phosphate pH 7.0, 3 mM NaCl, 5 mM fluorescence-blank Imidazole ). The washed resin was loaded into a 2 ml column and the bound proteins were released with elution buffer (50 mM sodium phosphate pH 7.0, 300 mM NaCl, 150 mM fluorescence-blank Imidazole). Elution was normally achieved after the first 0.5 ml and within 2–3 ml in total. Proteins were stored at −80° C after snap freezing in liquid nitrogen in the presence of 10% glycerol.

Formation of the FRET partnership

ZAP-GFP was diluted to 0.5 $\mu$M in YOP assay buffer (5 mM Tris-HCl pH 7.2, 10 mM β-mercaptoethanol, 0.5 mg/ml BSA, 0.015% Brij 35). 98 $\mu$l of this solution was used per assay. Initial readings of the fluorescence of the ZAP-GFP construct were made using 485nm excitation wavelength and 520nm emission wavelength. Rhodamine labelled peptide (2jl of a 115 $\mu$M peptide solution) was added to the ZAP-GFP and formation of FRET followed in real-time by measuring the decrease in fluorescence emission of ZAP-GFP at 520 nm.

YOP source and assay conditions

Yersinia protein tyrosine phosphatase (YOP) was purchased from Upstate Biotechnology. YOP, 3 units, was added to the ZAP-GFP/peptide FRET mixture and the increase in fluorescence emission at 520 nm, was followed in real-time as the partnership was disrupted (FIG. 4). Dependence of YOP activity on TCR peptide concentration and Km determination was measured using different concentrations of rhodamine labelled TCRζ peptide (FIG. 5).

The solution FRET assay for YOP was also used to determine the IC$_{50}$ of ortho vanadate, a general protein phosphatase inhibitor. The YOP assay was performed as above, using 3 units of YOP and incubating the enzyme with the ZAP-GFP/peptide FRET mixture at 30° C. Dephosphorylation was followed in real-time by measuring the increase in fluorescence at 520 nm. Sodium orthovanadate was added to the reaction mix prior to enzyme addivity to give final concentrations of (0.03–30 $\mu$M). Results indicate an IC$_{50}$ value for vanadate of 0.25 $\mu$M and are shown in FIG. 6.

EXAMPLE 6

Assay of Chk1 Kinase Using Solution Phase FP Assay with Fluorescein Labelled CDC25 Derived Peptide Substrate and 14-3-3ζ Binding Partner This assay was performed to measure Chk1 activity by measuring the fluorescence polarisation change that occurs as a result of the Chk1 protein kinase-mediated binding of fluorescein labelled Chktide to 14-3-3 protein.

Chk1 protein kinase modifies the activity of CDC25 phosphatase via serine phosphorylation. Phosphorylation of CDC25 results in the binding of different isoforms of the 14-3-3 protein and subsequent inhibition of CDC25 phosphatase activity. A peptide derived from CDC25 (Chktide) and labelled with a chemical fluorophore binds to 14-3-3 isoforms zeta and epsilon when phosphorylated by Chk1 kinase. The activity of Chk1 is monitored by following the fluorescence polarisation change when fluorescein labelled Chktide binds to 14-3-3 protein.

Methods

Reagent sources 14-3-3-ζ protein, Chk1 enzyme and Ckhtide peptide are from Upstate Biotechnology. Chktide, Chk1 substrate peptide sequence: KKKVSRSGLYRSPS$^{216}$MPENLNRPR, SEQ ID NO:10

Chktide labelling with fluorescein

Chktide was labelled by incubating the peptide for 2 hours at a concentration of 0.185 mM in 100 mM NaHCO$_3$, pH 8.3, and 0.37 mM fluorescein-5EX (Molecular Probes) at room temperature. The labelled peptide was then dialysed against 3 changes of 50 mM Tris HCL pH 7.4, 150 mM NaCl (200 ml) for a total of 18 hours.

Phosphorylation of Chktide by Chk1 protein kinase.

A peptide substrate for Chk1 (Chktide) was labelled with fluorescein. The labelled peptides were then phosphorylated by incubating them at a concentration of 30 μM for 30 min at 30° C. in 20 mM MOPS pH 7.2, 10 mM MgCl$_2$, 25 mM β-glycerophosphate, 5 mM EGTA, 1 mM sodium orthovanadate, 1 mM DTT, 0.1 mM ATP, and 62 mU Chk1. Non phosphorylated control samples were prepared by incubation of the labelled peptides under identical conditions in the absence of Chk1. The peptides were then incubated at a concentration of 5 μM in 20 mM MOPS pH 7.2 at 30° C., in a total volume of 30 μl on a half area 96 well plate. The fluorescence polarisation of the samples was measured at 520 nm (excitation 485 nm) following a 5 min equilibration. 14-3-3ζ (5 μM) was added to the peptide samples, and the fluorescence polarisation at 520nm (excitation 485 nm) was monitored over time as shown in FIG. 7. Inhibition of Chk1 activity by EDTA was measured by following the above procedure and adding EDTA (10 mM or 20 mM) prior to enzyme addition, as shown in FIG. 8.

Activity of Chk1 was monitored in real time as follows. Fluorescein labelled Chktide was incubated at 30° C. in a total volume of 30 μl (on a half area 96 well plate) in 20 mM MOPS pH 7.2, 10 mM MgCl$_2$, 25 mM β-glycerophosphate, 5 mM EGTA, 1 mM sodium orthovanadate, 1 mM DTT, and 0.1 mM ATP in the presence of 5 μM 14-3-3 ζ. The samples were allowed to equilibrate for 5 min, then Chk1 was added (or an equal volume of H$_2$O for control samples) and the fluorescence polarisation at 520 nm (excitation 485 nm) was monitored over time as shown in FIG. 9. Dependence of the increased fluorescence polarisation signal on Chk1 activity and 14-3-3ζ binding was shown by the lack of binding when ATP or 14-3-3ζ protein was omitted from the real time enzyme reaction as shown in FIG. 10. Inhibition of Chk1 activity by EDTA was measured by following the above procedure and adding EDTA (1 mM, 5 mM or 20 mM) prior to the addition of 21 mU of Chk1 to start the reaction, as shown in FIG. 11. The fluorescence polarisation for each sample was determined at the end of the linear portion of the reaction.

Chk1 activity was also measured by monitoring the binding of phosphorylated Chktide peptide to an alternate isoform of the 14-3-3 protein, 14-3-3ε.

Production of 14-3-3 ε

Under the control of the T7 promoter, the vector FS 121 contains DNA encoding the 14-3-3ε (Genbank accession number U54778) protein fused in-frame to DNA encoding an amino terminal hexa-His tag. Fresh transformants of pFS 121 in BRL(DE3) pLysS were used to inoculate 3 ml LB/ampicillin (100 μg/ml). The starter cultures was incubated overnight at 37° C. with shaking. From these starter cultures 1 ml was used to inoculate 400 ml Terrific Broth/ ampicillin (100 μg/ml) in a 2L, baffled flask. Cultures were incubated at 37° C. at 200 rpm for approximately 4 hr until the OD$_{600}$ nm reached 0.5 Abs units. At this point cultures were induced by adding IPTG to a concentration of ImM and further incubated at 37° C. for 4 hrs.

Bacteria were harvested by centrifugation at 3000 rpm for 20 min. The bacterial pellet was resuspended in 25 ml lysis buffer (50 mM Phosphate pH 7.0, 30 mM NaCl, 2% Proteinase inhibitor cocktail (Sigma), 0.75 mg/ml Lysozyme). Lysis of the resuspended cells was initiated by gentle stirring for 30 min at room temperature. Nonidet P-40 was added to a final concentration of 1% and lysis was continued for an additional 20 min at room temperature. The partially lysed mixture was subjected to 3 cycles of freeze thawing in liquid nitrogen. Finally the cells were sonicated on ice using a 10 mm probe at high power. Sonication was performed on a pulse setting for a period of 4 min. The crude lysate was centrifuged at 15,000 rpm for 30 min to remove cell debris. Hexa-His tagged proteins were purified from the cleared lysate using TALON® resin (Clontech). Proteins were bound to the resin in a batchwise manner by gentle shaking at room temperature for 30 min. Non-His tagged proteins were removed by washing the resin at least twice with a 10× bed volume of wash buffer (50 mM sodium phosphate pH 7.0, 300 mM NaCl, 5 mM fluorescence-blank Imidazole ). The washed resin was loaded into a 2 ml column and the bound proteins were released with elution buffer (50 mM sodium phosphate, pH 7.0, 300 mM NaCl, 150 mM fluorescence-blank Imidazole). Elution was normally achieved within 5 ml. Purified proteins were stored at −80° C. after snap freezing in liquid nitrogen in the presence of 10% glycerol.

End point assay of Chk1 kinase by 14-3-3ε binding to phosphorylated Chktide

A peptide substrate for Chk1 (Chktide) was labelled with fluorescein. The labelled peptides were then phosphorylated by incubating them at a concentration of 30 μM for 30 min at 30° C. in 100 l of 20 mM MOPS pH 7.2, 10 mM MgCl$_2$, 25 mM β-glycerophosphate, 5 mM EGTA, 1 mM sodium orthovanadate, 1 mM DTT, 0.1 mM ATP, and 62 mU Chk1. Non-phosphorylated control samples were prepared by incubation of the labelled peptides under identical conditions in the absence of Chk1. The peptides were then incubated at a concentration of 7.5 μμM in 20 mM MOPS pH 7.2 at 30° C., in a total volume of 30 μl on a half area 96 well plate. The fluorescence polarisation of the samples was measured at 520 nm (excitation 485 nm) following a 5min equilibration. 14-3-3 ε (4 μl) was added to the peptide samples, and the fluorescence polarisation at 520 nm (excitation 485 nm) was monitored over time as shown in FIG. 12.

EXAMPLE 7

Solution phase FP assay for the detection of phosphatase λ activity using a fluorescein labelled CDC25 derived peptide substrate and 14-3-3ζ binding partner These assays were performed to demonstrate measurement of phosphatase 1 activity as detected by a change in fluorescence polarisation due to decreased binding of Chktide to 14-3-3 ζ or 14-3-3 ε. Binding is decreased as a result of dephosphorylation of Chktide by phosphatase λ.

Reagents were obtained and prepared as in example 6 above.

Fluorescein labelled Chktide was phosphorylated by incubation at a concentration of 30 μM for 30 min at 30° C. in 20 mM MOPS pH 7.2, 10 mM $MgCl_2$, 25 mM ε-glycerophosphate, 5 mM EGTA, 1 mMsodium orthovanadate, 1 mM DTT, 0.1 mM ATP, and 62mU Chk1. Non-phosphorylated control samples were prepared by incubation of the labelled peptides under identical conditions in the absence of Chk1. The peptides were then incubated at a concentration of 7.5 μM in 20 mM MOPS pH 72, 2 mM $Mncl_2$, 1 mM DTT at 30° C., in a total volume of 30 μl on a half area 96 well plate. The fluorescence polarisation of the samples was measured at 520 nm (excitation 485 nm) following a 5 min equilibration. 14-3-3 ζ (5 μM) was added to the peptide samples, and the fluorescence polarisation at 520 nm (excitation 485 nm) was monitored over time as shown in FIG. 13. Alternatively 14-3-3 ε (4 μl of purified protein prepared as in Example 6) was added to the peptide samples, and after the fluorescence polarisation was stabilised, phosphatase λ(200U) was added. The fluorescence polarisation at 520 nm (excitation 485 nm) was monitored over time as shown in FIG. 14.

EXAMPLE 8

Simultaneous Assay of Two Serine Threonine Kinases, Chk1 and cAMP Dependent Protein Kinase (PKA) by FP This assay was performed to simultaneously measure the activity of Chk1 and PKA by monitoring a change in fluorescence polarisation due to association or dissociation of peptides and/or proteins capable of associating in a manner that is dependent upon their phosphorylation state. Following phorphorylation by PKA, coiled coil dimers can no longer form. Conversely, phosphorylation of Chktide by Chk1 results in binding of Chktide to a 14-3-3 protein.

Serine threonine kinases PKA and Chk1 can be assayed simultaneously using the natural binding partner reporters described in example 5 for Chk1 and a peptide based binding partner assay for PKA (described in WO99/11774).
Methods
PKA Peptide sequences:

Peptide 1. ERE IKALERE IRRLRRA SQALERE IAQLERE, SEQ ID NO:11

Peptide 2. LRQR IQCLRYR IRRLRRA SQALRQR IAQLKQR, SEQ ID NO:12

PKA peptides form coiled-coil dimers when they are non-phosphorylated. Each monomer has a PKA phosphorylation site. Following phosphorylation by PKA, the dimers can no longer form. The association/dissociation can be measured using a fluoescence polarisation assay, where PKA peptide 1 is labelled with coumarin, and peptide 2 is labelled with biotin and bound to streptavidin. The tumbling rate of coumarin labelled peptide 1 is higher after PKA phosphorlation and dissociation from the dimer/streptavidin complex. At the same time, the activity of Chk1 is measured by the decrease in tumbling rate of phosphorylated fluorescein labelled Chktide substrate binding to 14-3-3ε protein.

The labelled PKA peptides (both at a concentration of 2.5 μM) were incubated at 30° C. in a total volume of 50 μ (on a half area 96 well plate) in 20 mM MOPS pH 7.2, 10 mM $MgCl_2$, 25 mM β-glycerophosphate, 5 mM EGTA, 1 mM sodium orthovanadate, 1 mM DTT, and O.ImM ATP, 7.5 μM Chktide, 3 μL 14-3-3 ε and 0.06U streptavidin. The samples were allowed to equilibrate for 5 min, then CHK1 (62 mU) and PKA (0.5 pmoles) were added (or an equal volume of $H_2O$ for control samples). The fluorescence polarisation at 520 nm (excitation 485 nm) and at 450 nm (excitation 340 nm) was monitored over time as shown in FIG. 15.

EXAMPLE 9

FRET Assay of Src Using ZAP70-GFP Binding Partner and Synthetic Rhodamine Labelled TCRζ Substrate These FRET-based assays were performed to detect Src activity by measuring the Src dependent formation of a complex between an SH2 domain of ZAP-70 labelled with a fluorophore and a peptide based on the TCRζ chain labelled with a fluorophore.

A FRET partnership can be formed in a phosphorylation dependent manner between the SH2 domain of ZAP-70 and a peptide based on the TCRζ chain, providing both binding partners are labelled with suitable fluorophores. Src is used to phosphorylate the TCRζ chain derived substrate.
Methods:
TCR peptide sequence Peptide 1. Phosphorylated TCRC chain: RCKFSRSAEPPAYQQGQNQLY$_{(p)}$NELNLGRREEY$_{(p)}$ DVLD, SEQ ID NO: 13

Peptide 2. Unphosphorylated TCRζ chain: RCKFSR-SAEPPAYQQGQNQLYNELNLGRREEYDVLD, SEQ ID NO: 14

Peptide labelling

Peptides 1 and 2 were labelled with rhodamine under mild conditions using thiol directed chemistry. 230 μM peptide was labelled in 2 mM TES pH 7 in the presence of a three-fold excess of rhodamine-6-maleimide (Molecular Probes). Dialysis was utilised to remove excess dye from the peptide. Labelling was verified by MALDI-TOF MS.
ZAP-GEP cloning and purification ZAP-GFP was cloned and purified as described in Example 5.
Phosphorylation of Peptide 2

Peptide 2 labelled with rhodamine was phosphorylated using 3 units of Src kinase (Upstate Biotechnology) in a 40 μl reaction containing 115 μM peptide, 50 mM Tris-HCl pH 7.2, 1 mM ATP, 10 mM $MgCl_{2, 10}$ mM β-mercaptoethanbl, 0.1 mg/ml BSA and 0.015%(v/v) Brij 35, over a period of 2 hours at 37° C. Non-phosphorylated control samples were prepared under identical conditions in the absence of the kinase.
Formation of the FRET partnership ZAP-GFP was diluted to 0.5 μM in assay buffer (50 mM Tris pH 7.2, 10 mM β-mercaptoethanol, 0.5mg/ml BSA, 0.015% Brij 35). 98 μl of this solution was used per assay. Initial readings of the fluorescence of the ZAP-GFP construct were made using 485 nm excitation wavelength and 520 nm emission wavelength. Rhodamine labelled peptide (2 μl of above phosphorylation reactions) was added to the ZAP-GFP solution and formation of FRET was followed in real-time by measuring the decrease in fluorescence emission of ZAP-GFP at 520 nm as shown in FIG. 16.

EXAMPLE 10

Solution Phase FRET Assay of Src Kinase Activity Using a Natural Binding Partner, SHP-2 Labelled with a Fluorescent Protein These FRET-based assays are performed to measure Src kinase activity as determined by the Src kinase dependent formation of a complex between the SH2 domain of SHP2 labelled with a fluorophore and an synthetic peptide based on SHPS-1, also labelled with a fluorophore.

Interaction between the tandem SH2 domain of SHP2 and a synthetic peptide based on SHPS-1 is mediated by the state of phosphorylation of the peptide. A FRET partnership can be established between phosphorylated peptide and the SH2 domain providing both moieties are labelled with suitable fluorophores which are brought into close proximity upon interaction of binding partners.

SUP2 peptide sequence and fluorescent labelling

SHPS-1 peptide sequence. BiotinKQDTNDIT YADLNLPKGKKPAPQAAEPNNHTEYASIQTSC, SEQ ID NO:14

The SHPS-I was labelled using thiol directed chemistry. 200 µM peptide was reacted with 600 µM rhodamine-6-maleimide (Molecular Probes) in 20 mM TES pH 7 over a period of at least two hours at room temperature. Excess label was removed using dialysis and the labelling was verified by MALDI-TOF MS.

SHP2-GFP cloning and purification

Primers were based on the published SHP-2 DNA sequence (Genbank accession number L03535. The SH2 domain (amino acids 1–225) of SHP-2 was cloned by PCR using the following oligo-nucleotides:

5'primer-GGGGATCCTCTAGAATGACATCG CGGAGATGGTTTCACCC, SEQ ID NO: 15

3'primer-GGGGAATTCTTTCAGCAGCATTTA TACGAGTCG, SEQ ID NO:16

The resultant PCR fragment was digested with XbaI and EcoRI, gel purified and ligated into pET28a (Novagen) to generate vector pFS114. The validity of the construct was confirmed by sequence analysis. DNA encoding GFP in the vector pFS46 was isolated by digestion with the restriction enzymes EcoRI and XhoI and the resultant 860 bp band was gel purified and ligated into pFS114 to generate a bacterial expression vector for production of the fusion protein SHP2-GFP (pFS115).

The hexa-His tagged SHP2-GFP fusion protein was expressed and purified using TALON® resin according to standard procedures.

Phosphorylation of peptide SHPS-1 peptide

SHPS-1 peptide labelled with rhodamine was phosphorylated using 3 units of Src kinase (Upstate Biotechnology) in a 40 µl reaction containing 100 µM peptide, 50 mM Tris-HCl pH 7.2, 1 mM ATP, 10 mM MgCl$_2$, 10 mM β-mercaptoethanol, 0.1 mg/ml BSA and 0.015% (v/v) Brij 35, over a period of 2 hours at 37° C. Non-phosphorylated control samples were prepared under identical conditions in the absence of the kinase.

Formation of the FRET partnership

SHP2-GFP was diluted to 0.5 µM in assay buffer (50 mM Tris HCL pH 7.2, 10 mM β-mercaptoethanol, 0.5 mg/ml BSA, 0.015% Brij 35). 98 µl ofthis solution was used per assay. Initial readings of the fluorescence of the SHP2-GFP construct were made using 485 nm excitation wavelength and 520 nm emission wavelength. Rhodamine labelled peptide (2 µl of the above phosphorylation reactions) was added to the SHP2-GFP solution and formation of FRET was monitored in real-time by measuring the decrease in fluorescence emission of SHP2-GFP at 520 nm as shown in FIG. 17.

Disruption of the FRET partnership

The FRET partnership described in the above section was disrupted easily using the tyrosine phosphatase enzyme, YOP (Upstate Biotechnology). FRET partnership was formed as in the above example, using 4 µl of phosphorylated or control non-phosphorylated SHPS-1 peptide. Addition of 3 units of YOP to the FRET partnership resulted in disruption of the FRET partnership as the phosphotyrosines required for the formation of the partnership were removed (shown in FIG. 18).

Inhibition by Staurosporine

Phosphorylation of the peptide was prevented by inhibiting the enzyme, Src, with the potent kinase inhibitor staurosporine. Phosphorylation of the rhodamine labelled SHPS-1 peptide was performed as described above in the presence or absence of 10 µM staurosporine added to the reaction prior to the addition of the Src enzyme. The SH2 domain of SHP2 and the SHPS-1 peptide failed to form a FRET partnership in the presence of the inhibitor, as shown in FIG. 19.

Assay of Src phosphorylation of SHPS-1 peptide in real-time

Phosphorylation of the rhodamine labelled SHPS-1 peptide and formation of the FRET partnership with SHP2-GFP was followed in real-time by measuring the decrease in fluorescence emission at 520 nm. Reactions containing 0.5 µM SHP2-GFP, 50 mM Tris-HCl pH 7.2, 1 mM ATP, 10 mM MgCl$_2$, 10 mM µ-mercaptoethanol, 0.5 mg/ml BSA, 0.015% Brij 35 and 40 µM peptide were set up in a black microtitre plate. An initial equilibrium measurement was made before adding 6 units of Src kinase, or buffer to control wells. The decrease in fluorescence emission at 520 nm was followed in real-time at 37° C. as shown in FIG. 20.

EXAMPLE 11

In Vivo Measurement of Kinase or Phosphatase Activity

The enzymatic activity of a kinase or phosphatase enzyme is measured in an in vivo assay performed as follows.

In vivo assays are carried out by transfecting cells with a first expression construct encoding a fusion protein comprising a polypeptide comprising a natural binding domain and further comprising a site for phosphorylation fused in frame to a fluorescent protein and a second expression construct comprising a polypeptide comprising a binding partner for the natural binding domain fused in frame to a second fluorescent protein. Alternatively, cells are transfected with a tandem construct encoding a fusion protein comprising a natural binding domain that includes a site for phosphorylation and a binding partner for the natural binding domain, and two different fluorescent proteins. For all experiments, binding of a natural binding domain to its binding partner is dependent on phosphorylation or dephosphorylation.

Plasmids encoding the autofluorescent proteins (AFPs) red shifted green fluorescent protein (rsGFP) and blue fluorescent protein (BFP) are purchased from Quantum Biotechnologies, Inc. BFP is a mutated version of the 28 kDa rsGFP. BFP has an excitation peak of 387 nm and an emission peak of 450 nm. GFP has an excitation peak of 473 nm and an emission peak of 509 nm.

Constructs

DNA primers are designed encoding a first polypeptide comprising a natural binding and a phosphorylation site domain or a second polypeptide comprising a binding partner for the first polypeptide, a stop codon and unique restriction sites (e.g. BamHI and EcoRI) at each end to facilitate cloning. Codon usage is selected in order to allow both mammalian and bacterial expression. Alternatively, DNA primers are designed to encode a polypeptide comprising both a natural binding domain that includes a phosphorylation site and a binding partner for the natural binding domain.

Experiments are performed using the following pair of polypeptides:

1. v-SRC SH2 domain (amino acids 148–246; Waksman et al., supra; OWL database accession no. M33292 and hamster polyomavirus middle T antigen (Ag) (321–331, EPQYEEIPIYL, SEQ ID NO: 17), Waksman et al., supra; OWL database accession no. P03079, 2. Phosphotyrosine binding domain (PTB) of IRS-I (amino acids 157–267) Zhou et al., supra; OWL accession no. P35568 and interleukin 4 receptor (Il-4R) (anino acids 489–499, LVIAGNPAYRS, SEQ ID NO: 18; Zhou et al., supra; OWL database accession no. P24394, and 3. The PTB domain of the proto-oncogene product Cbl (the Cbl N-termninal binding domain) (amino acids 1–357); Lupher et al., supra; OWL accession no. P22681 and a peptide derived from the Zap-70 tyrosine kinase (amino acids 284–299, $NH_3$-IDTLNSDGYtpepARI- COOH, SEQ ID NO:19); Lupher et al., supra; OWL accession no. P43403.

4. SH2 domain of ZAP70 (residues 1–259), GenBank accession No. L05148. Tandem phosphorylation motif of TCRseta chain (residues 52–163) GenBank accession No. J04132.

Experiments are also performed using a construct encoding a polypeptide comprising a natural binding domain including a site for phosphorylation and further comprising a natural binding partner for the natural binding domain.

These experiments are performed using the polypeptide c-SRC (residues 86–536); Xu et al., supra; GenBank Accession No. K03218.

AEP-polypeptide construction

The purified DNA fragment, isolated by PCR is digested with the appropriate enzymes that cleave at the unique restriction sites located at each end and purified as above prior to ligation into the mammalian expression vectors pQBI25-fcl and pQBI50-fcl.

The v-SRC-SH2 domain and the polyomavirus middle T-antigen peptide are cloned such that the AFP is placed at the N-termini. The AFPs can be fused either to the N or C-termini of the PTB domain of IRS-1 and the IL-4R peptide.

In the case of the tandem construct expressing the c-SRC polypeptide which includes both a natural binding domain, including a site of phosphorylation and a natural binding partner for the natural binding domain, chemical modification by the kinase or phosphatase enzyme being assayed is monitored by measuring a change in an intramolecular reaction. A nucleic acid encoding a natural binding domain including a site of phosphorylation and its binding partner to be expressed as part of a single-polypeptide, additionally encodes, at a minimum, a donor AFP fused to the natural binding domain and an acceptor AFP fused to its binding partner, a linker that couples the two AFPs and is of sufficient length and flexibility to allow for folding of the polypeptide and pairing of the natural binding domain, sequence or polypeptide with the binding partner, and gene regulatory sequences operatively linked to the fusion coding sequence.

To prepare a construct encoding a polypeptide comprising a natural binding domain and further comprising a natural binding partner for the natural binding domain and two different AFP proteins, the purified DNA (prepared as above) is ligated into a vector encoding an AFP. A fragment encoding the polypeptide plus an AFP protein is excised from the vector and ligated into a second vector encoding a linker and a second AFP. Alternatively, the purified DNA (prepare as above) is ligated into a vector encoding an AFP. A DNA fragment encoding a linker and a second AFP is ligated into the above construct (by digestion with appropriate restriction enzymes) resulting in a construct encoding a polypeptide comprising a natural binding domain, a natural binding partner for the natural binding domain and two AFPs separated by a linker.

FRET in Mammalian cells

Experiments are performed using pairs of vectors expressing the following proteins: a polypeptide comprising a natural binding domain including a phosphorylation site and an AFP and a polypeptide comprising a natural binding partner of the natural binding domain and a second AFP.

Vectors capable of expressing these proteins are transfected into COS-7 cells (a well-established cell-line derived from monkey kidney cells) individually and in combination. Transfections are performed using Lipofectamine 2000 (GibcoBRL) and the transfected cells are incubated at 37° C. for 48 hr (to allow the expressed proteins to accumulate to a detectable level) in the presence or absence of a kinase activator, a candidate modulator of kinase activity or both a kinase activator and a candidate modulator of kinase activity. Alternatively, the transfected cells are incubated in the presence or absence of a phosphatase activator, a candidate modulator of phosphatase activity or both a phosphatase activator and a candidate modulator of phosphatase activity.

Additional experiments are performed (using the transfection protocol described above) using a tandem vector expressing a polypeptide comprising a natural binding domain including a phosphorylation site, a natural binding partner of the natural binding domain and two different AFPs separated by an appropriate linker. As above, transfected cells are incubated for 48 hrs in the presence or absence of a kinase, a candidate modulator of kinase activity, both a kinase and a candidate modulator of kinase activity, a phosphatase, a candidate modulator of phosphatase activity or both a phosphatase and a candidate modulator of phosphatase activity.

Following the 48 hr incubation period the amount of FRET is determined by analysis in a BMG Galaxy fluorescent plate reader using the following regime: excitation at 370 nm (excitation for BFP) and emission at 520 nm (emission for GFP). USE The invention is useful in monitoring the activity of a protein kinase or phosphatase, whether the protein is isolated, partially-purified, present in a crude preparation or present in a living cell. The invention is further useful in assaying a cell or cell extract for the presence- or level of activity of a protein kinase or phosphatase. The invention is additionally useful in assaying the activity of naturally-occurring (mutant) or non-natural (engineered) isoforms of known protein kinases and/or phosphatases or, instead, that of novel (natural or non-natural) enzymes. The invention is of use in assaying the efficacy of candidate modulators of the activity of a protein kinase or phosphatase in inhibiting or enhancing the activity of that enzyme; moreover, is useful to screen potential therapeutic drugs for activity against cloned and/or purified enzymes that may have important clinical pathogenicities when mutated. The invention is further of use in the screening of a candidate bioactive agent (e.g., drugs) for side effects, whereby the ability of such an agent to modulate the activity of a protein kinase or phosphatase may be indicative a propensity toward provoking unintended side-effects to a therapeutic or other regimen in which that agent might be employed.

OTHER EMBODIMENTS

Other embodiments will be evident to those of skill in the art. It should be understood that the foregoing description is provided for clarity only and is merely exemplary. The spirit and scope of the present invention are not limited to the above examples, but are encompassed by the following claims.

What is claimed is:

1. A method of screening for a candidate modulator of enzymatic activity of a kinase or a phosphatase, the method comprising
   a) contacting an isolated natural binding domain, a binding partner therefor and an enzyme with a candidate modulator of said kinase or phosphatase, wherein said natural binding domain includes a site for post-translational phosphorylation and binds said binding partner in a manner that is dependent upon phosphorylation or dephosphorylation of said site by said kinase or phosphatase and wherein at least one of said isolated natural binding domain and said binding partner comprises a detectable label;
   b) detecting the binding or dissociation of said isolated natural binding domain to/from said binding partner; and
   c) monitoring the binding of said isolated natural binding domain to said binding partner, wherein binding or dissociation.of said isolated natural binding domain and said binding partner as a result of said contacting is indicative of modulation of enzymatic activity by said candidate modulator of said kinase or phosphatase.

2. The method according to claim 1, wherein said detectable label emits light.

3. The method according to claim 2, wherein said light is fluorescent.

4. The method according to claim 1, wherein said monitoring comprises measuring a change in energy transfer between a detectable label present on said isolated natural binding domain and a detectable label present on said binding partner.

5. A method of screening for a candidate modulator of enzymatic activity of a kinase or a phosphatase, the method comprising
   a) contacting a cell-free assay system comprising an isolated natural binding domain and a binding partner therefor with a candidate modulator of enzymatic activity of a said kinase or phosphatase;
   b) detecting the binding or dissociation of said isolated natural binding domain to/from said binding partner; and
   c) monitoring binding of said isolated natural binding domain and said binding partner therefor in said assay system, wherein said isolated natural binding domain includes a site for post-translational phosphorylation and binds said binding partner in a manner that is dependent upon phosphorylation or dephosphorylation of said site by a said kinase or phosphatase in said assay system, wherein at least one of said isolated natural binding domain and said binding partner comprises a detectable label, and wherein binding or dissociation of said isolated natural binding domain and said binding partner as a result of said contacting is indicative of modulation of enzymatic activity by said candidate modulator of a said kinase or phosphatase.

6. The method according claim 1 or 5, wherein said method comprises real-time observation of association of a said isolated natural binding domain and its binding partner.

* * * * *